US005698691A

United States Patent [19]

Yukimasa et al.

[11] Patent Number: 5,698,691

[45] Date of Patent: Dec. 16, 1997

[54] CONDENSED CYCLIC COMPOUNDS AND THEIR USE

[75] Inventors: Hidefumi Yukimasa, Nara; Ryuichi Tozawa, Ibaraki; Yasuo Sugiyama, Kawanishi; Masakuni Kori, Miki, all of Japan

[73] Assignee: Takeda Chemical Industries, Ltd., Osaka, Japan

[21] Appl. No.: 311,932

[22] Filed: Sep. 26, 1994

[30] Foreign Application Priority Data

Sep. 24, 1993 [JP] Japan .................................. 5-238273
Sep. 28, 1993 [JP] Japan .................................. 5-241062

[51] Int. Cl.[6] .................................. C07D 267/02

[52] U.S. Cl. .................. 540/490; 540/545; 540/552; 540/554; 540/567

[58] Field of Search .................. 540/490, 545, 540/552, 554, 567

[56] References Cited

U.S. PATENT DOCUMENTS

| | | | |
|---|---|---|---|
| 3,205,223 | 9/1965 | Bell | 260/239 |
| 3,259,633 | 7/1966 | Metlesics et al. | 260/326.16 |
| 3,320,239 | 5/1967 | Stempei et al. | 260/239 |
| 3,340,253 | 9/1967 | Reeder et al. | 260/239.3 |
| 3,400,119 | 9/1968 | Wenner et al. | 260/239.3 |
| 3,463,774 | 8/1969 | Wenner et al. | 260/239.3 |
| 3,562,251 | 2/1971 | Fryer et al. | 260/239 |
| 3,644,419 | 2/1972 | Metlesics et al. | 260/333 |
| 3,723,414 | 3/1973 | Steinman | 260/239 BD |
| 3,786,144 | 1/1974 | Steinman | 424/244 |
| 3,891,630 | 6/1975 | Swett | 540/490 |
| 4,237,049 | 12/1980 | Britton et al. | 260/239 BD |

FOREIGN PATENT DOCUMENTS

| | | |
|---|---|---|
| 0 142 361 | 5/1985 | European Pat. Off. . |
| 0 264 797 | 4/1988 | European Pat. Off. . |
| 0 475 706 | 3/1992 | European Pat. Off. . |
| 0 567 026 | 10/1993 | European Pat. Off. . |
| 2 528 838 | 12/1983 | France . |
| 1 695 129 | 2/1970 | Germany . |
| 45-11148 | 4/1970 | Japan . |
| 57-35576 | 2/1982 | Japan . |
| 144 211 | 11/1966 | New Zealand . |
| 144 212 | 11/1966 | New Zealand . |
| 140 678 | 8/1967 | New Zealand . |
| 140 702 | 11/1968 | New Zealand . |
| 140 734 | 11/1968 | New Zealand . |
| 162 737 | 7/1972 | New Zealand . |
| 159 120 | 10/1973 | New Zealand . |
| 166 133 | 4/1974 | New Zealand . |
| 167 984 | 6/1974 | New Zealand . |
| 184 012 | 11/1981 | New Zealand . |
| 212 502 | 3/1989 | New Zealand . |
| 223 772 | 9/1991 | New Zealand . |
| 568 995 | 11/1975 | Switzerland . |
| 2 075 012 | 11/1981 | United Kingdom . |
| WO 92/01683 | 2/1992 | WIPO . |
| WO 92/15579 | 9/1992 | WIPO . |
| WO 93/07129 | 4/1993 | WIPO . |
| WO 93/16055 | 8/1993 | WIPO . |

OTHER PUBLICATIONS

Sato et al., "Regiochemistry of Radical Cyclisations (6–exo/7–endo and 7–exo/8–endo) of N–(o–Alkenylphenyl)–2,2–dichloroacetamides," J. Chem. Soc. Perkin Trans. 1, 1991, pp. 353–359.

Sato et al., "New Entries to 2(1H)–Quinolinones and 2H–1–Benzazepin–2–ones by Acid–Catalyzed Olefin Cyclization of N–[o–(Alk–1–enyl)phenyl]–2–(methylsulfinyl)acetamides," Chem. Pharm. Bull. 38 (12), 1990, pp. 3331–3334.

Barsky et al., "Hypoglycemic Cyclic Amidines," Journal of Medicinal Chemistry, vol. 14, No. 1, 1971, pp. 40–44.

Loev et al., "Benzazepinones. Synthesis of the Monoaza Analog of Diazepam, and the Correct Structure of the Benzoylpropionanilide Cyclization Product," Journal of Medicinal Chemistry, vol. 14, No. 9, 1971, pp. 849–852.

Corbella et al., "Sterochemistry of the Enzymic 3–Hydroxylation of 1,3–Dihydro–2H–1,4–benzodiazepin–2–ones," J.C.S. Chem. Comm., 1973, pp. 721–722.

Walser et al., "Quinazolines and 1,4–Benzodiazepines. LIX.[1] Preparation of Pyrrolo[2,1–c]–1,4–benzodiazepines," J. Org. Chem., vol. 38, No. 20, 1973, pp. 3502–2507.

Bock et al., "Curtius Rearrangement in the 5–Phenyl–1,4–benzodiazepine Series. Unprecedented Participation by an Imine Nitrogen," J. Heterocyclic Chem. 27, 1990, pp. 631–636.

(List continued on next page.)

Primary Examiner—Bernard Lipman
Attorney, Agent, or Firm—Foley & Lardner

[57] ABSTRACT

Disclosed is a squalene synthetase inhibitor which comprises the compound represented by the formula

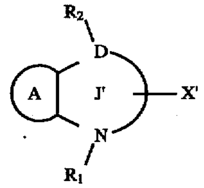

wherein $R_1$ is hydrogen or an optionally substituted hydrocarbon group; $R_2$ is hydrogen, an optionally substituted alkyl group, an optionally substituted phenyl group or an optionally substituted aromatic heterocyclic ring group; X' is a substituent comprising an optionally esterified carboxyl group, an optionally substituted carbamoyl group, an optionally substituted hydroxyl group, an optionally substituted amino group or an optionally substituted heterocyclic radical having a protonizable hydrogen; Ring A is an optionally substituted benzene ring or an optionally substituted aromatic heterocyclic ring; Ring J' is a 7- to 8-membered heterocyclic ring containing at most three ring constituting hetero atoms; D is C or N; the Ring J' optionally having, besides $R_1$, $R_2$ and X', a further substituent; provided that the condensed ring composed of Ring A and ring J' is not a 2-oxo-1,2,3,5-tetrahydro-4,1-benzoxazepine ring, or a pharmaceutically acceptable salt thereof, and which is useful for the prophylaxis or therapy of hypercholesteremia or coronary sclerosis of mammals.

15 Claims, No Drawings

OTHER PUBLICATIONS

Chemical Abstracts, Published by the American Chemical Society, vol. 82, Jun. 16–Jun. 30, 1975, Abstract No. 156233g.

Shimamoto et al., "Pharmacological Screening of New Benzodiazepines in Mice," J. Takeda Res. Lab. 29, 1970, pp. 134–144.

Kuch et al., "Die Synthese von 5–Phenyl–4,1–benzothiazepin–Derivaten*)," Arch. Pharm. 300, 1967, pp. 299–308.

Klosa, "Synthese von Benzothiazepinonen", einer neuen Körperklasse, J. Prakt Chem., 36, 5, 1967, pp. 5–18.

Fryer et al., "[1,4]Diazepines with [b]–Fused Rings," Bicyclic Diazepines, 1991, pp. 289–305.

Taylor et al., "Synthesis of Some 1H–1,3–Benzodiazepines," J. Chem. Soc. Perkin Trans. 1, 12, 1976, pp. 1331–1338.

Masuoka et al., "Syntheses of Medium–Sized Heterocycles Using an Intramolecular Michael Reaction," Chem. Pharm. Bull., 34, 1, 1986, pp. 140–149.

Biller et al., "Isoprenoid (Phosphinylmethyl)phosphonates as Inhibitors of Squalene Synthetase," Journal of Medicinal Chemistry, vol. 31, No. 10, 1988, pp. 1869–1871.

CONDENSED CYCLIC COMPOUNDS AND THEIR USE

FIELD OF THE INVENTION

This invention relates to a condensed cyclic compound or a salt thereof, and, to a squalene synthetase inhibitor comprising same as the effective component.

BACKGROUND OF THE INVENTION

Hypercholesteremia, high blood pressure and smoking are known as three major dangerous factors of causing ischemic heart diseases. Adequate control of cholesterol concentration in blood is remarkably important for the prophylaxis or therapy of, besides these ischemic heart diseases, as well as of coronary sclerosis.

As pharmaceutical compositions for lowering cholesterol in blood, attention has been drawn to those for controlling the biosynthesis of cholesterol, besides those of inhibiting its absorption by binding bile acid including, among others, cholestyramine, colestipol (disclosed in, for example, U.S. Pat. No. 4,027,009), and those of suppressing the intestinal absorption of cholesterol by inhibiting acyl coenzyme A cholesterol acyl transferase (ACAT) including melinamide (disclosed in French Patent No.1476569). As pharmaceutical preparations for controlling the biosynthesis of cholesterol, lovastatin (disclosed in U.S. Pat. No. 4,231,938), simvastatin (disclosed in U.S. Pat. No. 4,444,784), pravastatin (U.S. Pat. No. 4,346,227), etc., which are capable of inhibiting especially 3-hydroxy-3-methyl glutaryl coenzyme (HMG-CoA) reductase, are provided for medicinal use. However, when HMG-CoA reductase is inhibited, not only the biosynthesis of cholesterol but the biosynthesis of some other components such ubiquinone, dolichol and heme A, which are necessary for the living body, is also inhibited, so that occurrences of undesirable side effects to be caused thereby are feared.

Squalene synthetase is an enzyme taking part in the essential step of new cholesterol biosynthetic route. And, this enzyme is an enzyme forming squalene catalyzing the reductive dimerization of two molecules of farnesyl pyrophosphoric acid.

On the other hand, the compounds expected as inhibitors of cholesterol biosynthesis by inhibiting squalene synthetase are disclosed in Journal of Medicinal Chemistry, Vol. 51, No. 10, pp. 1869–1871, 1988, Japanese published unexamined patent application No. H1-213288/1989 (JPA H1(1989)-213288), JPA H2(1990)-101088, JPA H2(1990)-235820, JPA H2(1990)-235821, JPA H3(1991)-20226, JPA H3(1991)-68591, JPA H3(1991)-148288 and U.S. Pat. Nos. 5,019,390, 5,135,935, WO9215579, W09309155 and W09313096.

And, various compounds showing antifungal action by inhibiting the synthesis of squalene have been known (JPA H4(1992)-279589, EP-475706, EP-494622, EP-503520, among others).

In reference to 2-oxo-2,3,4,5-tetrahydro-1H-[1]-benzazepine derivatives, disclosure is found in J. Med. Chem., 14, 849(1971), Chem. Pharm. Bull., 38, 3331(1990), J. Chem. Soc. PERKIN TRANS. 1, 353 (1991) and J. Med. Chem., 14, 40(1971).

In reference to 2-oxo-1,2,3,5-tetrahydro-4,1-benzothiazepine derivatives, disclosure is found in J. Prakt. Chem., 36, 5(1967), Arch. Pharm. 300, 299(1967) and U.S. Pat. No. 3463774.

2,3-Dihydro-2-oxo-1H-1,4-benzodiazepine derivatives, in which the the 3-position is occupied with an alkyl group substituted with ester, carboxylic acid or carbamoyl, and, further, the 5-position is occupied with an aryl group are disclosed in J. Heterocycl. Chem. 27, 631(1990), JPA S63(1988)-246666, Bull. Chim. Farm., 113, 642(1974), J. Chem. Soc., Chem. Commun., 1973, 721, J. Org. Chem., 38, 3502(1973) and Journal of the Takeda Research Laboratories, 29, 134(1970).

In reference to 2-oxo-2,3,5,6-tetrahydro-1H-4,1-benzoxazocine derivatives, disclosure is found in Chem. Pharm. Bull., 34(1), 140(1986).

In reference to 2,4-dioxo-2,3,4,5-tetrahydro-1H-1,5-benzodiazepine derivatives, disclosure is found in "Heterocyclic Compounds" ed by R. Ian Fryer (1991) John Wiley & Sons, Inc. p.p 289–313.

In reference to 2-oxo-1,2-dihydro-3H-1,3,4-benzotriazepine derivatives, disclosure is found in Japanese published examined patent application No. S45-11148/1970 (JPB S45(1970)-11148).

In reference to 2-oxo-1,2,4,5-tetrahydro-3H-1,3-benzodiazepine derivatives, disclosure is found in J. Chem. Soc., Perkin Trans. 1(12), 1331 (1976) and French Patent No. 2528838.

OBJECT OF THE INVENTION

Ubiquinone, dolichol and heme A have been known as being synthesized from farnesyl pyrophosphate along the cholesterol biosynthesis pathway. Therefore, for avoiding occurrence of side effects due to loss of these substances, it is desirable to inhibit enzyme systems subsequent to farnesyl pyrophosphate, especially squalene synthetase, in the cholesterol biosynthetic pathway.

SUMMARY OF THE INVENTION

The present inventors have, taking the above-mentioned circumstances into consideration, made diligent research work, and found that the condensed cyclic compounds have an excellent action of inhibiting squalene synthetase, thus the present invention being accomplished.

More specifically, the present invention is to provide (1) A compound of the formula (I):

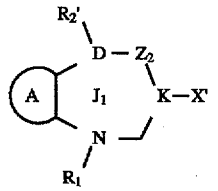

(I)

wherein $R_1$ is hydrogen or an optionally substituted hydrocarbon group; $R_2'$ is an optionally substituted phenyl group or an optionally substituted aromatic heterocyclic ring group; X' is a substituent comprising an optionally esterified carboxyl group, an optionally substituted carbamoyl group, an optionally substituted hydroxyl group, an optionally substituted amino group or an optionally substituted heterocyclic radical having a protonizable hydrogen; Ring A is an optionally substituted benzene ring or an optionally substituted aromatic heterocyclic ring; Ring $J_1$ is a 7-membered heterocyclic ring containing at most three ring constituting hetero atoms; D is C or N; $Z_1$ is C, N, $S(O)_q$ (q=0, 1 or 2) or O; K is C or N; the ring $J_1$ optionally having, besides $R_1$, $R_2'$ and X', a further substituent, provided that the condensed ring composed of Ring A and Ring $J_1$ is not 2-oxo-1,2,3,5-tetrahydro-4,1-benzoxazepine ring, 2-oxo-(2,3-dihydro or 2,3,4,5-tetrahydro)-1H-1,4-benzodiazepine ring or 2,4-dioxo-2,3,4,5-tetrahydro-1H-1,5-benzodiazepine ring, or a salt thereof, (2) The compound or the salt thereof as mentioned in the item (1), in which the compound is represented by the formula (I'):

(I')

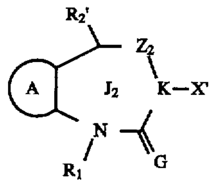

wherein $R_1$ is hydrogen or an optionally substituted hydrocarbon group; $R_2$' is an optionally substituted phenyl group or an optionally substituted aromatic heterocyclic ring group; X' is a substituent comprising an optionally esterified carboxyl group, an optionally substituted carbamoyl group, an optionally substituted hydroxyl group, an optionally substituted amino group or an optionally substituted heterocyclic radical having a protonizable hydrogen; Ring A is an optionally substituted benzene ring or an optionally substituted aromatic heterocyclic ring; Ring $J_2$ is a 7-membered heterocyclic ring; $Z_2$ is $S(O)_q$ (q=0, 1 or 2), C or O; K is C or N; G is O or S, provided that the condensed ring composed of Ring A and Ring $J_2$ is not 2-oxo-1,2,3,5-tetrahydro-4,1-benzoxazepine ring, or a salt thereof, (3) A squalene synthetase inhibitor which comprises the compound represented by the formula (I'')

(I'')

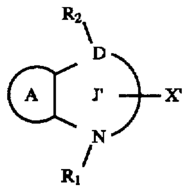

wherein $R_1$ is hydrogen or an optionally substituted hydrocarbon group; $R_2$ is hydrogen, an optionally substituted alkyl group, an optionally substituted phenyl group or an optionally substituted aromatic heterocyclic ring group; X' is a substituent comprising an optionally esterified carboxyl group, an optionally substituted carbamoyl group, an optionally substituted hydroxyl group, an optionally substituted amino group or an optionally substituted heterocyclic radical having a protonizable hydrogen; Ring A is an optionally substituted benzene ring or an optionally substituted aromatic heterocyclic ring; Ring J' is a 7- to 8-membered heterocyclic ring containing at most three ring constituting hetero atoms; D is C or N; the Ring J' optionally having, besides $R_1$, $R_2$ and X', a further substituent; provided that the condensed ring composed of Ring A and ring J' is not a 2-oxo-1,2,3,5-tetrahydro-4,1-benzoxazepine ring, or a pharmaceutically acceptable salt thereof, and (4) The inhibitor as mentioned in the item (3), in which the compound is represented by the formula (I''')

(I''')

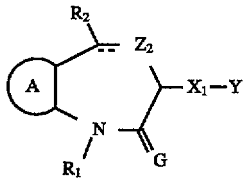

wherein $R_1$ is hydrogen or an optionally substituted hydrocarbon group; $R_2$ is hydrogen, an optionally substituted alkyl group, an optionally substituted phenyl group or an optionally substituted aromatic heterocyclic ring group; $X_1$ is a bond or a divalent atomic chain; Y is an optionally esterified carboxyl group, an optionally substituted carbamoyl group, an optionally substituted hydroxyl group, an optionally substituted amino group or an optionally substituted heterocyclic radical having protonizable hydrogen; Ring A is an optionally substituted benzene ring or an optionally substituted aromatic heterocyclic ring; $Z_3$ is =N—, —N($R_7$)— (wherein $R_7$ stands for H, alkyl group or acyl group), —S—, —S(O)—, —S($O_2$)—, —$CH_2$— or —O— is O or S; the symbol ......... is a double bond when $Z_3$ is =N—, while a single bond when $Z_3$ is not =N—, provided that, when $Z_3$ is —O— and Ring A is an optionally substituted benzene ring, G is S, or a pharmaceutically acceptable salt thereof.

Further, the present invention is to provide a method of producing a novel compound represented by the formula (I) or a salt thereof.

DETAILED DESCRIPTION OF THE INVENTION

In the above formulae (I), (I'), (I'') and (I'''), as the hydrocarbon group of the "optionally substituted hydrocarbon groups" shown by $R_1$, mention is made of aliphatic chain-like hydrocarbon groups, alicyclic hydrocarbon groups and aryl groups, etc., among them, aliphatic chain-like hydrocarbon groups being preferable.

As the aliphatic chain-like hydrocarbon groups of said hydrocarbon groups, mention is made of, for example, straight-chain or branched aliphatic hydrocarbon groups, such as alkyl group, alkenyl group, alkynyl group, etc., among them, alkyl groups being preferable. As the alkyl group, mention is made of, for example, $C_{1-7}$ alkyl such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, etc., and, among them, $C_{3-5}$ alkyl groups such as n-propyl, isopropyl, isobutyl, neopentyl, etc. are preferable, further, isobutyl, neopentyl being preferable. As the said alkenyl group, mention is made of, for example, $C_{2-6}$ alkenyl such as vinyl, allyl, isopropenyl, 2-methylallyl, 1-propenyl, 2-methyl-1-propenyl, 2-methyl-2-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc., and, among them, vinyl, allyl, isopropenyl, 2-methylallyl, 2-methyl-1-propenyl, 2-methyl-2-propenyl, 3-methyl-2-butenyl, etc. are especially preferable. As the said alkynyl group, mention is made of, for example, $C_{2-6}$ alkynyl such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc., and, among them, ethynyl, 1-propynyl, 2-propynyl, etc. are especially preferable.

Examples of the alicyclic hydrocarbon groups of said hydrocarbon group include saturated or unsaturated alicyclic hydrocarbon groups such as cycloalkyl group, cycloalkenyl group, cycloalkadienyl group, etc. As said cycloalkyl group, $C_{3-9}$ cycloalkyl groups are preferable, for example, cyclopropyl, cyclobutyl, cyclopentyl, cyclohexyl, cycloheptyl, cyclooctyl, cyclononyl, etc. are mentioned, and, among them, $C_{3-6}$ cycloalkyl groups such as cyclopropyl, cyclobutyl, cyclopentyl, cyclohexyl, etc. are preferable. As said cycloyalkenyl group, mention is made of, for example, 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc. As said cycloalkadienyl group, mention is made of, for example, 2,4-cyclopentadien-1-yl, 2,4-cyclohexadien-1-yl, 2,5-cyclohexadien-1-yl, etc.

As the aryl group of said hydrocarbon group, mention is made of mono-cyclic or condensed polycyclic aromatic hydrocarbon groups, for example, phenyl, naphthyl, anthryl, phenanthryl, acenaphthylenyl, etc., and, among them, phenyl, 1-naphthyl, 2-naphthyl, etc. are especially preferable.

As substituents of the "optionally substituted hydrocarbon groups" shown by $R_1$, mention is made of optionally substituted aryl groups, optionally substituted cycloalkyl groups or cycloalkenyl groups, optionally substituted heterocyclic groups, optionally substituted amino groups, optionally substituted hydroxyl groups, optionally substituted thiol groups, halogen (e.g. fluorine, chlorine, bromine, iodine), oxo, etc., and, the hydrocarbon group shown by $R_1$ is optionally substituted with 1 to 5 (preferably 1 to 3) of these substituents at any possible position. As aryl groups of said optionally substituted aryl groups, mention is made of phenyl, naphthyl, anthryl, phenanthryl, acenaphthylenyl, etc., and, among them, phenyl, 1-naphthyl and 2-naphthyl are preferable. As substituents of said optionally substituted aryl, mention is made of $C_{1-3}$ alkoxy groups (e.g. methoxy, ethoxy, propoxy, etc.), halogen atoms (e.g. fluorine, chlorine, bromine, iodine), $C_{1-3}$ alkyl groups (e.g. methyl, ethyl, propyl, etc.), and the aryl is optionally substituted with one or two of optional ones of them. As cycloalkyl groups of said optionally substituted cycloalkyl groups, mention is made of $C_{3-7}$ cycloalkyl groups including cyclopropyl, cyclobutyl, cyclopentyl, cyclohexyl, cycloheptyl, etc. The kinds and number of the substituents of said optionally substituted cycloalkyl groups are substantially the same as those in the case of the above-mentioned aryl groups. As cycloalkenyl groups of said optionally substituted cycloalkenyl groups, mention is made of, among others, $C_{3-6}$ cycloalkenyl groups such as cyclopropenyl, cyclobutenyl, cyclopentenyl, cyclohexenyl, etc. The kinds and number of the substituents of said optionally substituted cycloalkenyl groups are substantially the same as those in the case of the above-mentioned optionally substituted aryl groups. As heterocyclic groups of said optionally substituted heterocyclic groups, mention is made of, aromatic heterocyclic groups having, as the atoms (cyclic atoms) constituting the cyclic system, at least one hetero-atom selected from oxygen, sulfur and nitrogen, and saturated or unsaturated non-aromatic heterocyclic groups (aliphatic heterocyclic groups), preferably aromatic heterocyclic groups. As said aromatic heterocyclic groups, mention is made of aromatic mono-cyclic heterocyclic groups (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, triazinyl, etc.) and aromatic condensed heterocyclic groups (e.g. benzofuranyl, isobenzofuranyl, benzo[b] thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.), and, among them, furyl, thienyl, indolyl, isoindolyl, pyrazinyl, pyridyl, pyrimidinyl, etc. are preferable. Examples of said non-aromatic heterocyclic groups include oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc. As substituents of said optionally substituted heterocyclic groups, mention is made of $C_{1-3}$ alkyl groups (e.g. methyl, ethyl, propyl, etc.). Examples of substituents of said optionally substituted amino groups, optionally substituted hydroxyl groups and optionally substituted thiol groups include lower ($C_{1-3}$) alkyl (e.g. methyl, ethyl, propyl, etc.). And, when the hydrocarbon groups in the optionally substituted hydrocarbon groups shown by $R_1$ are alicyclic hydrocarbon groups or aryl group, they may have, as substituents, $C_{1-3}$ alkyl groups (e.g. methyl, ethyl, propyl, etc.).

Further, examples of $R_1$ include optionally substituted $C_{1-6}$ acyl groups such as formyl, acetyl, propionyl, butyryl, isobutyryl, valeryl, isovaleryl, pivaloyl, hexanoyl, dimethylacetyl, trimethylacetyl, etc. Said acyl group may have one to five appropriate substituents at any possible positions. Such substituents include halogen atoms (e.g. fluorine, chlorine, bromine).

In the formulae (I), (I'), (I") and (I"'), as the substituents of the "optionally substituted phenyl groups" shown by $R_2$ or $R_2'$, mention is made of halogen (e.g. fluorine, chlorine, bromine, iodine), an optionally substituted lower alkyl, an optionally substituted lower alkoxy, an optionally substitued hydroxyl group, nitro, cyano, etc., and the phenyl group may be preferably substituted with 1 to 3 (preferably 1 to 2) of these substituents at any possible position. As the lower alkyl, mention is made of, for example, $C_{1-4}$ alkyl groups including methyl, ethyl, n-propyl, isopropyl, n-butyl, isobutyl, sec-butyl, tert-butyl, etc., and especially methyl and ethyl are preferable. As the lower alkoxy, mention is made of $C_{1-4}$ alkoxy groups including methoxy, ethoxy, n-propoxy, isopropoxy, n-butoxy, isobutoxy, sec-butoxy, tert-butoxy, etc., and especially methoxy and ethoxy are preferable. As substituents of said optionally substituted lower alkyl groups or optionally substituted lower alkoxy groups, mention is made of halogen atoms (e.g. fluorine, chlorine, bromine, iodine, etc.), and one to five of these-may optionally substituted at an optional possible position. As substituents at said optionally substituted hydroxyl group, mention is made of, for example, $C_{1-4}$ alkyl groups (e.g. methyl, ethyl, propyl, isopropyl, butyl, t-butyl, etc.), $C_{3-6}$ cycloalkyl groups (cyclopropyl, cyclobutyl, cyclopentyl, cyclohexyl, etc.), aryl groups (e.g. phenyl, 1-naphthyl, 2-naphthyl, etc.), aralkyl groups (e.g. benzyl, phenethyl, etc.) These substituents may form a ring taken together with the adjacent substituents to each other, for example, such rings as shown by

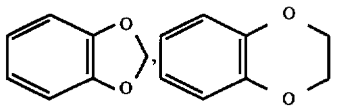

are mentioned. Said ring may be substituted with a lower ($C_{1-3}$) alkyl (e.g. methyl, ethyl, propyl, isopropyl, etc.) and the like.

As aromatic heterocyclic groups of the "optionally substituted aromatic heterocyclic groups" shown by $R_2$ or $R_2'$, mention is made of aromatic heterocyclic groups described in detail referring to $R_1$, and, among them, furyl, thienyl, indolyl, isoindolyl, pyrazinyl, pyridyl, pyrimidyl, imidazolyl, etc. are preferable. As substituents of said aromatic heterocyclic groups, mention is made of $C_{1-3}$ alkyl groups (e.g. methyl, ethyl, propyl, etc.).

In the formula (I") and (I'"), as the alkyl groups of optionally substituted alkyl groups" shown by $R_2$, mention is made of $C_{1-6}$ lower alkyl groups (e.g. methyl, ethyl, n-propyl, isopropyl, butyl, isobutyl, sec-butyl, tert-butyl, pentyl, isopentyl, neopentyl, hexyl, isohexyl, etc.), and, among them, $C_{1-4}$ alkyl groups including methyl, ethyl, propyl, isopropyl, butyl and t-butyl are preferable. As the substituents of said optionally substituted alkyl groups, mention is made of halogen (e.g. fluorine, chlorine, bromine, iodine), $C_{1-4}$ lower alkoxy groups (e.g. methoxy, ethoxy, propoxy, isopropoxy, butoxy, t-butoxy, etc.).

Among the above-exemplified groups represented by $R_2$ or $R_2'$, optionally substituted phenyl groups, preferably substituted phenyl groups are preferable, with greater preference given to a phenyl group substituted with halogen, lower alkoxy, etc. In the above formulae (I), (I') and (I"), as the "a substituent comprising an optionally esterified carboxyl group" shown by X', mention is made of optionally esterified carboxyl groups and a substituent having an optionally esterified carboxyl group, etc. Said optionally esterified carboxyl groups are substantially the same as those in the case of the below-mentioned optionally esterified carboxyl groups shown by Y.

As the "a substituent comprising an optionally substituted carbamoyl group" shown by X', mention is made of optionally substituted carbamoyl groups and a substituent having an optionally substituted carbamoyl group, etc. Said optionally substituted carbamoyl groups are substantially the same as those in the case of the below-mentioned optionally substituted carbamoyl groups shown by Y.

As the "a substituent comprising an optionally substituted hydroxyl group" shown by X', mention is made of optionally substituted hydroxyl groups and a substituent having an optionally substituted hydroxyl group, etc. Said optionally substituted hydroxyl groups are substantially the same as those in the case of the below-mentioned optionally substituted hydroxyl groups shown by Y.

As the "a substituent comprising an optionally substituted amino group" shown by X', mention is made of optionally substituted amino groups and a substituent having an optionally substituted amino group, etc. Said optionally substituted amino groups are substantially the same as those in the case of the below-mentioned optionally substituted amino groups shown by Y.

As the "substituent comprising an optionally substituted heterocyclic radical having a protonizable hydrogen" shown by X', mention is made of an optionally substituted heterocyclic radical having a protonizable hydrogen and a substituent having an optionally substituted heterocyclic radical having a protonizable hydrogen, etc. Said optionally substituted heterocyclic radicals are substantially the same as those in the case of the below-mentioned optionally substituted heterocyclic radicals shown by Y.

Examples of X' include groups represented by the formula (a)

$$\overline{\cdots\cdots\cdots}X-Y$$

wherein X is a bond or a divalent or trivalent atomic chain; Y is an optionally esterified carboxyl group, an optionally substituted carbamoyl group, an optionally substituted hydroxyl group, an optionally substituted amino group or an optionally substituted heterocyclic radical having a protonizable hydrogen; the symbol $\overline{\cdots\cdots\cdots}$ is a single or double bond.

In the formula (a), as the "divalent atomic chain" shown by X, mention is made of, preferably, any one of divalent chains having 1 to 7 atoms, more preferably 1 to 4, constituting the straight-chain, and they may have side chains.

For example, mention is made of chains represented by the formula $$-(CH_2)_m-E-(\overset{R_4}{\overset{|}{C}H})_n-$$

wherein m and n independently denote 0, 1, 2 or 3; E stands for a bond or oxygen atom, sulfur atom, sulfoxide, sulfone, $-N(R_3)-$, $-NHCO-$, $-CON(R_5)-$ or $-NHCONH-$; herein $R_4$ and $R_5$ stands for H, an optionally substituted lower alkyl group, an optionally substituted aralkyl group or an optionally substituted phenyl group; and $R_3$ stands for H, a lower alkyl group, aralkyl group or acyl group.

As the alkyl groups of the "optionally substituted lower alkyl groups" shown by $R_4$ and $R_5$, mention is made of $C_{1-6}$ straight-chain or branched lower alkyl groups (e.g. methyl, ethyl, n-propyl, isopropyl, n-butyl, isobutyl, tert-butyl, n-pentyl, isopentyl, neopentyl, etc.). As substituents of the said optionally substituted lower alkyl groups, mention is made of aromatic heterocyclic groups (e.g. furyl, thienyl, indolyl, isoindolyl, pyrazinyl, pyridyl, pyrimidyl, imidazolyl, etc.), an optionally substituted amino group, an optionally substituted hydroxyl group, an optionally substituted thiol group, an optionally esterified carboxyl group, halogen atoms (e.g. fluorine, chlorine, bromine, iodine), etc. As substituents of said optionally substituted amino group, optionally substituted hydroxyl group and optionally substituted thiol group, mention is made of a lower ($C_{1-3}$)alkyl (e.g. methyl, ethyl, propyl, etc.), or the like. Examples of the said optionally esterified carboxyl groups include methoxycarbonyl, ethoxycarbonyl, propoxycarbonyl, phenoxycarbonyl, 1-naphthoxycarbonyl, etc., preferably methoxycarbonyl, ethoxycarbonyl and propoxycarbonyl.

As aralkyl groups of the "optionally substituted aralkyl groups" shown by $R_4$ and $R_5$, mention is made of benzyl, naphthylmethyl, phenylpropyl, phenylbutyl, etc. As substituents of said optionally substituted aralkyl groups, mention is made of halogen atoms (e.g. fluorine, chlorine, bromine, iodine), $C_{1-3}$ alkoxy groups (e.g. methoxy, ethoxy, propoxy group), hydroxyl group, amino group, carboxyl group, sulfhydryl group, etc.

As substituents of the "optionally substituted phenyl groups" shown by $R_4$ and $R_5$, mention is made of halogen atoms (e.g. fluorine, chlorine, bromine, iodine), $C_{1-3}$ alkoxy (e.g. methoxy, ethoxy, propoxy, etc.), $C_{1-3}$ alkyl (e.g. methyl, ethyl, propyl) etc.

Provided that, $R_4$ may be different in each chain.

And, as the "lower alkyl groups" and "aralkyl groups" shown by $R_3$, mention is made of $C_{1-4}$ lower alkyl groups (e.g. methyl, ethyl, propyl, butyl, tert-butyl, etc.), $C_{7-15}$ aralkyl groups (e.g. benzyl, phenethyl, phenylpropyl, phenylbutyl, naphthylmethyl, etc.).

As the "acyl group" shown by $R_3$, mention is made of lower alkanoyl groups (e.g. formyl, acetyl, propionyl, butyryl, isobutyryl, valeryl, isovaleryl, pivaloyl, hexanoyl, etc.), lower alkenoyl groups (e.g. acryloyl, methacryloyl, crotonoyl, isocrotonoyl, etc.), cycloalkanecarbonyl groups (e.g. cyclopropanecarbonyl group, cyclobutanecarbonyl group, cyclopentanecarbonyl group, cyclohexanecarbonyl group, etc.), lower alkanesulfonyl groups (e.g. mesyl, ethanesulfonyl, propanesulfonyl, etc.), aroyl groups (e.g. benzoyl, p-toluoyl, 1-naphthoyl, 2-naphthoyl, etc.), aryl lower alkanoyl groups (e.g. phenylacetyl, phenylpropionyl, hydroatropoyl, phenylbutyryl, etc.), aryl lower alkenoyl groups (e.g. cynnamoyl, atropoyl, etc.), arenesulfonyl groups (e.g. benzenesulfonyl, p-toluenesulfonyl, etc.), etc.

In additions, as X, mention is made of a carbon chain containing a double bond or —L—C(OH)— (wherein L is a bond or a straight-chain or branched alkylene chain). As said "carbon chain containing double bond", mention is made of, preferably, those in which the carbon number constituting the straight-chain portion ranges from 1 to 7, more preferably 1 to 4, and they may optionally have a side chain. While the double bond at said carbon chain is contained in the straight-chain portion and/or branched chain portion, it is contained preferably in the straight-chain portion. Number of the double bond contained in said carbon chain is not restricted as far as possible, it ranges preferably from 1 to 2.

Examples of carbon chains containing said double bond include methine, vinylene, propenylene, butenylene, butadienylene, methylpropenylene, ethylpropenylene, propylpropenylene, methylbutenylene, ethylbutenylene, propylbutenylene, methylbutadienylene, ethylbutadienylene, propylbutadienylene, pentenylene, hexenylene, heptenylene, hexadienylene and heptadienylene, preferably methine, vinylene, propenylene, butenylene and butadienylene. Herein, when said carbon chain is trivalent, it binds to a carbon atom on Ring $J_1$, $J_2$ or J' at any possible position by a double bond.

Examples of the "straight-chain or branched alkylene chain" shown by L include straight-chain or branched $C_{1-6}$ alkylene chain, more specifically, divalent ones such as methylene, ethylene, trimethylene, tetramethylene, pentamethylene, hexamethylene, propylene, ethylmethylene, ethylethylene, propylethylene, butylethylene, methyltetramethylene and methyltrimethylene, and, preferably, $C_{1-3}$ ones such as methylene, ethylene, trimethylene and propylene.

Among the above-exemplified groups shown by X', the groups represented by the formula (b)

$$—X_1—Y$$

wherein $X_1$ is a bond or a divalent atomic chain; Y is an optionally esterified carboxyl group, an optionally substituted carbamoyl group, an optionally substituted hydroxyl group, an optionally substituted amino group or an optionally substituted heterocyclic radical having a protonizable hydrogen, are preferable.

In the formula (b), the "divalent atomic chains" shown by $X_1$ are substantially the same as those in the case of the above-mentioned divalent atomic chains shown by X.

In the formulae (a) and (b), as the "divalent atomic chain" shown by X or $X_1$, more preferably, mention is made of straight-chain or branched alkylene chain, in which the carbon number constituting the straight-chain ranges from 1 to 7 (preferably from 1 to 4). Examples of said alkylene chain include divalent ones such as methylene, ethylene, trimethylene, tetramethylene, pentamethylene, hexamethylene, heptamethylene, propylene, ethylmethylene, ethylethylene, propylethylene, butylethylene, methyltetramethylene and methyltrimethylene, and, preferably $C_{1-4}$ ones such as methylene, ethylene, trimethylene and propylene.

In the formulae (a) and (b), as the "optionally esterified carboxyl groups" shown by Y, mention is made of lower alkoxycarbonyl (e.g. methoxycarbonyl, ethoxycarbonyl, propoxycarbonyl, isopropoxycarbonyl, butoxycarbonyl, tert-butoxycarbonyl, sec-butoxycarbonyl, pentyloxycarbonyl, isopentyloxycarbonyl, neopentyloxycarbonyl, etc.), aryloxycarbonyl (e.g. phenoxycarbonyl, 1-naphthoxycarbonyl, benzyloxycarbonyl, etc.). Among them, carboxyl group, methoxycarbonyl and ethoxycarbonyl are preferable.

Examples of substituents of the "optionally substituted carbamoyl group" shown by Y include optionally substituted lower ($C_{1-6}$) alkyl (e.g. methyl, ethyl, n-propyl, isopropyl, butyl, isobutyl, sec-butyl, tert-butyl, pentyl, isopentyl, neopentyl, hexyl, isohexyl, etc.), optionally substituted $C_{1-3}$ cycloalkyl groups (e.g. cyclopropyl, cyclobutyl, cyclopentyl, cyclohexyl, etc.), optionally substituted aryl group (e.g. phenyl, 1-naphthyl, 2-naphthyl, etc.), optionally substituted aralkyl groups (e.g. benzyl, phenethyl, etc.), and, one or two of these substituents may independently substituted. As substituents at said optionally substituted lower ($C_{1-6}$) alkyl and optionally substituted $C_{3-6}$ cycloalkyl group, mention is made of, carboxyl group optionally esterified with a lower ($C_{1-5}$) alkyl (e.g. methyl, ethyl, propyl, isopropyl, butyl, t-butyl, pentyl, isopentyl, neopentyl, etc.), aromatic heterocyclic groups (e.g. furyl, thienyl, indolyl, isoindolyl, pyrazinyl, pyridyl, pyrimidyl, imidazolyl, etc.), amino group, hydroxyl group, phenyl group, etc., and, one to three of these substituents may independently substituted. As substituents of said optionally substituted aryl groups and optionally substituted aralkyl groups, mention is made of, halogen atoms (e.g. fluorine, chlorine, bromine, iodine), carboxyl groups optionally esterified with a lower ($C_{1-4}$) alkyl (e.g. methyl, ethyl, propyl, isopropyl, butyl, t-butyl, etc.). And, two substituents on a nitrogen atom may form a cyclic amino group taken together with the nitrogen atom. Examples of such cyclic amino group include 1-azetidinyl, 1-pyrrolidinyl, piperidino, morpholino, 1-piperazinyl, etc.

Examples of substituents of the "optionally substituted hydroxyl groups" shown by Y include lower ($C_{1-4}$) alkyl (e.g. methyl, ethyl, propyl, isopropyl, butyl, t-butyl, etc.), $C_{3-6}$ cycloalkyl groups (e.g. cyclopropyl, cyclobutyl, cyclopentyl, cyclohexyl, etc.), optionally substituted aryl groups (e.g. phenyl, 1-naphthyl, 2-naphthyl, etc.), optionally substituted aralkyl groups (e.g. benzyl, phenethyl, etc.), etc. As substituents of said optionally substituted aryl group and optionally substituted aralkyl group, mention is made of halogen atoms (e.g. fluorine, chlorine, bromine, iodine), carboxyl groups optionally esterified with lower ($C_{1-4}$) alkyl (e.g. methyl, ethyl, propyl, isopropyl, butyl, t-butyl, etc.), etc.

Examples of substituents of the "optionally substituted amino groups" shown by Y include lower ($C_{1-4}$) alkyl (e.g. methyl, ethyl, propyl, isopropyl, butyl, t-butyl, etc.), $C_{3-6}$ cycloalkyl groups (e.g. cyclopropyl, cyclobutyl, cyclopentyl, cyclohexyl, etc.), optionally substituted aryl groups (e.g. phenyl, 1-naphthyl, 2-naphthyl, etc.), optionally substituted aralkyl groups (e.g. benzyl, phenethyl, etc.), etc. As substituents of said optionally substituted aryl group and optionally substituted aralkyl group, mention is made of halogen atoms (e.g. fluorine, chlorine, bromine, iodine), carboxyl groups optionally esterified with lower ($C_{1-4}$) alkyl (e.g. methyl, ethyl, propyl, isopropyl, butyl, t-butyl, etc.), etc. And, two substituents on a nitrogen atom may form a cyclic amino group taken together with the nitrogen atom. Examples of the cyclic amino group include 1-azetidinyl, 1-pyrrolidinyl, piperidino, morpholino, 1-piperazinyl, etc. As heterocyclic radicals of the "optionally substituted heterocyclic radical having a protonizable hydrogen" shown by Y, mention is made of 5–7 membered (preferably 5 membered) monocyclic heterocyclic radical containing at least one hetero atom selected from the group consisting of N, S and O, more preferably N-containing heterocyclic radical. Especially, tetrazol-5-yl and groups represented by the formula

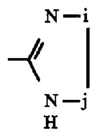

, wherein i stands for —O— or —S—; j stands for >C=O, >C=S or >$SO_2$ (especially 2,5-dihydro-5-oxo-1,2,4-oxadiazol-3-yl, 2,5-dihydro-5-thioxo-1,2,4-oxadiazol-3-yl, 2,5-dihydro-5-oxo-1,2,4-thiadiazol-3-yl) are preferable.

Said heterocyclic radical may be protected with an optionally substituted lower alkyl (preferably $C_{1-4}$ alkyl), acyl, etc. As said optionally substituted lower alkyls, mention is made of methyl, triphenylmethyl, methoxymethyl, ethoxymethyl, p-methoxybenzyl, p-nitrobenzyl, etc. Examples of said acyl include lower ($C_{2-5}$) alkanoyl, benzoyl, etc.

Among the above-exemplified groups shown by X', an alkyl group substituted with an optionally esterified carboxyl group or an alkyl group substituted with an optionally substituted heterocyclic radical having a protonizable hydrogen are preferable.

In the formulae (I), (I'), (I") and (I'''), as aromatic heterocyclic rings shown by ring A, mention is made of aromatic heterocyclic groups described in detail referring to $R_1$. Among them, groups represented by the formulae

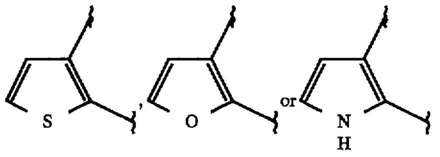

are preferable.

As substituents of the "optionally substituted benzene rings" and "optionally substituted aromatic heterocyclic groups", mention is made of halogen (e.g. fluorine, chlorine, bromine, iodine), $C_{1-4}$ optionally substituted lower alkyl groups (e.g. methyl, ethyl, propyl, butyl, tert-butyl, etc.), $C_{1-4}$ optionally substituted lower alkoxy groups (methoxy, ethoxy, propoxy, isopropoxy, butoxy, tert-butoxy, etc.), nitro group, cyano, etc. the ring A may have 1 to 3 of these substituents, preferably 1 to 2. And, these substituents may form a ring, taken together with respectively adjacent substituents. As substituents of said optionally substituted lower alkyl groups or those of optionally substituted lower alkoxy groups, mention is made of halogen atoms (e.g. fluorine, chlorine, bromine, iodine), etc., which may have 1 to 3 substituents at optional positions. As rings A, those which are substituted with methoxy or chlorine atom are preferable, especially those substituted with chlorine are preferable.

In the formula (I), as heterocyclic rings of the "7-membered heterocyclic ring containing at most three ring constituting hetero atoms" shown by ring $J_1$, mention is made of saturated or unsaturated 7-membered heterocyclic rings containing, as the atoms constituting the cyclic ring, at least one hetero-atom selected from O, $S(O)_q$ (q is 0, 1 or 2) and N, provided that the number of hetero atoms in the atoms constituting the cyclic system (ring constituting atoms) of said heterocyclic ring is at most three.

And, the ring $J_1$ may optionally have, besides the groups represented by $R_2$, $R_2'$ and X', one or two appropriate substituents at any possible position. As said substituent, when it binds to a nitrogen atom on the ring $J_1$ ($Z_1$ is N), mention is made of $C_{1-6}$ straight-chain or branched alkyl groups (e.g. methyl, ethyl, n-propyl, isopropyl, n-butyl, isobutyl, tert-butyl, n-pentyl, isopentyl, neopentyl, etc.), acyl groups such as $C_{1-4}$ acyl groups (e.g. formyl, acetyl, propionyl, butyroyl, etc.), etc. Said alkyl or said acyl may have one to five of halogen atoms (e.g. fluorine, chlorine, bromine, iodine). And, when said substituent binds to a carbon atom or the ring $J_1$, mention is made of oxo, thioxo, an optionally substituted hydroxyl group, an optionally substituted amino group, etc. Said optionally substituted hydroxyl group and said optionally substituted amino group are substantially the same as the "optionally substituted hydroxyl group and the "optionally substituted amino group shown by Y.

The ring $J_1$ is preferably substituted with oxo or thioxo, besides the groups of $R_1$, $R_2'$ and X', at any possible position.

D, as the atom constituting the cyclic ring (ring constituting atom), is preferably C. And, K, as ring constituting atom, is preferably C.

As the condensed ring composed of Ring A and Ring $J_1$, mention is made of

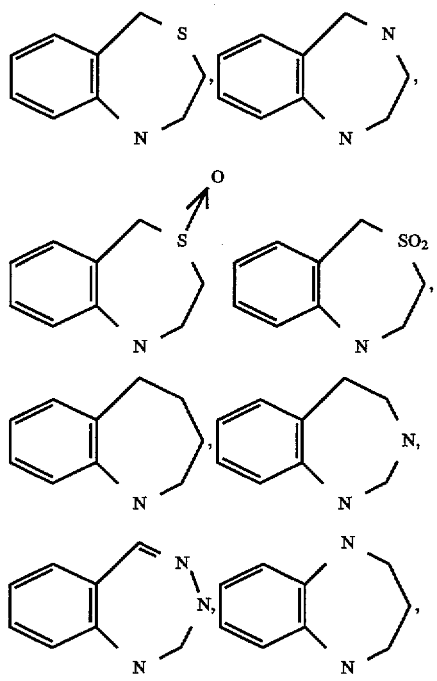

-continued

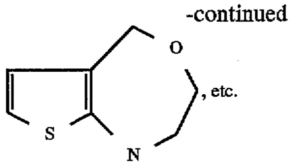

The formula (I) is preferably one represented by the formula (I').

In the formula (I'), as 7-membered heterocyclic rings shown by ring $J_2$, mention is made of saturated 7-membered heterocyclic rings containing, as the atoms constituting the cyclic ring, at least one hetero atom selected from O, $S(O)_q$ (q is 0, 1 or 2) and N.

$Z_2$, as ring constituting atom, is preferably $S(O)_q$ (q is 0, 1 or 2). K, as ring constituting atom, is preferably C.

In the formula (I'), G is more preferably O.

In addition, as the formula (I'), one represented by the following formula

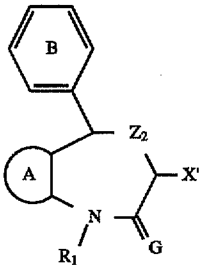

wherein $R_1$, X', ring A, $Z_2$ and G are substantially of the same meaning as above mentioned; Ring B is a substituted phenyl group, provided that, when $Z_2$ is —O— and Ring A is an optionally substituted benzene ring, G is S, is preferable.

Examples of substituents of the "substituted phenyl group" shown by ring B are substantially the same as those in the case of the above mentioned substituents of the "optionally substituted phenyl group" shown by $R_2$'.

In the formula (I"), as heterocyclic rings of the "7- or 8-membered heterocyclic ring containing at most three ring constituting hetero atoms" shown by ring J', mention is made of saturated or unsaturated 7- or 8-membered heterocyclic rings containing, as the atoms constituting the cyclic ring, at least one hetero-atom selected from O, $S(O)_q$ (q is 0, 1 or 2) and N, provided that the number of hetero atoms in the atoms constituting the cyclic system (ring constituting atoms) of said heterocyclic ring is at most three.

And, the ring J' may optionally have, besides the groups represented by $R_1$, $R_2$ and X', one or two appropriate substituents at any possible position. As said substituent, when it binds to a nitrogen atom on the ring J', mention is made of $C_{1-6}$ straight-chain or branched alkyl groups (e.g. methyl, ethyl, n-propyl, isopropyl, n-butyl, isobutyl, tert-butyl, n-pentyl, isopentyl, neopentyl, etc.), acyl groups such as $C_{1-4}$ acyl groups (e.g. formyl, acetyl, propionyl, butyroyl, etc.), etc. Said alkyl or said acyl may have one to five of halogen atoms (e.g. fluorine, chlorine, bromine, iodine). And, when said substituent binds to a carbon atom or the ring J', mention is made of oxo, thioxo, an optionally substituted hydroxyl group, an optionally substituted amino group, etc. Said optionally substituted hydroxyl group and said optionally substituted amino group are substantially the same as the "optionally substituted hydroxyl group and the "optionally substituted amino group shown by Y.

The ring J' is preferably substituted with oxo or thioxo, besides the groups of $R_1$, $R_2$ and X', at any possible position.

As the condensed ring composed of Ring A and Ring J', mention is made of

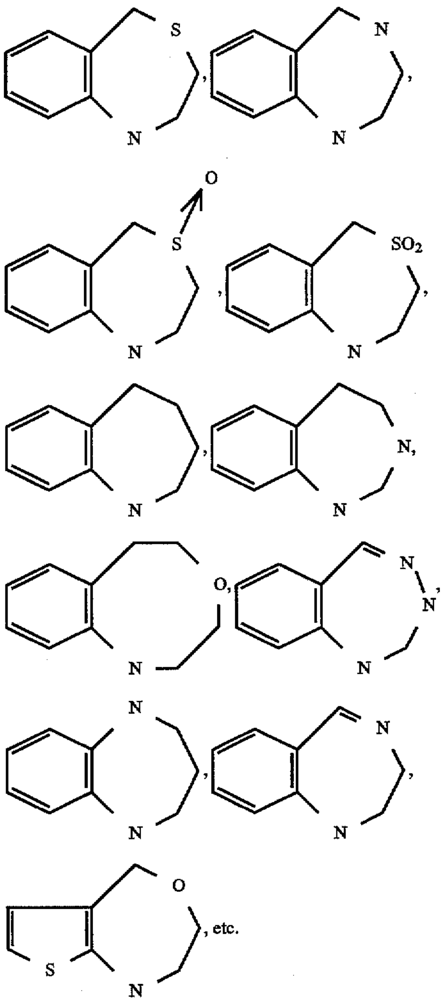

D, as ring constituting atom, is preferably C.

The formula (I") is preferably one represented by the formula (I"').

$Z_3$ is preferably $S(O)_q$ (q is 0, 1 or 2). G is more preferably O.

In the formulae (I"'), as alkyl groups shown by $R_7$, mention is made of $C_{1-6}$ straight-chain or branched lower alkyl groups (e.g. methyl, ethyl, n-propyl, isopropyl, n-butyl, isobutyl, tert-butyl, n-pentyl, isopentyl, neopentyl, etc.), which may optionally be substituted with 1 to 5 halogen atoms (e.g. fluorine, chlorine, bromine, iodine).

As acyl groups shown by RT, mention is made of $C_{1-4}$ acyl groups (e.g. formyl, acetyl, propionyl, butyroyl, etc.), which may optionally be substituted with 1 to 5 halogen atoms (e.g. fluorine, chlorine, bromine, iodine).

The compounds of this invention are specifically disclosed as follows:

3,5-cis-7-Chloro-5-(2-chlorophenyl)-1-neopentYl-2-oxo-1,2,3,5-tetrahydro-4,1-benzothiazepine-3-acetic acid methyl ester, 3,5-trans-7-Chloro-5-(2-chlorophenyl)-1-neopentyl-2-oxo-1,2,3,5-tetrahydro-4,1-benzothiazepine-3-acetic acid methyl ester, 3,5-trans-7-Chloro-5-(2-chlorophenyl)-1-propyl-2-oxo-1,2,3,5-tetrahydro-4,1-benzothiazepine-3-acetic acid methyl ester, 3,5-trans-7-Chloro-5-(2-chlorophenyl)-1-isobutyl-2-oxo-1,2,3,5-tetrahydro-4,1-benzothiazepine-3-acetic acid methyl ester, 3,5-trans-7-Chloro-5-(2-methoxyphenyl)-2-oxo-1-propyl-1,2,3,5-tetrahydro-4,1-benzothiazepine-3-acetic acid methyl ester, 3,5-trans-7-Chloro-5-(2-methoxyphenyl)-1-neopentyl-2-oxo-1,2,3,5-tetrahydro-4,1-benzothiazepine-3-acetic acid methyl ester, 3,5-trans-7-Chloro-5-(2-methoxyphenyl)-1-isobutyl-2-oxo-1,2,3,5-tetrahydro-4,1-benzothiazepine-3-acetic acid methyl ester, 3,5-trans-7-Chloro-5-(2-chlorophenyl)-1-neopentyl-2-oxo-1,2,3,5-tetrahydro-4,1-benzothiazepine-3-acetic acid, 3,5-trans-7-Chloro-5-(2-chlorophenyl)-1-isobutyl-2-oxo-1,2,3,5-tetrahydro-4,1-benzothiazepine-3-acetic acid, 3,5-trans-7-Chloro-5-(2-methoxyphenyl)-1-neopentyl-2-oxo-1,2,3,5-tetrahydro-4,1-benzothiazepine-3-acetic acid, 3,5-trans-7-Chloro-5-(2-methoxyphenyl)-1-isobutyl-2-oxo-1,2,3,5-tetrahydro-4,1-benzothiazepine-3-acetic acid, (3R)-7-Chloro-5-(2-chlorophenyl)-2,3-dihydro-1-isobutyl-2-oxo-1H-1,4-benzodiazepine-3-acetic acid methyl ester, (3R)-7-Chloro-5-(2-chlorophenyl)-2,3-dihydro-1-isobutyl-2-oxo-1H,1,4-benzodiazepine-3-acetic acid, (3R,5S)-7-Chloro-5-(2-chlorophenyl)-2,3,4,5-tetrahydro-1-isobutyl-2-oxo-1H-1,4-benzodiazepine-3-acetic acid, (3S)-7-Chloro-5-(2-chlorophenyl)-2,3-dihydro-1-isobutyl-2-oxo-1H-1,4-benzodiazepine-3-acetic acid methyl ester, (3S)-7-Chloro-5-(2-chlorophenyl)-2,3-dihydro-1-isobutyl-2-oxo-1H-1,4-benzodiazepine-3-acetic acid, N-[3,5-trans-7-Chloro-5-(2-chlorophenyl)-1-neopentyl-2-oxo-1,2,3,5-tetrahydro-4,1-benzothiazepin-3-acetyl] glycine methyl ester N-[3,5-trans-7-Chloro-5-(2-chlorophenyl)-1-neopentyl-2-oxo-1,2,3,5-tetrahydro-4,1-benzothiazepin-3-acetyl] glycine, 3,5-trans-7-Chloro-5-(2-chlorophenyl)-3-dimethylaminocarbonylmethyl-1-neopentyl-2-oxo-1,2,3,5-tetrahydro-4,1-benzothiazepine, 7-Chloro-5-(2-chlorophenyl)-1-isobutyl-2-oxo-2,3,4,5-tetrahydro-1H-[1]-benzazepine-3-acetic acid ethyl ester, 7-Chloro-5-(2-chlorophenyl)-1-isobutyl-2-oxo-2,3,4,5-tetrahydro-1H-[1]-benzazepine-3-acetic acid, 3,5-trans-7-Chloro-5-(2-chlorophenyl)-1-neopentyl-1,2,3,5-tetrahydro-2-thioxo-4,1-benzoxazepine-3-acetic acid ethyl ester, 3,5-trans-7-Chloro-5-(2-chlorophenyl)-1-neopentyl-1,2,3,5-tetrahydro-2-thioxo-4,1-benzoxazepine-3-acetic acid, 7-Chloro-5-(2-chlorophenyl)-1-neopentyl-2-oxo-1,2,3,5-tetrahydro-4,1-thieno[2,3-e]oxazepine-3-acetic acid ethyl ester, 3,5-trans-7-Chloro-5-(2-chlorophenyl)-1-neopentyl-2-oxo-1,2,3,5-tetrahydro-4,1-thieno[2,3-e]oxazepine-3-acetic acid, 3,5-trans-7-Chloro-5-(2-methoxyphenyl)-1-neopentyl-2-oxo-1,2,3,5-tetrahydro-4,1-thieno[2,3-e]oxazepine-3-acetic acid ethyl ester, 3,5-cis-7-Chloro-5-(2-methoxyphenyl)-1-neopentyl-2-oxo-1,2,3,5-tetrahydro-4,1-thieno[2,3-e]oxazepine-3-acetic acid ethyl ester, 3,5-trans-7-Chloro-5-(2-methoxyphenyl)-1-neopentyl-2-oxo-1,2,3,5-tetrahydro-4,1-thieno[2,3-e]oxazepine-3-acetic acid, 3,5-cis-7-Chloro-5-(2-methoxyphenyl)-1-neopentyl-2-oxo-1,2,3,5-tetrahydro-4,1-thieno[2,3-e]oxazepine-3-acetic acid, 3,5-trans-7-Chloro-1-isobutyl-5-(2-methoxyphenyl)-2-oxo-1,2,3,5-tetrahydro-4,1-thieno[2,3-e]oxazepine-3-acetic acid ethyl ester, 3,5-cis-7-Chloro-1-isobutyl-5-(2-methoxyphenyl)-2-oxo-1,2,3,5-tetrahydro-4,1-thieno[2,3-e]oxazepine-3-acetic acid ethyl ester, 3,5-trans-7-Chloro-1-isobutyl-5-(2-methoxyphenyl)-2-oxo-1,2,3,5-tetrahydro-4,1-thieno[2,3-e]oxazepine-3-acetic acid, 3,5-cis-7-Chloro-1-isobutyl-5-(2-methoxyphenyl)-2-oxo-1,2,3,5-tetrahydro-4,1-thieno[2,3-e]oxazepine-3-acetic acid, 3,5-trans-7-Chloro-5-(2,3-dimethoxyphenyl)-1-neopentyl-2-oxo-1,2,3,5-tetrahydro-4,1-benzothiazepine-3-acetic acid, 3,5-trans-7-Chloro-5-(2,4-dimethoxyphenyl)-1-neopentyl-2-oxo-1,2,3,5-tetrahydro-4,1-benzothiazepine-3-acetic acid, 3,5-trans-7-Chloro-5-(2,3-dimethoxyphenyl)-1-isobutyl-2-oxo-1,2,3,5-tetrahydro-4,1-benzothiazepine-3-acetic acid, 3,5-trans-7-Chloro-5-(2,4-dimethoxyphenyl)-1-isobutyl-2-oxo-1,2,3,5-tetrahydro-4,1-benzothiazepine-3-acetic acid, 3,5-trans-7-Chloro-5-(3-hydroxy-2-methoxyphenyl)-1-neopentyl-2-oxo-1,2,3,5-tetrahydro-4,1-benzothiazepine-3-acetic acid, 3,5-trans-7-Chloro-5-(4-hydroxy-2-methoxyphenyl)-1-neopentyl-2-oxo-1,2,3,5-tetrahydro-4,1-benzothiazepine-3-acetic acid, 3,5-trans-7-Chloro-5-(3-hydroxy-2-methoxyphenyl)-1-isobutyl-2-oxo-1,2,3,5-tetrahydro-4,1-benzothiazepine-3-acetic acid, 3,5-trans-7-Chloro-5-(4-hydroxy-2-methoxyphenyl)-1-isobutyl-2-oxo-1,2,3,5-tetrahydro-4,1-benzothiazepine-3-acetic acid, 3,5-trans-7-Chloro-5-(3-ethoxy-2-methoxyphenyl)-1-neopentyl-2-oxo-1,2,3,5-tetrahydro-4,1-benzothiazepine-3-acetic acid, 3,5-trans-7-Chloro-5-(4-ethoxy-2-methoxyphenyl)-1-neopentyl-2-oxo-1,2,3,5-tetrahydro-4,1-benzothiazepine-3-acetic acid, 3,5-trans-7-Chloro-5-(3-ethoxy-2-methoxyphenyl)-1-isobutyl-2-oxo-1,2,3,5-tetrahydro-4,1-benzothiazepine-3-acetic acid, 3,5-trans-7-Chloro-5-(4-ethoxy-2-methoxyphenyl)-1-isobutyl-2-oxo-1,2,3,5-tetrahydro-4,1-benzothiazepine-3-acetic acid, 3,5-trans-7-Chloro-5-(2-chloro-3-methoxyphenyl)-1-neopentyl-2-oxo-1,2,3,5-tetrahydro-4,1-benzothiazepine-3-acetic acid, 3,5-trans-7-Chloro-5-(2-chloro-4-methoxyphenyl)-1-neopentyl-2-oxo-1,2,3,5-tetrahydro-4,1-benzothiazepine-3-acetic acid, 3,5-trans-7-Chloro-5-(2-chloro-3-methoxyphenyl)-1-isobutyl-2-oxo-1,2,3,5-tetrahydro-4,1-benzothiazepine-3-acetic acid, 3,5-trans-7-chloro-5-(2-chloro-4-methoxyphenyl)-1-isobutyl-2-oxo-1,2,3,5-tetrahydro-4,1-benzothiazepine-3-acetic acid, 3,5-trans-7-Chloro-5-(2-chloro-3-hydroxyphenyl)-1-neopentyl-2-oxo-1,2,3,5-tetrahydro-4,1-benzothiazepine-3-acetic acid, 3,5-trans-7-Chloro-5-(2-chloro-4-hydroxyphenyl)-1-neopentyl-2-oxo-1,2,3,5-tetrahydro-4,1-benzothiazepine-3-acetic acid, 3,5-trans-7-Chloro-5-(2-chloro-3-hydroxyphenyl)-1-isobutyl-2-oxo-1,2,3,5-tetrahydro-4,1-benzothiazepine-3-acetic acid, 3,5-trans-7-Chloro-5-(2-chloro-4-hydroxyphenyl)-1-isobutyl-2-oxo-1,2,3,5-tetrahydro-4,1-benzothiazepine-3-acetic acid, etc.

As salts of the compounds (I), (I'), (I") and (I'"), mention is made of, pharmaceutically acceptable ones, for example, inorganic salts such as hydrochloride, hydrobromide, sulfate, nitrate, phosphate, etc.; organic acid salts such as acetate, tartrate, citrate, fumarate, maleate, toluenesulfonate, methanesulfonate, etc.; metal salts such as sodium salt, potassium salt, calcium salt, aluminum salt, etc., and salts with a base such as triethylamine salt, guanidine salt, ammonium salt, hydrazine salt, quinine salt, cinchonine salt, etc.

The method of producing compounds of this invention is described as follows.

A compound represented by the formula (Ia)

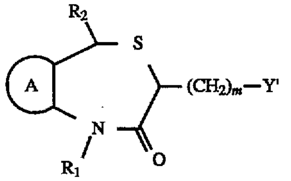

(Ia)

wherein Y' stands for an optionally esterified carboxyl group among those defined by Y, and other symbols are of the same meaning as defined above, can be produced by the following methods.

(Method A)

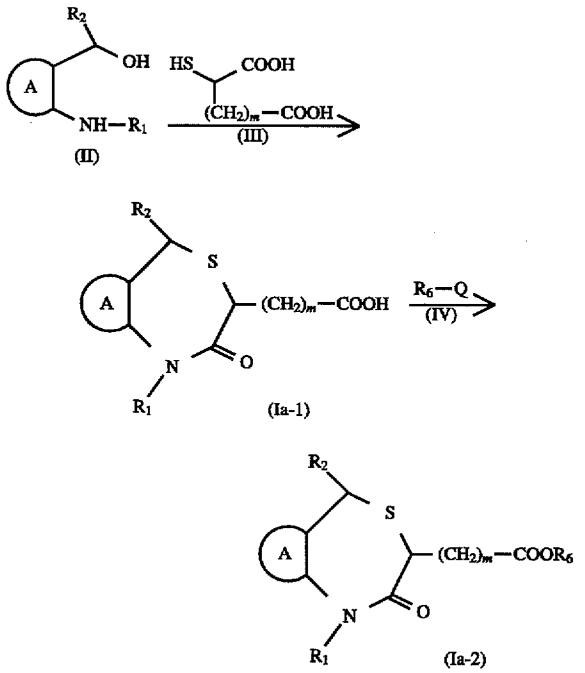

(II)

(Ia-1)

(Ia-2)

-continued (Method B)

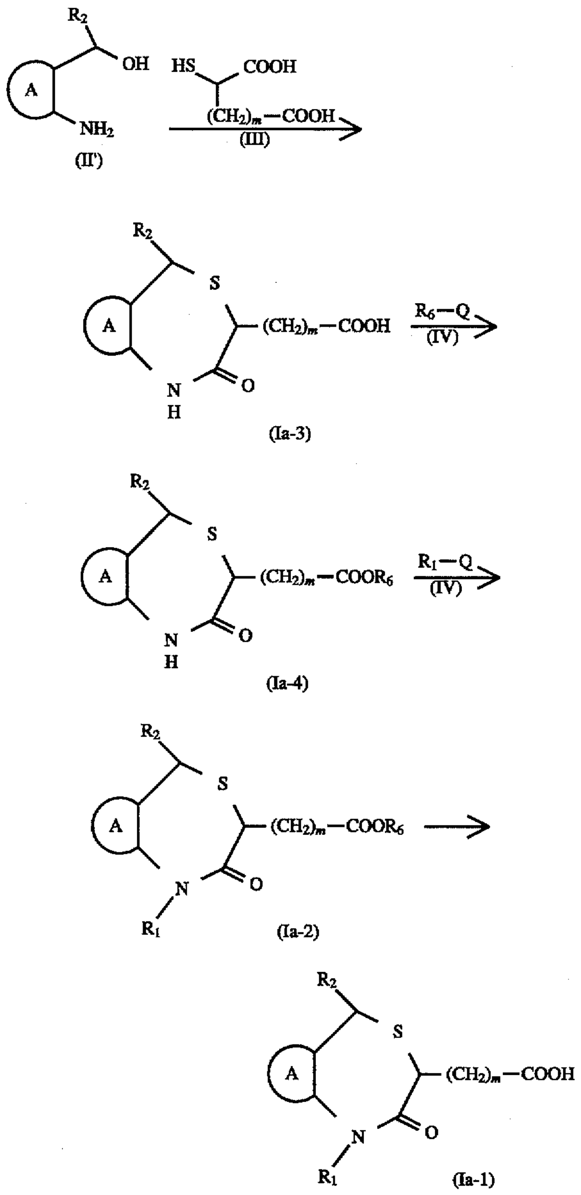

(II')

(Ia-3)

(Ia-4)

(Ia-2)

(Ia-1)

wherein $R_6$ stands for the alkyl portion of the esterified carboxyl group defined by Y', Q stands for halogen, and other symbols are of the same meaning as defined above].

Production of the formula (Ia-1) from the formula (II) in (Method A) and that of the formula (Ia-3) from the formula (II') in (Method B) can be conducted in a solvent, for example, an ether-type solvent such as diethyl ether, tetrahydrofuran, dioxane, etc., a hydrocarbon type solvent such as benzene, toluene, hexane, heptane, etc., an alcohol type solvent such as methanol, ethanol, propanol, butanol, etc.; acetone, dimethylformamide, dimethyl sulfoxide and acetic acid, and, when necessary, in the presence of an acid (hydrochloric acid, bromic acid, hydroiodic acid, sulfuric acid, phosphoric acid, methanesulfonic acid, toluenesulfonic acid). Relative to one mole of the compound represented by the formula (II) or (II'), the compound represented by the formula (III) is usually employed in an amount of 1 to 10 moles, preferably about 1 to 2 moles. The reaction temperature ranges from 0° to 200° C., preferably about 50° to 100°

C. The reaction time ranges usually from 1 to 24 hours, preferably about 1 to 3 hours.

The method of producing the formula (Ia-2) from the formula (Ia-4) in (Method B) can be conducted in a solvent, for example, an ether type solvent such as diethyl ether, tetrahydrofuran, dioxane, etc., a hydrocarbon type solvent such as benzene, toluene, hexane, heptane, etc., dimethylformamide or dimethyl sulfoxide, and, depending on necessity, in the presence of a base (e.g. sodium hydride, lithium hydride, etc.). Relative to one mole of the compound represented by the formula (Ia-4), a compound represented by the formula (V) is used, usually, in an amount ranging from 1 to 10 moles, preferably about 1 to 2 moles. The reaction temperature ranges from 0° to 200° C., preferably about 20° to 100° C. The reaction time ranges from 1 to 24 hours, preferable from about 1 to 5 hours.

The method of producing the formula (1a-2) from the formula (Ia-1) in (Method A) and that of producing (Ia-4) from the formula (Ia-3) in (Process B) can be conducted in a solvent, for example, water or an ether type solvent such as diethyl ether, tetrahydrofuran, dioxane, etc., a hydrocarbon type solvent such as benzene, toluene, hexane, heptane, etc., an alcohol type solvent such as methanol, ethanol, propanol, butanol, etc., acetone or dimethylformamide, and, depending on necessity, in the presence of a base (e.g. sodium hydrogencarbonate, potassium hydrogencarbonate, sodium carbonate, potassium carbonate, sodium hydride, potassium hydride, sodium hydroxide, potassium hydroxide, barium hydroxide, etc.). Relative to one mole of the compound represented by the formula (Ia-1) or the formula (Ia-3), a compound represented by the formula (IV) is employed, usually in an amount ranging from 1 to 10 moles, preferably from about 1 to 2 moles. The reaction temperature ranges from 0° to 100° C., preferably from about 25° to 50° C. The reaction time ranges usually from 1 to 24 hours, preferably from about 3 to 10 hours.

The method of producing the formula (Ia-1) from the formula (Ia-2) in (Method B) can be conducted in a solvent, for example, water or an ether type solvent such as diethyl ether, tetrahydrofuran, dioxane, etc., a hydrocarbon type solvent such as benzene, toluene, hexane, heptane, etc., an alcohol type solvent such as methanol, ethanol, propanol, butanol, etc., acetone or dimethylformamide, and, depending on necessity, in the presence of a base (e.g. sodium hydrogencarbonate, potassium hydrogencarbonate, sodium carbonate, potassium carbonate, sodium hydride, potassium hydride, sodium hydroxide, potassium hydroxide, barium hydroxide, etc.). The reaction temperature ranges from 0° to 100° C., preferably from about 20° to 50° C. The reaction time usually ranges from one to 24 hours, preferably about 3 to 10 hours.

A compound represented by the formula (Ib)

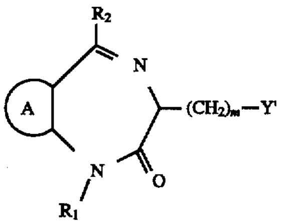

(Ib)

wherein symbols are of the same meaning as defined above, can be produced by the following methods.

(Method C)

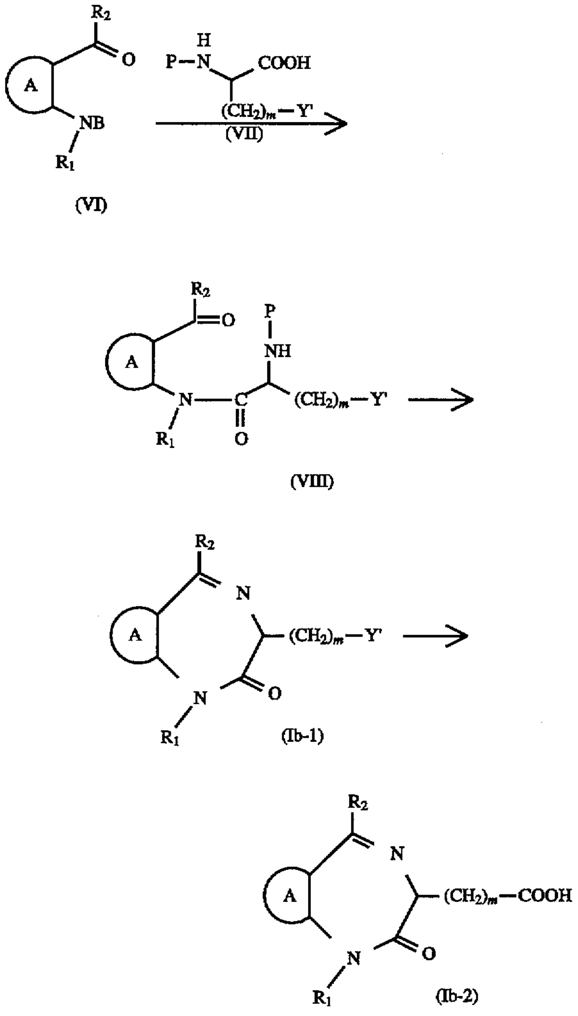

(VI) (VII) (VIII) (Ib-1) (Ib-2)

(Method D)

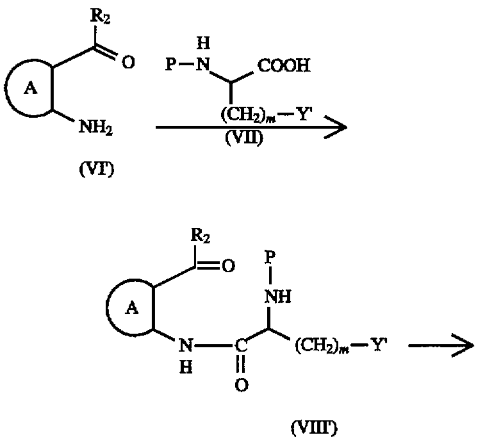

(VI') (VII) (VIII')

-continued

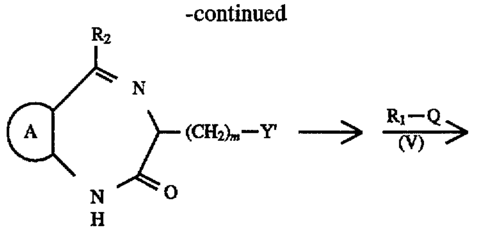

(Ib-3)

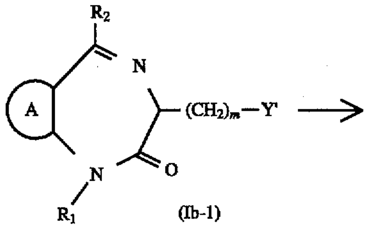

(Ib-1)

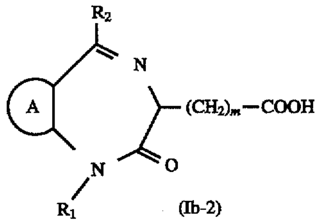

(Ib-2)

wherein P stands for an amine-protecting group such as a carbobenzyloxy group, a t-butyloxycarbonyl group, etc., and other symbols are of the same meaning as defined above.

In (Method C), (Method D), production of the formula (VIII) from the formula (VI) or of the formula (VIII') from the formula (VI') can be conducted in a solvent, for example, an ether type solvent such as diethyl ether, tetrahydrofuran, dioxane, etc., a hydrocarbon type solvent such as benzene, toluene, hexane, heptane, etc., and a halogen type solvent such as dichloromethane, chloroform, etc., acetonitrile or dimethylformamide using a condensing agent such as diethyl cyanophosphonate, dicyclohexylcarbodiimide, etc., and, depending on necessity, in the presence of a base (e.g. triethylamine, 4-dimethylaminopyridine, N-methylpiperidine, etc.). Relative to one mole of a compound represented by the formula (VI) or the formula (VI'), a compound represented by the formula (VII) is employed usually in an amount ranging from 1 to 5 moles, preferably from about 1 to 1.5 mole. The reaction temperature ranges from 0° to 100° C., preferably from about 20° to 50° C. The reaction time ranges from 1 to 24 hours, preferably from about 2 to 5 hours. In this case, the condensing agent is employed, relative to one mole of the compound represented by the formula (VI) or the formula (VI'), in an amount usually ranging from 1 to 5 moles, preferably from about 1 to 2 moles.

Production of the compound of the formula (Ib-1) from the compound of the formula (VIII) in (Method C) or that of the compound of the formula (Ib-3) from the formula (VIII') in (Method D) can be conducted, for example, in an ether-type solvent such as diethyl ether, tetrahydrofuran, dioxane, etc., a hydrocarbon type solvent such as benzene, toluene, hexane, heptane, etc., an alcohol type solvent such as methanol, ethanol, propanol, butanol, etc., acetone, dimethylformamide, acetonitrile solvent, a halogen type solvent such as dichloromethane, chloroform, etc., by a per se known method, for example, when P stands for a carbobenzyloxy group, catalytic reduction using palladium, platinum or the like as the catalyst, while, P stands for a t-butoxycarbonyl group, by subjecting the compound obtained by removing the amine-protecting group P by dissolving or suspending the compound in an acid (e.g. hydrochloric acid, bromic acid, trifluoroacetic acid) to catalytic reduction in, for example, an ether-type solvent such as diethyl ether, tetrahydrofuran, dioxane, etc., a hydrocarbon type solvent such as benzene, toluene, hexane, heptane, etc., an alcohol type solvent such as methanol, ethanol, propanol, butanol, etc., dimethylformamide, acetonitrile solvent, and, depending on necessity, in the presence of an acid (for example, hydrochloric acid, bromic acid, acetic acid, propionic acid, methanesulfonic acid, toluenesulfonic acid, sulfuric acid, etc.). The reaction temperature ranges from 0° to 100° C., preferably from about 30° to 70° C. The reaction time ranges usually from 1 to 24 hours, preferably from 3 to 10 hours.

Production of the compound of the formula (Ib-1) from the formula (Ib-3) in (Method D) can be conducted substantially the same method for producing the compound of the formula (Ia-2) from the compound of (Ia-4) in (Method B) for the production of the compound represented by the formula (Ia) as described in the foregoing. And, production of the compound represented by the formula (Ib-2) from the compound represented by the formula (Ib-1) in (Method C), and, that of the compound of the formula (Ib-2) from the compound represented by the formula (Ib-1) in (Method D) can be conducted by substantially the same method as that for producing the compound represented by the formula (Ia-1) from the compound represented by the formula (Ia-2) in (Method B) for the production of the compound represented by the formula (Ia) described in the foregoing.

A compound represented by the formula (Ic)

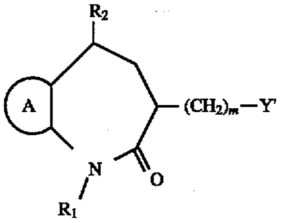

(Ic)

wherein symbols are of the same meaning as defined above, can be produced by the following methods.

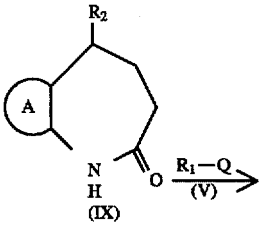

(IX)

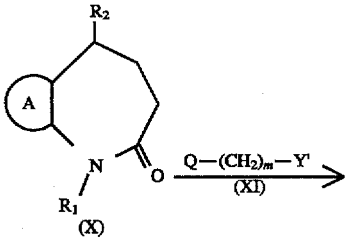

(X)

-continued

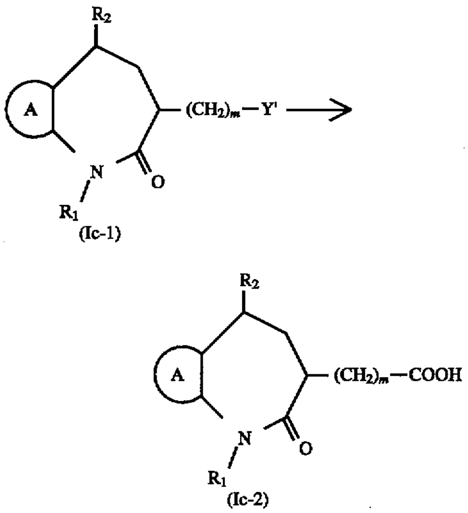

(Ic-1)

(Ic-2)

wherein symbols are of the same meaning as defined above.

Production of the compound (X) from the compound (IX) obtained by a method substantially in accordance with the methods disclosed in J. Med. Chem., 27, 1508(1984), J. Med. Chem., 14, 851 (1971), can be conducted in substantially the same manner as in the method of producing the compound represented by the formula (Ia-2) from the compound represented by the formula (Ia-4) in (Method B) for the production of the compound represented by the formula (Ia). Production of the compound represented by the formula (Ic-1) from the compound represented by the formula (X) can be conducted, in a solvent, for example, an ether type solvent such as diethyl ether, tetrahydrofuran, dioxane, etc., a hydrocarbon type solvent such as benzene, toluene, hexane, heptane, etc., dimethylformamide or dimethyl sulfoxide, in the presence of sodium hydride, lithium hydride, lithium diisopropylamide, etc. Relative to one mole of the compound represented by the formula (X), the compound represented by the formula (XI) is usually employed in an amount ranging from 1 to 5 moles, preferably about 1 to 2 moles. The reaction temperature ranges from −78° C. to 50° C., preferably from −78° C. to 0° C. The reaction time ranges usually from one to 24 hours, preferably about 3 to 10 hours. Production of the compound represented by the formula (Ic-2) from the compound represented by the formula (Ic-1) is conducted in substantially the same manner as in the production of the compound represented by the formula (Ia-1) from the compound represented by the formula (Ia-2) in (Method B).

A compound represented by the the formula (Id)

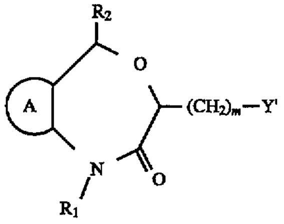

(Id)

wherein symbols are of the same meaning as defined above can be produced by the following methods.

[Method E]

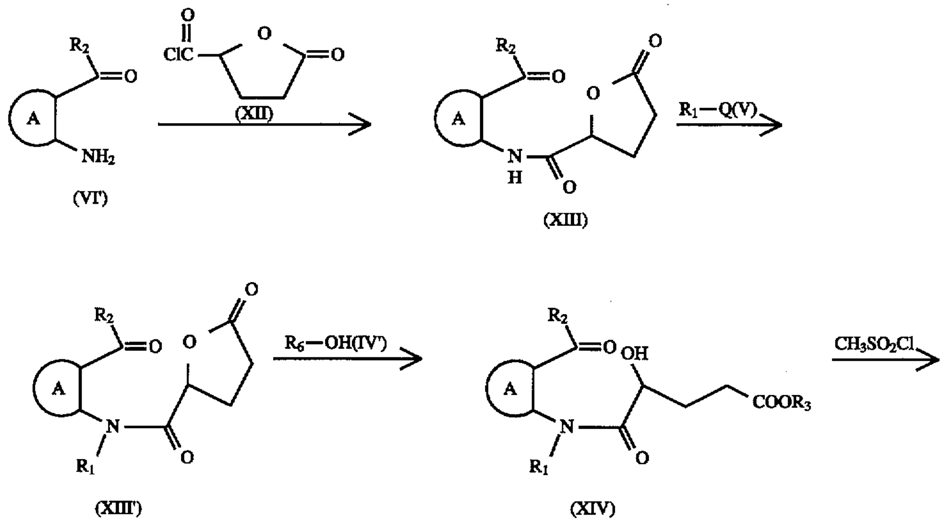

(VI')

(XIII)

(XIII')

(XIV)

-continued
[Method E]
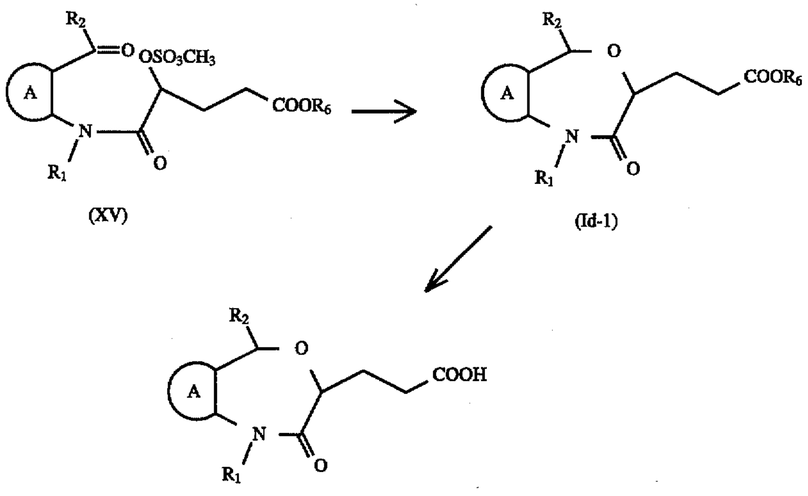
(XV) (Id-1) (Id-4)
[Method F]
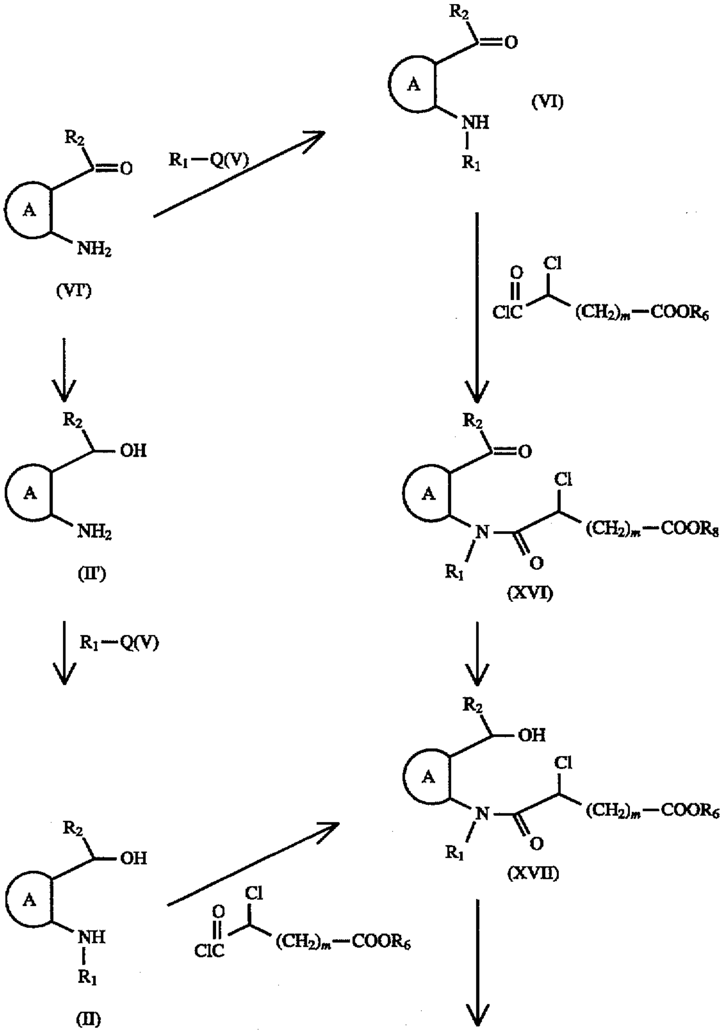
(VI') (VI) (II') (XVI) (XVII) (II)

-continued
[Method F]
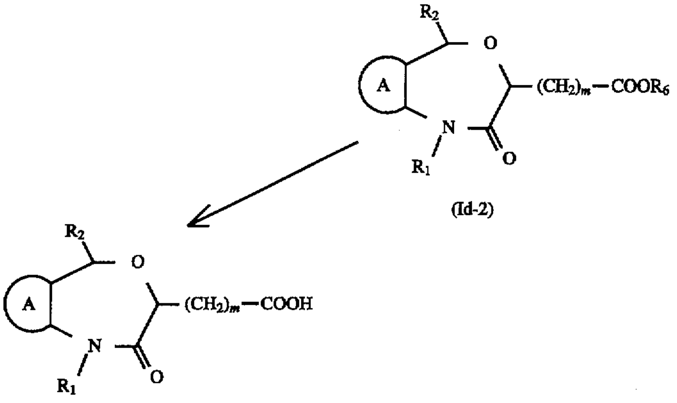
(Id-2)
(Id-4)
[Method G]
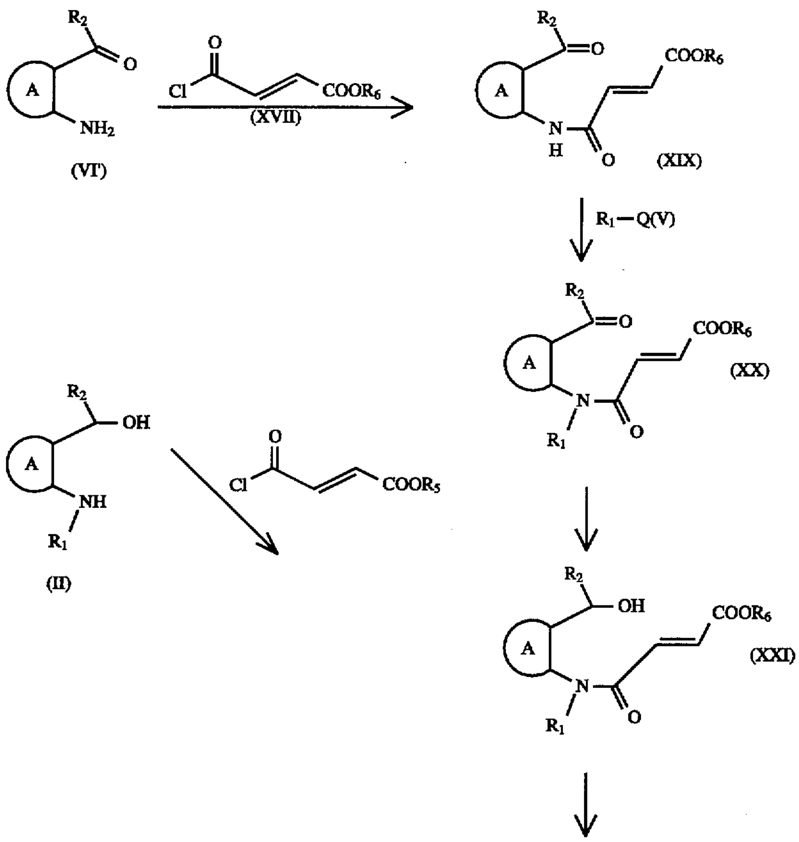
(VI) (XIX) (XX) (II) (XXI)

-continued

[Method G]

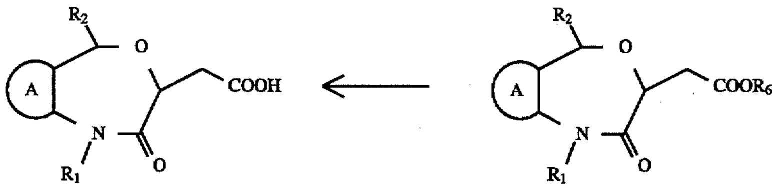

(Id-5) (Id-3)

wherein each symbol is of the same meaning as defined above.

Production of (XIII) from (VI'), (XV) from (XIV) in the above (Method E), or that of (XVI) from (VI), (XVII) from (II) in (Method F) can be conducted by utilizing a per se known acylation reaction. The acylation can be conducted in a solvent, for example, an ether-type solvent such as diethyl ether, tetrahydrofuran, dioxane, etc., a halogen type solvent such as dichloromethane, dichloroethane, chloroform, carbon tetrachloride, a hydrocarbon type solvent such as benzene, toluene, hexane, heptane, etc., dimethylformamide, dimethyl sulfoxide, etc., and, depending of necessity, in the presence of water and a base (e.g. an organic base such as 4-dimethyl aminopyridine, triethylamine, triethylenediamine, tetramethyl ethylenediamine, etc., sodium hydrogencarbonate, potassium hydrogencarbonate, sodium carbonate, potassium carbonate, sodium hydride, potassium hydride, etc.). Relative to one mole of the compound represented by the formula (VI'), (XIV), (VI) or (II), the amount of acid chloride or methanesulfonic chloride ranges usually from 1 to 10 moles, preferably from about 1 to 3 moles. The reaction temperature ranges from −50° to 100° C., preferably from about 0° to 50° C. The reaction time ranges usually from 1 to 48 hours, preferably from about 5 to 10 hours.

Production of (XIII') from (XIII) in the above-mentioned (Method E), that of (VI) from (VI') and that of (II) from (II') in (Method F) can be conducted in a solvent, for example, an ether type solvent such as diethyl ether, tetrahydrofuran, dioxane, etc., a hydrocarbon type solvent such as benzene, toluene, hexane, heptane, etc., an alcohol type solvent such as methanol, ethanol, propanol, etc., acetone, dimethylformamide, etc. and, depending on necessity, in the presence of a base (e.g. sodium hydrogencarbonate, potassium hydrogencarbonate, sodium carbonate, potassium carbonate, sodium hydride, potassium hydride, etc.). Relative to one mole of the compound represented by the formula (XIII), (VI') or (II'), the compound represented by the formula (V) is employed in an amount usually ranging from 1 to 10 moles, preferably from about 1 to 2 moles. The reaction temperature ranges from 0° to 100° C., preferably from about 20° to 50° C. The reaction time ranges usually from 1 to 24 hours, preferably from about 3 to 10 hours.

And, production of (Id-1) from (XV) in (Method E), that of (II') from (VI') and reduction of the carbonyl group of (XVII) from (XVI) in (Method F) can be conducted by processing with a metal hydrogen complex (e.g. lithium aluminum hydride, sodium aluminum hydride, sodium triethoxyaluminum hydride, sodium borohydride, etc.) in a protic solvent (methanol, ethanol, propanol, butanol, etc.) or an aprotic solvent (e.g. ethyl ether, tetrahydrofuran, dioxane, etc.). Relative to one mole of the compound represented by (XV), (VI') or (XVI), such a metal hydrogen complex is employed in an amount ranging usually from 0.3 to 5 moles, preferably from 0.5 to 2 moles. The reaction temperature ranges from −20° to 100° C., preferably from about 20° to 50° C.

Cyclization of (Id-2) from the formula (XVII) in (Method F) is conducted in a solvent, for example, an ether-type solvent such as diethyl ether, tetrahydrofuran, dioxane, etc., a hydrocarbon type solvent such as benzene, toluene, hexane, heptane, etc., an alcoholic solvent such as methanol, ethanol, propanol, butanol, etc., acetone, dimethylformamide, etc., and, depending on necessity, in the presence of a base (e.g. sodium hydrogencarbonate, potassium hydrogen carbonate, sodium carbonate, potassium carbonate, sodium hydride, potassium hydride, etc.). Relative to one mole of the compound represented by the formula (XVII), these bases are used usually in an amount ranging from one to 5 moles, preferably from about 1 to 2 moles. The reaction temperature ranges from −20° to 100° C. The reaction time usually ranges from 1 to 20 hours, preferably from about 2 to 5 hours.

The reaction to (XIV) from (XIII') in (Method E) can be conducted in alcohol represented by the formula (IV'), and, depending on necessity, in the presence of an inorganic acid such as nitric acid, hydrochloric acid, hydrobromic acid, sulfuric acid, etc., or an organic acid such as toluenesulfonic acid, methanesulfonic acid, etc. The reaction temperature ranges from −20° to 100° C., preferably from about 20° to 50° C. The reaction times ranges usually from 10 to 100 hours, preferably 10 to 48 hours.

Production of (Id-4) from (Id-1) in (Method E), and, that of (Id-4) from (Id-2) in (Method F) can be conducted in substantially the same manner as in the production of (Ia-1) from (Ia-2) in (Method B) in the synthesis of the compound represented by the formula (Ia).

Compounds represented by (Id-3) and (Id-5) in (Process G) can be produced in accordance with a per se known method.

A compound represented by the formula (Id')

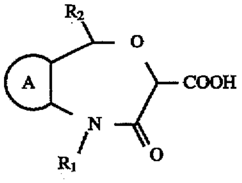

(Id')

wherein symbols are of the same meaning as defined above, can be produced by subjecting a compound represented by the formula (Ik')

(Ik')

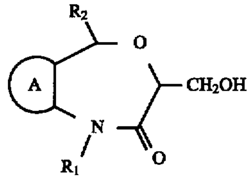

wherein symbols are of the same meaning as defined above, to oxidation. As the solvent to be then employed, any one can be used so long as it does not hamper the reaction, which is exemplified by acetone, dioxane, tetrahydrofuran, dichloromethane, dichloroethane, chloroform, etc., and as the oxidizing agent, use is made of permanganate, chromic acid, nickel peroxide, etc. Relative to one mole of the compound represented by the formula (Ik'), the oxidizing agent is employed in an amount ranging from 0.5 to 20 molar equivalents, preferably 1 to 3 molar equivalents. The reaction temperature ranges from 0° to 100° C., preferably from about 15° to 50° C. The reaction time ranges from 0.5 to 5 hours, preferably about 1 to 2 hours.

Those represented by the formula (Ie)

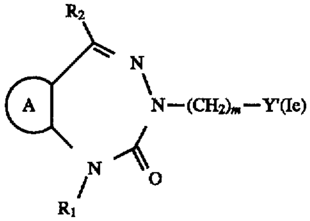

(Ie)

wherein symbols are of the same meaning as defined above, can be produced by the following method.

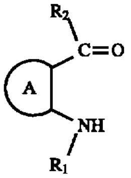

or (VI)

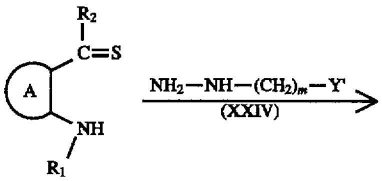

(XXII)

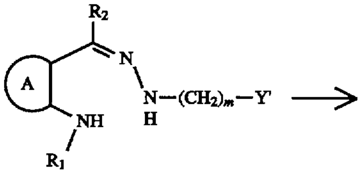

(XXIII)

-continued

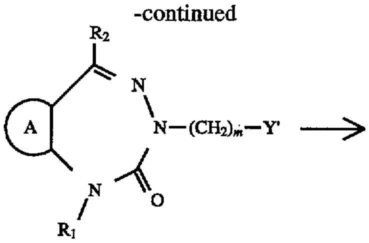

(Ie-1)

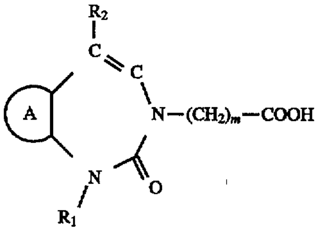

(Ie-2)

wherein symbols are of the same meaning as defined above.

The production of the compound of the formula (XXIII) from the compound of the formula (VI) or the formula (XXII) can be conducted by using, relative to one mole of the compound represented by the formula (VI) or the formula (XXII), usually 1 to 10 moles, preferably 1 to 2 moles, of the compound represented by the formula (XXIV) in, for example, an ether type solvent such as diethyl ether, tetrahydrofuran, dioxane, etc.; a hydrocarbon type solvent such as benzene, toluene, hexane or heptane; an alcohol type solvent such as methanol, ethanol, propanol, butanol, etc.; or a solvent such as dimethylformamide, dimethyl sulfoxide, etc. The reaction temperature ranges from 0° to 200° C., preferably from about 50° to 100° C. The reaction time ranges from 1 to 48 hours, preferably from about 10 to 24 hours.

The production of the compound of the formula (Ie) from the compound of the formula (XXIII) can be conducted by using, relative to one mole of the compound represented by the formula (XXIII), usually 1–10 moles, preferably 1 to 2 moles of a carbonylation agent including triphosgene, 1,1'-carbonyldiimidazole, 4-nitrophenyl, chloroformate or the like, in a solvent which does not hamper common reactions, for example, an ether type solvent such as diethyl ether, tetrahydrofuran or dioxane; a hydrocarbon type solvent such as benzene, toluene, hexane or heptane; an alcohol type solvent such as methanol, ethanol, propanol or butanol; a solvent such as dimethylformamide or dimethyl sulfoxide. The reaction temperature ranges from 0° to 200° C., preferably from about 50° to 100° C. The reaction time ranges from 0.5 to 24 hours, preferably from about 1 to 5 hours.

The compound represented by the formula (If)

(If)

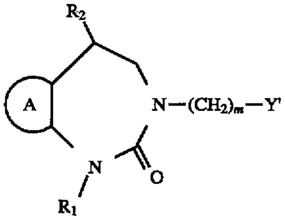

wherein symbols are of the same meaning as defined above, can be produced by the following method:

-continued

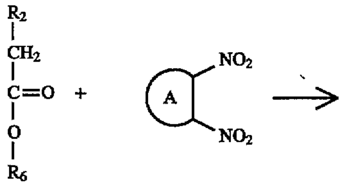

(XXV) (XXVI)

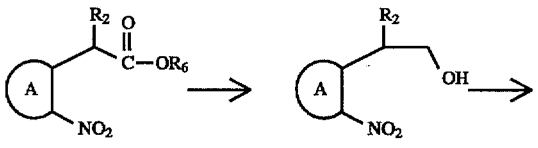

(XXVII) (XXVIII)

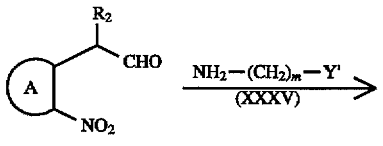

(XXIX)

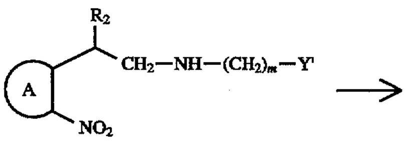

(XXX)

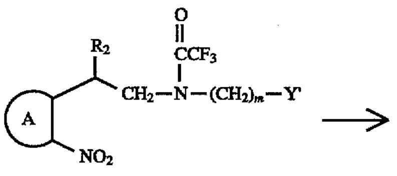

(XXXI)

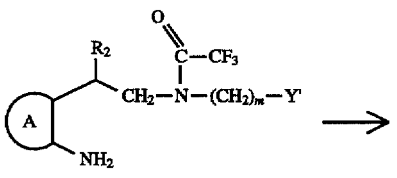

(XXXII)

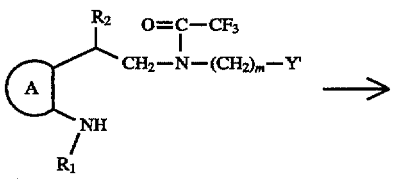

(XXXIII)

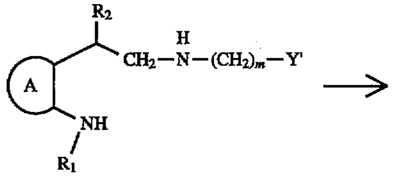

(XXXIV)

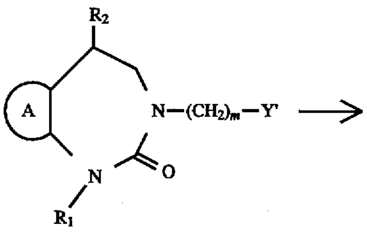

(If-1)

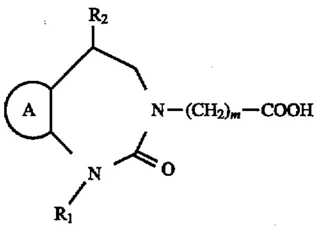

(If-2)

wherein symbols are of the same meaning as defined above.

Production of the compound represented by the formula (XXVII) from the compounds represented by the formula (XXV) and the formula (XXVI) can be conducted by using, relative to one mole of the compound represented by the formula (XXV), 1 to 5 molar equivalents, preferably 1 to 1.5 molar equivalents, of the compound represented by the formula (XXVI), in an ether type solvent such as dimethyl amide, ethyl ether, tetrahydrofuran, dioxane, etc., in the presence of sodium hydride, lithium hydride, alkyl lithium or the like. The reaction temperature ranges from −78° to 100° C., preferably from about −20° to 30° C. The reaction time ranges from 0.1 to 5 hours, preferably from about 0.5 to 2 hours.

Production of the compound represented by the formula (XXVIII) from the compound represented by the formula (XXVII) can be conducted by processing with a metal hydrogen complex compound (for example, lithium aluminum hydride, sodium aluminum hydride, sodium borohydride, lithium borohydride, etc.) in a solvent, for example, a protic solvent (methanol, ethanol, propanol, butanol, etc.) or an aprotic solvent (e.g. ethyl ether, tetrahydrofuran, dioxane, etc.). Such a metal hydrogen complex as above is usually employed, relative to one mole of the compound represented by the formula (XXVII), in an amount of 0.3 to 5 molar equivalents, preferably about 0.5 to 2 molar equivalents. The reaction temperature ranges from −20° to 100° C., preferably from about 0° to 20° C. The reaction time ranges usually from 0.5 to 10 hours, preferably 1 to 5 hours.

The compound represented by the formula (XXIX) can be produced by subjecting the compound represented by the formula (XXVIII) to oxidation. Solvents then to be employed may be any one so long as they do not hamper the reaction. For example, the compound can be produced by employing, for example, dimethyl sulfoxide and oxalyl chloride, or pyridine sulfur trioxide, in, for example, a solvent such as dioxane, tetrahydrofuran, dichloromethane, dichloroethane, chloroform or the like. In this case, relative to one mole of the compound represented by the formula (XXVIII), an oxidizing agent is employed in an amount of 0.5 to 20 molar equivalents, preferably 1 to 3 molar equivalents. The reaction time ranges from −78° to 50° C., preferably from −78° to 20° C. The reaction time ranges from 0.1 to 10 hours, preferably from about 0.2 to 2 hours. Depending on necessity, the reaction can be conducted in the presence of a base (e.g. 4-dimethylaminopyridine, triethylamine, triethylenediamine, tetramethylethylenediamine, etc.).

The compound represented by the formula (XXX) can be produced by subjecting the compound represented by the formula (XXIX) and the compound represented by the formula (XXXV) to reductive amination. For example, relative to one mole of the compound represented by the formula (XXIX), 0.5 to 10 molar equivalents, preferably 0.5 to 1.5 molar equivalent of the compound represented by the formula (XXXV) and 0.3 to 5 molar equivalents, preferably 0.5 to 1.5 molar equivalent of a metal hydrogen complex hydrogen (for example, sodium borohydride, lithium aluminum hydride, sodium cyanoborohydride, etc.) are employed in an ether type solvent such as diethyl ether, tetrahydrofuran, dioxane, etc.; a hydrocarbon type solvent such as benzene, toluene, hexane, heptane, etc.; or an alcohol type solvent such as methanol, ethanol, propanol, etc. The reaction temperature ranges from 0° to 100° C., preferably from about 30° to 60° C. The reaction time ranges usually from one to 24 hours, preferably from about 3 to 10 hours.

The compound represented by the formula (XXXI) can be produced by allowing the compound represented by the formula (XXX) to react with trifluoroacetic anhydride or trifluoroacetyl chloride. This reaction can be conducted by using, relative to one mole of the compound represented by the formula (XXX), 0.5 to 3 molar equivalents, preferably 1 to 2 molar equivalents of trifluoroacetic anhydride or trifluoroacetyl chloride, in an ether type solvent such as diethyl ether, tetrahydrofuran, dioxane, etc.; a hydrocarbon type solvent such as benzene, toluene, hexane, heptane, etc.; a halogen type solvent such as dichloromethane, dichloroethane, chloroform, etc.; or dimethylformamide, at temperatures ranging from 0° to 100° C., preferably from about 20° to 50° C., for about 5 minutes to 5 hours, preferably from about 0.1 to 1 hour. This production can be conducted, depending on necessity, in the presence of a base (e.g. an organic base such as 4-dimethyl aminopyridine, triethylamine, triethylenediamine, tetramethylethylenediamine, etc. or sodium hydrogencarbonate, potassium hydrogencarbonate, sodium carbonate, potassium carbonate, etc.).

The compound represented by the formula (XXXII) can be produced by subjecting the compound represented by the formula (XXXI) to catalytic hydrogenation using a palladium/carbon catalyst, in an alcohol type solvent such as methanol, ethanol, propanol, butanol, etc.; dimethylformamide, acetonitrile, acetic acid ethyl ester, etc. The hydrogen pressure ranges from 1 to 100 atmospheric pressure, preferably 1–10 atmospheric pressure, and the reaction temperature ranges from 0° to 200° C., preferably from about 20° to 50° C.

The compound represented by the formula (XXXIII) can be produced between the compound represented by the formula (XXXII) and a halogenated hydrocarbon group; or reductive amination reaction between aldehyde or ketone group. Conditions for the production are those substantially the same as in the production of (Ia-2) from (Ia-4) in (Method B) in the case of production of the compound represented by the afore-described formula (Ia) or those substantially the same as in the production of (XXX) from (XXIX) in the case of production of the compound represented by the formula (If).

Production of the compound represented by the formula (XXXIV) can be conducted by subjecting the compound represented by the formula (XXXIII) to hydrolysis in an alcohol type solvent such as methanol, ethanol, propanol, butanol, etc.; or an ether type solvent such as tetrahydrofuran, dioxane, etc.; in the presence of an acid such as hydrochloric acid, sulfuric acid, phosphoric acid, etc. The reaction temperature ranges from 0° to 100° C., preferably from 30° to 70° C., and the reaction time ranges from 1 to 48 hours, preferably from about 10 to 20 hours.

Production of the compound represented by the formula (If-1) from (XXXIV) can be conducted in substantially the same manner as in the method of producing (Ie-1) from (XXIII) in the case of producing the compound represented by the formula (Ie). And, production of the compound represented by the formula (If-2) from (If-1) can be conducted by substantially the same procedure as in the case of producing (Ia-1) from (Ia-2) in (Method B) for production of the compound represented by the formula (Ia).

The compound represented by the formula (Ig)

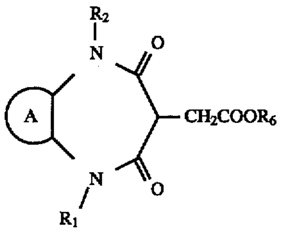

(Ig)

wherein symbols are of the same meaning as defined above, can be produced by the method described below.

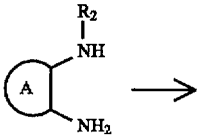

(XXXV)

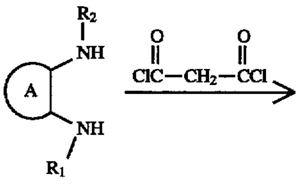

(XXXVI)

-continued

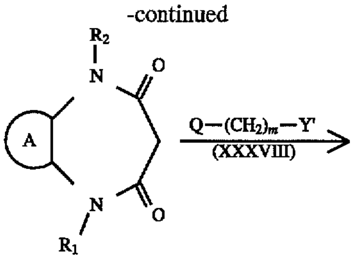

(XXXVII)

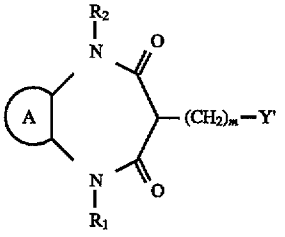

(Ig-1)

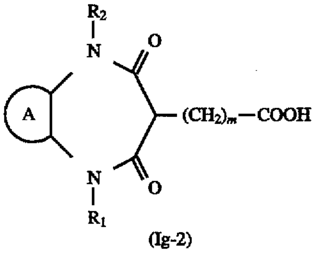

(Ig-2)

wherein symbols are of the same meaning as defined above.

The compound represented by the formula (XXXVI) can be produced in substantially the same manner as in the production of (Ia-2) from (Ia-4) in (Method B) in the case of producing the compound represented by the formula (Ia), or by reductive amination which is substantially the same as in the production of (XXX) from (XXIX) in the case of producing the compound represented by the formula (If).

Production of the compound represented by the formula (XXXVII) can be conducted by allowing the compound represented by the formula (XXXVI) to react with malonyl dichloride in, for example, an ether type solvent such as diethyl ether, tetrahydrofuran, dioxane, etc.; a halogen type solvent such as dichloromethane, chloroform, etc.; a solvent such as acetic acid ethyl ester, acetonitrile, water, etc. Relative to one mole of the compound (XXXVI), malonyl dichloride is employed in an amount ranging from 1 to 10 molar equivalents, preferably from about 1 to 2 molar equivalents. The reaction temperature ranges from −20° to 100° C., preferably from 0° to 70° C., and the reaction time ranges from 0.5 to 24 hours, preferably from about 1 to 3 hours.

The compound of the formula (Ig-1) can be produced by allowing the compound represented by the formula (XXXVII) to react with the compound represented by the formula (XXXVIII) in the presence of, for example, sodium hydride, alkyl lithium, etc. For example, in a solvent such as dimethylformamide, acetonitrile, diethyl ether, tetrahydrofuran, dioxane, etc., relative to one mole of the compound represented by the formula (XXXVII), the compound represented by the formula (XXXVIII) is employed in an amount ranging from 0.5 to 5 molar equivalents, preferably from 1 to 2 molar equivalents, and, sodium hydride or alkyl lithium is employed in an amount ranging from 0.5 to 3 molar equivalents, preferably from 1 to 1.5 molar equivalents. The reaction temperature ranges from −20° to 100° C., preferably from 0° to 30° C., and the reaction time ranges from 0.5 to 24 hours, preferably from about 1 to 3 hours.

The compound represented by the formula (Ih)

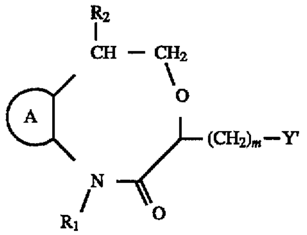

(Ih)

wherein symbols are of the same meaning as defined above, can be produced by the following method.

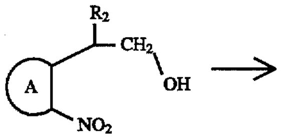

(XXVIII)

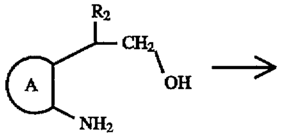

(XXXIX)

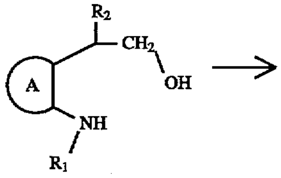

(XXXX)

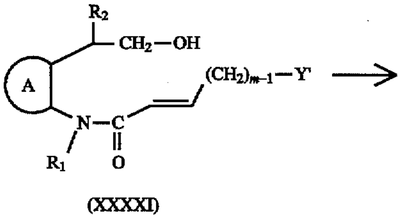

(XXXXI)

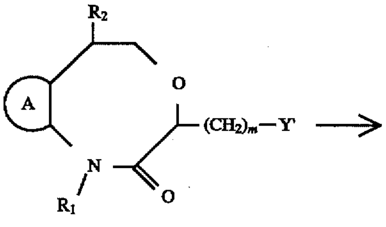

(Ih-1)

-continued

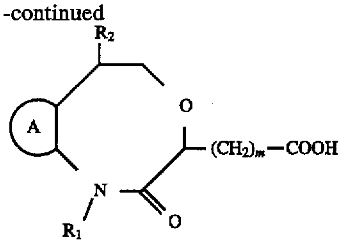

(Ih-2)

The compound represented by the formula (XXXIX) can be produced by subjecting the compound represented by the formula (XXVIII) to hydrogenation in the presence of a palladium catalyst or hydrazine and Raney's nickel catalyst, etc. As the solvent, use is made of an alcohol type solvent such as methanol, ethanol, propanol, etc.; acetic acid ethyl ester, tetrahydrofuran, dimethylformamide or acetonitrile.

Production of compounds represented by the formulae (XXXX), (XXXXI), (Ih-1) and (Ih-2) can be conducted in substantially the same manner as in (Method G) for producing the compound represented by the formula (Id).

The compound represented by the formula (Ii)

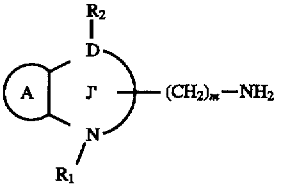

(Ii)

wherein symbols are of the same meaning as defined above, can be produced by allowing a compound represented by the formula (Ij)

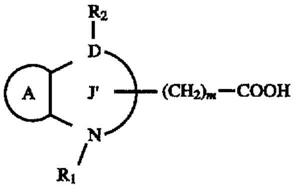

(Ij)

wherein symbols are of the same meaning as defined above, to react with diphenylphosphoryl azide in a solvent in the presence of a base and then by treating the reaction product with an acid in a solvent. As the solvent to be employed for the reaction between the compound represented by the formula (Ij) and diphenylphosphoryl azide, any one can be used so long as it does not hamper the reaction, and, mention is made of for example, a halogen type solvent such as dichloromethane, dichloroethane, chloroform, etc., an ether type solvent such as diethyl ether, tetrahydrofuran, dioxane, etc., dimethylformamide, among others. As the base to be employed, mention is made of triethylamine, 4-dimethylaminopyridine, triethylenediamine, tetramethylethylenediamine, etc. Relative to one mole of the compound represented by the formula (Ij), diphenylphosphorylazide is used in an amount ranging from 1 to 10 molar equivalents, preferably 1.5 to 3 molar equivalents. The reaction temperature ranges from −20° to 50° C., preferably about 0° to 20° C. The reaction time ranges from 0.5 to 5 hours, preferably about 1 to 2 hours.

In the case of processing the reaction product obtained as above with acids, as the solvent to be employed, use is made of water, dioxane, dimethylformamide, etc., and, as the acid to be employed, a mineral acid such as sulfuric acid, hydrochloric acid, nitric acid, hydrobromic acid, etc. The reaction temperature ranges from 20° to 200° C., preferably about 50° to 100° C. The reaction time ranges from 0.5 to 5 hours, preferably about 1 to 2 hours.

The compound represented by the formula (Ik)

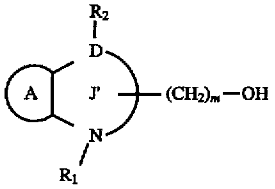

(Ik)

wherein symbols are of the same meaning as defined above, can be produced by subjecting a compound represented by the formula (Im)

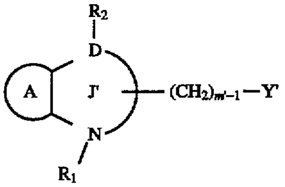

(Im)

wherein m' denote 1, 2, or 3; other symbols are of the same meaning as defined above, to reduction. For example, the compound (Ik) can be produced by processing the compound (Im) with a metal hydrogen complex compound (e.g. lithium aluminum hydride, sodium aluminum hydride, sodium borohydride, etc.) in a protic solvent (method, ethanol, propanol, butanol, etc.) or an aprotic solvent (e.g. ethyl ether, tetrahydrofuran, dioxane, etc.). The metal hydrogen complex compound is used, relative to one mole of the compound represented by the formula (Im), in an amount usually ranging from 0.3 to 5 molar equivalents, preferably about 0.5 to 2 molar equivalents. The reaction temperature ranges from −20° to 100° C., preferably from about 0° to 20° C. The reaction time ranges usually from 0.5 to 10 hours, preferably from about 1 to 3 hours.

And, the compound represented by the formula (Ik) can also be produced by converting the amine portion of the compound represented by the formula (Ii) into hydroxyl group. For example, the compound (Ik) can be produced by adding sodium nitrite to the compound (Ii) in a solvent in the presence of an acid, then, by processing the azide compound thus obtained in a solvent in the presence of a base. For the preparation of the diazo compound, relative to one mole of the compound represented by the formula (Ii), sodium nitrite is used in an amount ranging from 0.5 to 3 molar equivalents, preferably 1 to 1.5 molar equivalent in a solvent, for example, water, an aqueous dioxane or an aqueous dimethylformamide. As the acid to be employed, any one can be employed so long as it does not hamper the reaction, for example, acetic acid, sulfuric acid, etc. in most cases. The reaction temperature ranges from −30° to 20° C., preferably from 0° to 5° C., and the reaction time ranges from 5 to 60 minutes, preferably from about 10 to 30 minutes.

A compound represented by the formula (XXXXII)

(XXXXII)

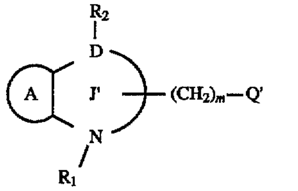

wherein Q' stands for halogen (chlorine, bromine, iodine), and other symbols are of the same meaning as defined above, which is an intermediate compound for synthesizing can be produced, in substantially the same manner as in the case of producing the compound represented by the formula (Ik) from the compound represented by the formula (Ii), by subjecting the compound represented by the formula (Ii) to diazotization with sodium nitrite in hydrochloric acid, hydrobromic acid or hydroiodic acid, then by heating the resultant. The reaction temperature ranges from 20° to 200° C., preferably from 50° to 100° C. The reaction time ranges from 5 minutes to 2 hours, preferably from about 15 to 30 minutes.

A compound represented by the formula (In)

(In)

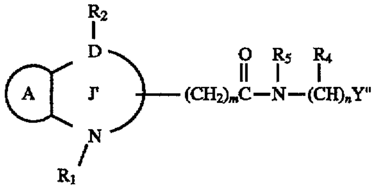

wherein Y" stands for, among those defined by Y, esterified carboxyl group, an optionally substituted carbamoyl group, hydroxyl group, hydrogen, halogen (chlorine, bromine, iodine), other symbols are of the same meaning as defined above, can be produced by subjecting the compound represented by the formula (Ij) and a compound represented by the formula (XXXXIII)

(XXXXIII)

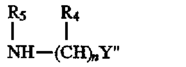

wherein symbols are of the same meaning as defined above, to condensation. The compound represented by the formula (Ij) and the compound represented by the formula (XXXXIII) is condensed with a condensing agent in a solvent and, depending on necessity, in the presence of a base. The solvent to be employed is exemplified by a hydrocarbon type solvent such as benzene, toluene, hexane, heptane, etc., a halogen type solvent such as dichloromethane, dichloroethane, chloroform, carbon tetrachloride, etc., an ether type solvent such as ethyl ether, tetrahydrofuran, dioxane, etc., acetonitrile, dimethylformamide, etc. Examples of the base include triethylamine, 4-dimethylaminopyridine, triethylenediamine, tetramethyl ethylenediamine, etc. As the condensing agent, mention is made of that used in the field of peptide synthesis, as exemplified by dicyclohexylcarbodiimide, diethyl cyanophosphonate, 1-ethyl-3-(3-dimethylaminopropyl)carbodiimide, etc. Relative to one mole of the compound represented by the formula (Ij), the compound represented by the formula (XXXXIII) is used in an amount of ranging from 0.5 to 2 molar equivalents, preferably from 1 to 1.2 molar equivalent, and the condensing agent is used in an amount ranging from 0.5 to 5 molar equivalents, preferably from 1 to 2 molar equivalents. The reaction temperature ranges from 0° to 100° C., preferably 2° to 50° C. The reaction time ranges from 0.5 to 24 hours, preferably from about 1 to 5 hours.

A compound represented by the formula (Io)

(Io)

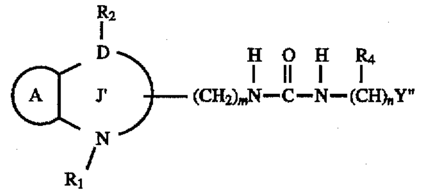

wherein symbols are of the same meaning as defined above, can be produced by allowing the compound represented by the formula (Ij) to react with diphenylphosphoryl azide in a solvent in the presence of a base, then the reaction product is allowed to react with the compound represented by the formula (XXXXIII) in a solvent. The solvent in the reaction between the compound represented by the formula (Ij) and diphenylphosphoryl azide is any one so long as it does not hamper the reaction, which is exemplified by a halogen type solvent such as dichloromethane, chloroform, dichloroethane, etc. and an ether type solvent such as ether, tetrahydrofuran, dioxane, etc. or dimethylformamide. As the base to be employed, mention is made of triethylamine, 4-dimethylaminopyridine, triethylenediamine, tetramethyl ethylenediamine. Relative to one mole of the compound represented by the formula (Ij), diphenylphosphoryl azide is used in an amount ranging from 1 to 10 molar equivalents, preferably 1.5 to 3 molar equivalents. The reaction temperature ranges from −20° to 50° C., preferably from 0° to 20° C. The reaction time ranges from 0.5 to 5 hours, preferably from about 1 to 2 hours.

Examples of the solvent to be employed for the reaction between the reaction product thus obtained and the compound represented by the formula (XXXXIII) include a halogen type solvent such as dichloromethane, dichloroethane, chloroform, etc., an ether type solvent such as ether, tetrahydrofuran, dioxane, etc., acetonitrile, dimethylformamide, etc. And, depending on necessity, a base is employed. As the base, mention is made of an organic base such as triethylamine, 4-dimethylaminopyridine, triethylenediamine, tetramethyl ethylenediamine, etc. Relative to one mole of the compound represented by the formula (Ij), the compound represented. by the formula (XXXXIII) is used in an amount ranging from 0.5 to 3 molar equivalents, preferably 1 to 1.5 molar equivalents. The reaction temperature ranges from 0° to 150° C., preferably 30° to 100° C. The reaction time ranges from 0.5 to 24 hours, preferably about 1 to 3 hours.

A compound represented by the formula (Ip)

(Ip)

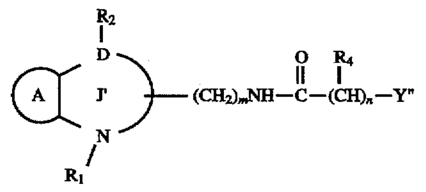

wherein symbols are of the same meaning as defined above, can be produced by subjecting the compound represented by the formula (Ii) to condensation with a compound represented by the formula (XXXXIV)

(XXXXIV)

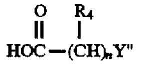

wherein symbols are of the same meaning as defined above. This reaction can be conducted in entirely the same method of producing the compound represented by the formula (In).

A compound represented by the formula (Iq)

(Iq)

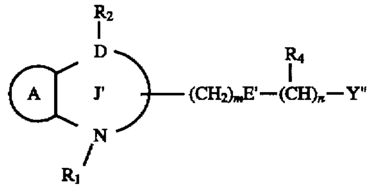

wherein E' stands for oxygen atom or —NH— among the groups defined above as E', and other symbols are of the same meaning as defined above, can be produced by respectively allowing the compound represented by the formula (Ii) and the compound represented by the formula (Ik) to react with a compound represented by (XXXXV)

(XXXXV)

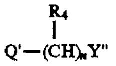

wherein symbols are of the same meaning as defined above. More specifically, the compound represented by the formula (Ii) or the compound represented by the formula (Ik) is allowed to react with the compound represented by the formula (XXXXV) in a solvent, for example, an alcoholic solvent such as methanol, ethanol, propanol, butanol, etc., an ether type solvent such as diethyl ether, tetrahydrofuran, dioxane, etc., dimethylformamide, etc. in the presence of a base, for example, an inorganic base such as sodium hydrogencarbonate, potassium hydrogencarbonate, sodium carbonate, potassium carbonate, etc., an organic base such as triethylamine, 4-dimethylaminopyridine, triethylenediamine, tetramethylethylenediamine, etc. sodium hydride, etc. Relative to one mole of the compound represented by the formula (Ii) or the formula (Ik), the compound represented by the formula (XXXXV) is used in an amount ranging from 0.5 to 1.5 molar equivalent, and relative to one mole of the compound represented by the formula (Ii) or the compound represented by the formula (Ik), the base to be employed is used in an amount ranging from 1 to 5 molar equivalents, preferably 1 to 2 molar equivalents. The reaction temperature ranges from 0° to 200° C., preferably 20° to 100° C. The reaction time ranges from 0.5 to 24 hours, preferably from about 1 to 3 hours.

A compound represented by the formula (Ir)

(Ir)

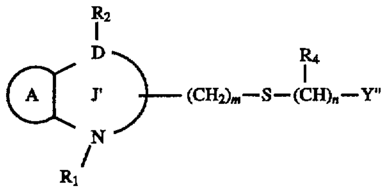

wherein symbols are of the same meaning as defined above, can be produced by allowing the compound represented by the formula (XXXXII) to react with a compound represented by the formula (XXXXVI)

(XXXXVI)

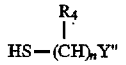

wherein symbols are of the same meaning as defined above. Examples of the solvent to be employed include aprotic solvents including ethyl ether, tetrahydrofuran, dioxane, acetonitrile, dimethylformamide, etc., and, depending on necessity, an inorganic base such as sodium hydrogencarbonate, potassium hydrogencarbonate, sodium carbonate, potassium carbonate, etc., an organic base such as triethylamine, 4-dimethylaminopyridine, triethylenediamine, tetramethylethylenediamine, etc., sodium hydride, cesium fluoride. etc. may be used. Relative to one mole of the compound represented by the formula (XXXXII), the compound represented by the formula (XXXXVI) is used in an amount ranging from 0.5 to 5 molar equivalents, preferably 1 to 2 molar equivalents. The reaction temperature ranges from 0° to 200° C., preferably from 20° to 100° C. The reaction time ranges from 10 minutes to 5 hours, preferably about 30 minutes to 2 hours.

A compound represented by the formula (Is)

(Is)

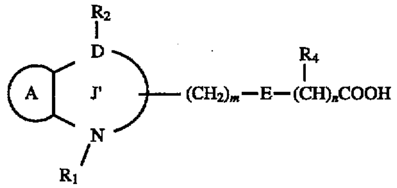

wherein symbols are of the same meaning as defined above, can be produced by subjecting a compound represented by the formula (It)

(It)

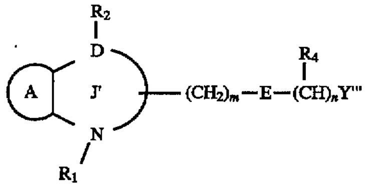

wherein Y''' stands for esterified carboxyl group among the groups defined above as Y, to hydrolysis. More specifically, the compound represented by the formula (It) is subjected to hydrolysis in a solvent such as water, methanol, ethanol, propanol, butanol, etc., in the presence of an alkali metal hydroxide (e.g. sodium hydroxide, potassium hydroxide, barium hydroxide, lithium hydroxide, etc.) or sodium hydrogencarbonate, potassium hydrogencarbonate, sodium carbonate or potassium carbonate, or in the presence of a mineral acid (e.g. nitric acid, hydrochloric acid, hydrobromic acid, folic acid, sulfuric acid, etc.) or trifluoroacetic acid at temperatures ranging from 10° to 150° C., preferably 10° to 50° C. The reaction time ranges, varying with reaction temperatures, usually from 1 to 24 hours, preferably about 2 to 10 hours.

A compound represented by the formula (Iu)

(Iu)

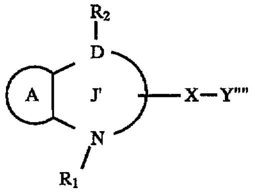

wherein Y"" stands for an optionally substituted carbamoyl group among the groups defined above as Y, and other symbols are of the same meaning as defined above, can be produced by subjecting a compound represented by the formula (Iv)

(Iv)

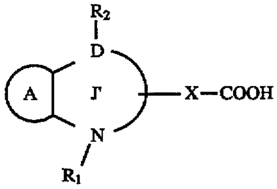

wherein symbols are of the same meaning as defined above, to condensation with amine having the same substituent as that of "optionally substituted carbamoyl group" defined by Y"". The reaction can be allowed to proceed under substantially the same conditions as in the case of producing the compound represented by the formula (In).

A compound represented by the formula (Iw)

(Iw)

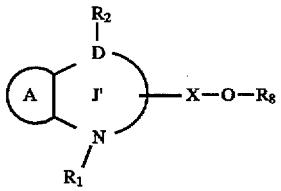

wherein $R_8$ stands for a substituent of "an optionally substituted hydroxyl group" defined by Y, and other symbols are of the same meaning as defined above, can be produced, in substantially the same manner as the method of producing the compound represented by (Iq), from a compound represented by the formula (Ix)

(Ix)

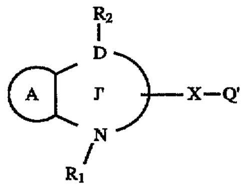

wherein symbols are of the same meaning as defined above, and a compound represented by the formula (XXXXVII), HO-$R_8$, wherein the symbol is of the same meaning as defined above.

A compound represented by the formula (Iy)

(Iy)

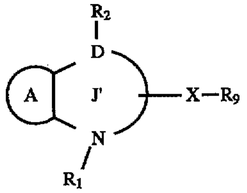

wherein $R_9$ stands for an optionally substituted amino group defined by Y, and other symbols are of the same meaning as defined above, can be produced, in substantially the same manner as producing the compound represented by the formula (Iq), from a compound represented by the formula (XXXXVIII), H—$R_9$, wherein the symbol is of the same meaning as defined above, and the compound represented by the formula (Ix).

A compound represented by the formula (Iz)

(Iz)

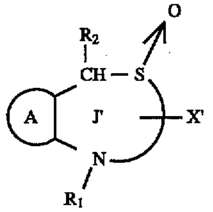

wherein symbols are of the same meaning as defined above, can be produced by allowing a compound represented by the formula (Iα)

(Iα)

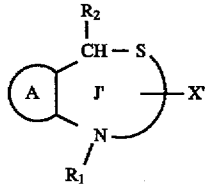

, wherein symbols are of the same meaning as defined above, to react with metachloroperbenzoic acid in a solvent, for example, an ether type solvent such as diethyl ether, tetrahydrofuran, dioxane, etc., a hydrocarbon type solvent such as benzene, toluene, hexane, heptane, etc., a halogen type solvent such as dichloromethane, chloroform, etc., acetonitrile, dimethylformamide, etc. Relative to one mole of the compound (Iα), metachloroperbenzoic acid is used usually in an amount ranging from 1 to 5 moles, preferably about 1 to 1.5 mole. The reaction temperature ranges from 0° to 100° C. preferably from 0° to 30° C. The reaction time ranges from 1 to 10 hours, preferably from about 1 to 2 hours.

A compound represented by the formula (Iβ)

(Iβ)

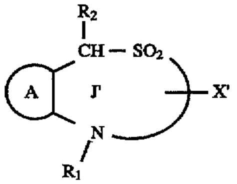

wherein symbols are of the same meaning as defined above, can be produced by employing the compound of the formula (Iz) or the formula (Iα) as the starting material, in substantially the same manner as in the case of producing the compound of the formula (Iz) from the compound of the formula (Iα).

A compound represented by the formula (Iγ)

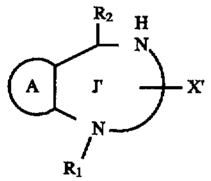

(Iγ)

wherein symbols are of the same meaning as defined above, can be produced by subjecting a compound represented by the formula (Iδ)

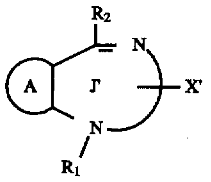

(Iδ)

wherein symbols are of the same meaning as defined above, to reduction in a solvent, for example, water, an alcoholic solvent such as methanol, ethanol, propanol, etc., an ether type solvent such as diethyl ether, tetrahydrofuran, dioxane, etc., a hydrocarbon type solvent such as benzene, toluene, hexane, heptane, etc., a halogen type solvent such as dichloromethane, chloroform, etc., employing, as a reducing agent,sodium borohydride, lithium aluminum hydride, sodium cyanoborohydride, etc. Relative to one mole of the compound represented by the formula (Iδ), the reducing agent is employed in an amount ranging from 0.2 to 5 molar equivalents, preferably from about 0.3 to 1 molar equivalent. The reaction temperature ranges from 0° to 100° C., preferably from 20° to 50° C. The reaction time ranges from 0.5 to 10 hours, preferably from about 1 to 3 hours.

A compound represented by the formula (Iθ)

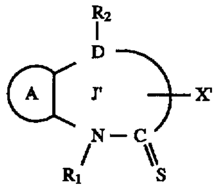

(Iθ)

wherein symbols are of the same meaning as defined above, can be produced by allowing a compound represented by the formula (Iπ)

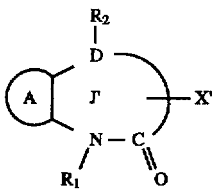

(Iπ)

wherein symbols are of the same meaning as defined above, to react with a Lawesson's reagent or phosphorus pentasulfide in a solvent, for example, an alcoholic solvent such as methanol, ethanol, propanol, etc., an ether type solvent such as diethyl ether, tetrahydrofuran, dioxane, etc., a hydrocarbon type solvent such as benzene, toluene, hexane, heptane, etc., halogen type solvent such as dichloromethane, chloroform, etc., hexamethylphosphoramide, dimethyl sulfoxide, etc. Relative to one mole of the compound of the formula (Iπ), the Lawsson's reagent or phosphorus pentasulfide is used in an amount ranging from 1 to 10 molar equivalents, preferably 1 to 3 molar equivalents. The reaction temperature ranges from 0° to 150° C., preferably from about 50° to 100° C. The reaction time ranges from one to 24 hours, preferably from about 3 to 10 hours, A compound represented by the formula (Iλ)

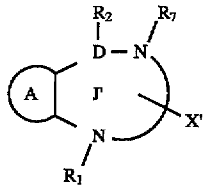

(Iλ)

wherein symbols are of the same meaning as defined above, can be produced by allowing a compound represented by the formula (Iγ) to react with a compound represented by the formula (XXXXIX), $R_7$—Q', wherein symbols are of the same meaning as defined above, in substantially the same conditions as in the cases of producing (XIII) of (Method E), (VI), (II) in (Method F) in the compounds represented by the formula (Id).

While the compounds represented by the general formula (I), (I'), (I'') and (I''') of this invention have a squalene synthetase inhibiting action or an antifungal action, among the compounds used in the present invention, there are compounds capable of inhibiting other enzymes in the pathway of cholesterol biosynthesis. Be the matter as it may, the compounds represented by the formula (I), (I'), (I'') and (I''') inhibit biosynthesis of cholesterol, which is useful for the prophylaxis or therapy of hypercholesterolemia or coronary sclerosis of mammals (e.g. mouse, rat, rabbit, dog, cat, cow, pig and human being), and also useful for the prophylaxis or therapy of fungal infection.

Also the compounds represented by the formula (I), (I'), (II'') and (I''') are useful for therapy of hyperlipidaemia.

These compounds can be administered to man orally or non-orally. The orally administrable compositions may be in a solid or liquid form, more specifically tablets (including sugar-coated tablets and film-coated tablets), pills, granules, powders, capsules (including soft capsule), syrups, emulsions, suspensions or the like. These compositions can be prepared by a per se known method and contain carriers or excipients conventionally used in the field of pharmaceutical preparation, for example, carriers or excipients such as lactose, starch, sucrose or magnesium stearate for preparing tablets.

The non-orally administrable compositions are exemplified by injections and suppositories, and the injections include hypodermic injections, intradermal injections and intramuscular injections. These injections can be prepared by a per se known method, more specifically, by suspending or emulsifying the compound of this invention in a sterile water or oil conventionally used for preparing injectable compositions. The aqueous liquid to be used for preparation of injections include physiological saline solution and isotonic solution, and, depending on necessity, a suitable suspending agent such as sodium carboxymethyl cellulose, a non-ionic surfactant or the like may be jointly used. As the oil, mention is made of sesame oil, soybean oil, etc., and benzyl benzoate, benzyl alcohol etc. as a solubilizer may be jointly used. Injections thus prepared are, in general, filled in appropriate ampoules.

The compounds (I), (I'), (I'') and (I''') or salts thereof are low in toxicity and can be used safely. While the daily dosage varies with the conditions or body weight of the subject patient, kinds of the compounds, administration route, etc., in the case of administering the compound of the present invention for the therapy of hypercholesteremia, a daily oral dosage per adult human is about 1 to 500 mg, preferably about 10 to 200 mg. Within this range, no toxicity is observed at all.

Effective daily dose per adult human of the compounds (I), (I'), (I'') and (I'''), when administered to mammals (e.g. man) as a squalene synthetase inhibitor, ranges from about 1 to 500 mg, preferably from about 10 to 200 mg in the case of oral administration, while, in the case of non-oral administration (e.g. injection, suppository), ranges from about 0.1 to 100 mg, preferably from about 1 to 50 mg.

Further, the compounds (I), (I'), (I'') and (I''') show a broad anti-bacterial activities as determined by the broth or agar dilution method.

Effective daily dose per adult human of the compounds (I), (I'), (I'') and (I''') for the antifungal purpose to be administered to mammals (e.g. man, etc.) ranges from about 0.1 to 100 mg, preferably from about 1 to 50 mg in the case of oral administration, while in the case of non-oral administration (e.g. injection, suppository, etc.) it ranges from about 0.1 to 100 mg, preferably from 1 to 50 mg.

In the present specification, when amino acids, etc. are shown by abbreviations, they are based on those in IUPAC-IUB Commission on Biochemical Nomenclature or on those commonly used in the field concerned. For example, Trp: tryptophane, Ser: serine, Asp: aspartic acid, Glu: glutamic acid, Gly: glycine, Leu: Leucine, Ala: alanine, Me: methyl, Et: ethyl, and Ph: phenyl. And, when the amino acid has optical isomers, they are L-isomers, unless otherwise specified.

[EXAMPLES]

The following examples, formulation examples and test examples are intended to illustrate the present invention in further detail and should by no means be construed as defining the metes and bounds of the invention.

In the following description, stereoisomers are obtained depending of the kinds of compounds, when the groups X' and $R_2$ or $R_2$' bind to saturated carbon atoms. An isomer in which the groups X' and $R_2$ or $R_2$' are oriented in the same direction relative to the face of Ring $J_1$, $J_2$ or J' is named cis-isomer, while another in which the groups X' and $R_2$ or $R_2$' are oriented in the adverse directions to each other is named trans-isomer.

Example 1

3,5-Trans-7-chloro-5-(2-chlorophenyl)-2-oxo-1,2,3,5-tetrahydro-4,1-benzothiazepine-3-acetic acid methyl ester

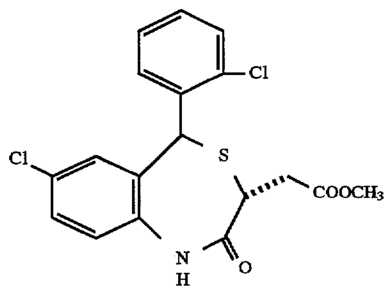

2-Amino-5-chloro-α-(2-chlorophenyl)benzylalcohol (6 g) and thiomalic acid (3.42 g) were dissolved in a mixture of conc. hydrochloric acid (60 ml) and acetic acid (60 ml), and the solution was stirred for 3 hours at 100° C. The reaction mixture was cooled, to which was added 100 ml of 3N aqueous solution of sodium hydroxide. The mixture was extracted with dichloromethane containing tetrahydrofuran by 10% (V/V). The extract solution was washed with a saturated aqueous solution of ammonium chloride, which was then dried over anhydrous sodium sulfate. The solvent was distilled off, and the residue was dissolved in xylene containing dimethylformamide by 3% (V/V), and the solution was heated overnight under reflux. The solvent was distilled off. To the residue were added methanol (50 ml) and conc. sulfuric acid (0.5 ml). The mixture was heated for 3 hours under reflux. The solvent was distilled off. The residue was dissolved in dichloromethane, and the solution was washed with a saturated sodium hydrogencarbonate aqueous solution and a saturated aqueous saline solution, which was then dried over anhydrous sodium sulfate. The solvent was distilled off, and the residue was recrystallized from a mixture solvent of dichloromethane/petroleum ether to give 5.6 g of colorless crystals, m.p. 200°–205° C.

Elemental Analysis for $C_{18}H_{15}Cl_2NO_3S.0.3H_2O$: Calcd.: C 53.82; H 3.91; N, 3.49 Found: C 53.78; H 4.04; N, 3.22

Example 2

3,5-cis-7-Chloro-5-(2-chlorophenyl)-1-neopentyl-2-oxo-1,2,3,5-tetrahydro-4,1-benzothiazepine-3-acetic acid methyl ester

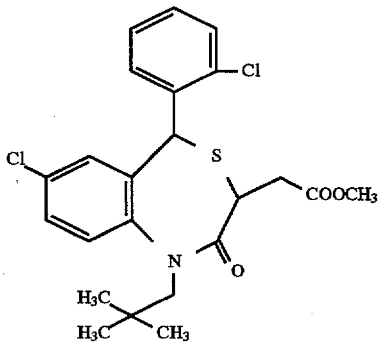

5-Chloro-α-(2-chlorophenyl)-2-(neopentylamino) benzylalcohol (6.5 g) and thiomalic acid (2.85 g) were processed in substantially the same manner as in Example 1. The residue then obtained was recrystallized from a mixture solvent of dichloromethane/petroleum ether to give 2.31 g of colorless crystals, m.p. 153°–156° C.

Elemental Analysis for $C_{23}H_{25}Cl_2NO_3S$: Calcd.: C, 59.23; H, 5.40; N, 3.00; S, 6.87 Found: C, 58.99; H, 5.32; N, 2.76; S, 6.80

Example 3

3,5-trans-7-Chloro-5-(2-chlorophenyl)-1-neopentyl-2-oxo-1,2,3,5-tetrahydro-4,1-benzothiazepine-3-acetic acid methyl ester

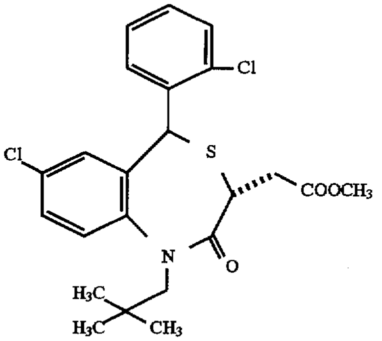

The residue obtained by concentration of the mother liquor resulting from the elimination of the cis-isomer by filtration in recrystallization in Example 2 was dissolved in methanol (30 ml). To the solution was added potassium carbonate (0.87 g), and the mixture was stirred for 3 hours at room temperature. The reaction mixture was concentrated, which was dissolved in dichloromethane. The solution was washed with water, then dried over anhydrous sodium sulfate. The solvent was distilled off, and the residue was purified by means of a silica gel column chromatography (hexane:acetic acid ethyl ester=3:1 (V/V) as an eluent) to give a solid product, which was recrystallized from dichloromethane/petroleum ether to give 2.73 g of colorless crystals, m.p. 133°–136° C.

Elemental Analysis for $C_{23}H_{25}Cl_2NO_3S$: Calcd.: C, 59.23; H, 5.40; N, 3.00; S, 6.87 Found : C, 59.36; H, 5.30; N, 2.84; S, 6.86

Example 4

3,5-trans-7-Chloro-5-(2-chlorophenyl)-1-propyl-2-oxo-1,2,3,5-tetrahydro-4,1-benzothiazepine-3-acetic acid methyl ester

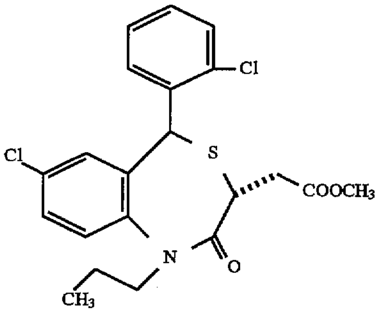

A solution of 3,5-trans-7-chloro-5-(2-chlorophenyl)-2-oxo-1,2,3,5-tetrahydro-4,1-benzothiazepine-3-acetic acid methyl ester (0.5 g) obtained in Example 1 in dimethylformamide (5 ml) was cooled to 0° C. To the solution was added sodium hydride (36 mg), and the mixture was stirred for 5 minutes at 0° C. To this solution was added 1-bromopropane (0.19 g), and the mixture was stirred for 3 hours at room temperature. To the reaction mixture was added water, which was extracted with dichloromethane. The extract solution was washed with a saturated aqueous solution of sodium hydrogencarbonate, which was dried over anhydrous sodium sulfate, then the solvent was distilled off. The residue was purified by means of a silica gel column chromatography (hexane:acetic acid ethyl ester=3:1 (V/V) as an eluent) to give 0.56 g of a colorless oily compound.

IR $\nu_{max}$(neat)$cm^{-1}$: 1740, 1670.

$^1$H-NMR($CDCl_3$) δ: 0.978(3H,t,J=7.6 Hz), 1.563–1.881 (2H,m), 2.445(1H,dd,J=4.0, 17.0 Hz), 3.170(1H,dd,J=10.6, 17.0 Hz), 3.477(1H,ddd,J=5.2, 10.2, 13.6 Hz), 3.673(3H,s), 3.720(1H,dd,J=4.0, 10.6 Hz), 4.215(1H,ddd,J=6.0, 10.4, 13.6 Hz), 6.023(1H,s), 6.633(1H,d,J=2.2 Hz), 7.214–7.477, 7.766–7.798(6H,m)

Example 5

By substantially the same manner as in Example 4, the following compounds were obtained.

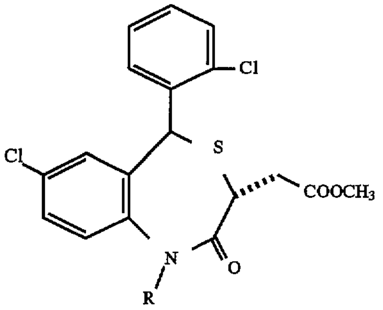

| Cpd. No. | R | m.p. (°C.) | Molecular Formula | Elemental Analysis (Experimental values) C | H | N |
|---|---|---|---|---|---|---|
| 1 | $CH_3$ | 183–185 | $C_{19}H_{17}Cl_2NO_3S$ | 55.62 (55.40 | 4.18 4.04 | 3.41 3.47) |
| 2 | $CH_2CH_3$ | 142–143 | $C_{20}H_{19}Cl_2NO_3S$ | 56.61 (56.55 | 4.51 4.50 | 3.30 3.39) |
| 3 | $CH_2CH(CH_3)_2$ | 157.5–158.5 | $C_{22}H_{23}Cl_2NO_3S$ | 58.41 (58.60 | 5.12 5.21 | 3.10 3.16) |

Example 6

7-Chloro-5-(2-methoxyphenyl)-2-oxo-1,2,3,5-tetrahydro-4,1-benzothiazepine-3-acetic acid methyl ester

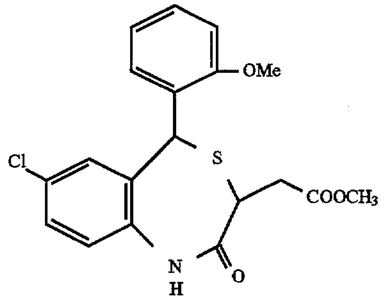

2-Amino-5-chloro-α-(2-methoxyphenyl)benzyl alcohol (1 g) and thiomalic acid (0.60 g) were allowed to proceed in substantially the same manner as in Example 1 to give 1.34 g of a pale yellow amorphous solid.

IR $\nu_{max}$ (KBr) $cm^{-1}$: 1740, 1680.

$^1$H-NMR ($CDCl_3$) δ: 2.394–2.535(1H,m), 3.031–3.187 (1H,m), 3.674, 3.691(6H,each s), 3.792–3.925(1H,m), 5.512, 6.237(1H,), 6.744–7.783(7H,m)

Example 7

3,5-trams-7-Chloro-5-(2-methoxyphenyl)-2-oxo-1-propyl-1,2,3,5-tetrahydro-4,1-benzothiazepine-3-acetic acid methyl ester

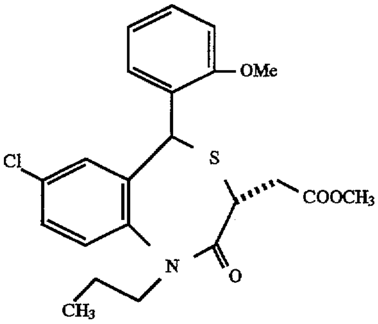

7-Chloro-5-(2-methoxyphenyl)-2-oxo-1,2,3,5-tetrahydro-4,1-benzothiazepine-3-acetic acid methyl ester (0.5 g) obtained in Example 6 was allowed to proceed in substantially the same manner as in Example 4 to give 0.17 g of colorless crystals, m.p. 81°–107° C.

Elemental Analysis for $C_{22}H_{24}ClNO_4S.0.3H_2O$: Calcd.: C, 60.14; H, 5.64; N, 3.19 Found: C, 59.97; H, 5.81; N, 3.01

Example 8

5-Chloro-α-(2-methoxyphenyl)-2-(neopentylamino) benzylalcohol or 2-isobutylamino-5-chloro-α-(2-methoxyphenyl)benzyl alcohol was allowed to proceed substantially the same manner as in Examples 2 and 3 to give the following compounds.

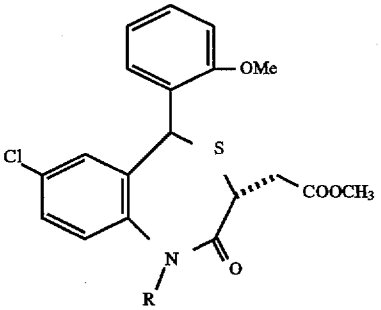

| cpd. No. | R | m.p. (°C.) | Molecular Formula | Elemental Analysis (Experimental values) C | H | N |
|---|---|---|---|---|---|---|
| 1 | $CH_2CH(CH_3)_2$ | 178–179 | $C_{23}H_{28}ClNO_4S$ | 61.67<br>(61.48 | 5.85<br>5.81 | 3.13<br>3.06) |
| 2 | $CH_2C(CH_3)_3$ | 208–211 | $C_{24}H_{28}ClNO_4S$ | 62.39<br>(62.13 | 6.11<br>6.15 | 3.03<br>2.99) |

Example 9

3,5-trans-7-Chloro-5-(2-chlorophenyl)-1-neopentyl-2-oxo-1,2,3,5-tetrahydro-4,1-benzothiazepine-3-acetic acid

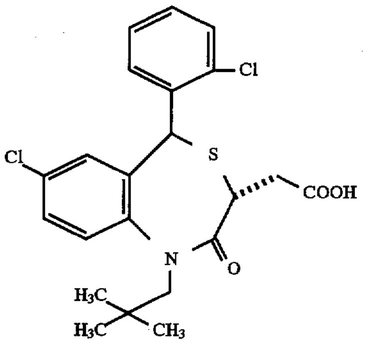

To a mixture of water (2 ml) and methanol (4 ml) were added 3,5-trans-7-chloro-5-(2-chlorophenyl)-1-neopentyl-2-oxo-1,2,3,5-tetrahydro-4,1-benzothiazepine-3-acetic acid methyl ester (0.15 g) obtained in Example 3 and potassium carbonate (0.07 g). The mixture was heated at 60° C. for 2 hours under reflux, to which was added water (50 ml). The solution was made acid with 1N HCl, which was extracted with dichloromethane. The extract solution was washed with a saturated aqueous solution of ammonium chloride, which was dried over anhydrous sodium sulfate. The solvent was then distilled off. The residue was recrystallized from dichloromethane/petroleum ether to give 0.12 g of colorless crystals, m.p. 269–271°0 C.

Elemental analysis for $C_{22}H_{23}Cl_2NO_3S$: Calcd.: C, 58.41; H, 5.12; N, 3.10; S, 7.09 Found : C, 58.39; H, 5.19; N, 2.84; S, 6.78

Example 10

In substantially the same manner as in Example 9, the following compounds were synthesized.

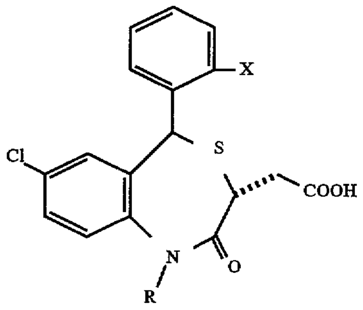

| cpd. No. | R | X | m.p. (°C.) | Molecular Formula | Elemental Analysis (Experimental values) C | H | N |
|---|---|---|---|---|---|---|---|
| 1 | H | Cl | 270–283 | $C_{17}H_{23}Cl_2NO_3S$ | 53.41 | 3.43 | 3.66 |
| | | | (decomp.) | | (53.08 | 3.71 | 3.38) |
| 2 | $(CH_2)_2CH_3$ | Cl | 237–241 | $C_{20}H_{18}Cl_2NO_3S$ | 56.61 | 4.51 | 3.30 |
| | | | | | (56.34 | 4.63 | 3.13) |
| 3 | $CH_3$ | Cl | 183–185 | $C_{18}H_{15}Cl_2NO_3S$ | 55.62 | 4.18 | 3.41 |
| | | | | | (55.40 | 4.04 | 3.47) |
| 4 | $CH_2CH_3$ | Cl | 236–239 | $C_{19}H_{17}Cl_2NO_3S$ | 54.89 | 4.27 | 3.37 |
| | | | | $.0.3H_2O$ | (54.93 | 4.20 | 3.41) |
| 5 | $CH_2CH(CH_3)_2$ | Cl | 225–228 | $C_{21}H_{21}Cl_2NO_3S$ | 56.84 | 4.91 | 3.16 |
| | | | | $.0.3H_2O$ | (56.86 | 5.08 | 3.06) |
| 6 | $(CH_2)_2CH_3$ | $OCH_3$ | 206–208 | $C_{21}H_{22}ClNO_4S$ | 60.07 | 5.28 | 3.34 |
| | | | | | (60.10 | 5.17 | 3.38) |
| 7 | $CH_2CH(CH_3)_2$ | $OCH_3$ | 247–248 | $C_{22}H_{24}ClNO_4S$ | 60.39 | 5.62 | 3.20 |
| | | | (decomp.) | $.0.2H_2O$ | (60.31 | 5.60 | 2.95) |
| 8 | $CH_2C(CH_3)_3$ | $OCH_3$ | 270–285 | $C_{23}H_{28}ClNO_4S$ | 61.67 | 5.85 | 3.13 |
| | | | (decomp.) | | (61.33 | 5.92 | 2.97) |

Example 11

(3R)-7-Chloro-5-(2-chlorophenyl)-2,3-dihydro-2-oxo-1H-1,4-benzodiazepine-3-acetic acid methyl ester

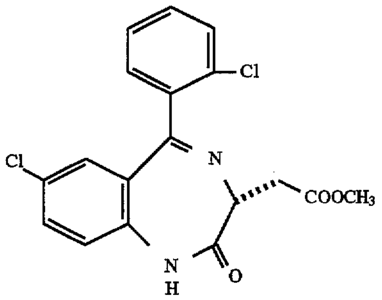

(1) (3R)-3-Benzyloxycarbonylamino-3-[N-[4-chloro-2-(2-chlorobenzoyl)phenyl]carbamoyl]propionic acid methyl ester In dichloromethane (50 ml) was dissolved N-benzyloxycarbonyl-D-aspartic acid beta-methyl ester (4.3 g). The solution was cooled to 0° C., to which were added N-methylmorpholine (1.6 g) and isobutyl chloroformate (2.2 g). The mixture was stirred for 10 minutes at room temperature, to which was added a solution of 2-amino-2',5-dichlorobenzophenone (4.1 g) in dichloromethane (20 ml). The mixture was heated for 20 minutes under reflux. The reaction mixture was. stirred for two days at room temperature, to which was then added dichloromethane (100 ml). The mixture was washed with a 10% aqueous solution of citric acid, a saturated aqueous solution of sodium hydrogencarbonate and a saturated aqueous saline solution, followed by drying over anhydrous sodium sulfate. The solvent was then distilled off, and the residue was recrystallized from hexane/ethyl acetate (3:1 (V/V) to give 3.73 g of pale yellow crystals, m.p. 160°–162° C.

(2) (3R)-7-Chloro-5-(2-chlorophenyl)-2,3-dihydro-2-oxo-1H-1,4-benzodiazepine-3-acetic acid methyl ester To a solution of the compound obtained in (1) (3.76 g) in methanol (60 ml) were added 10% Pd/C (0.5 g) and conc. HCl (0.59 ml). The mixture was subjected to catalytic reduction at ambient temperature under atmospheric pressure. The catalyst was removed and the solvent was distilled off. The residue was dissolved in mixture solvent (dichloromethane; tetrahydrofuran=9:1) (100 ml). The solution was washed with a saturated aqueous solution of sodium hydrogencarbonate and a saturated aqueous saline solution, followed by drying over anhydrous sodium sulfate. The solvent was distilled off, and the residue was dissolved in dimethylformamide (20 ml), to which was added acetic acid (1 ml), followed by stirring for two hours at 60° C. To the reaction mixture was added ethyl acetate (50 ml), which was stirred for two hours at 60° C. To the reaction mixture was added ethyl acetate (50 ml), which was washed with a 5% aqueous solution of potassium hydrogensulfate, a saturated aqueous solution of sodium hydrogencarbonate and a saturated aqueous saline solution. Then the solvent was distilled off, and the residue was recrystallized from ethyl ether to give 2.97 g of colorless crystals, m.p. 168°–170 ° C.

Elemental Analysis for $C_{18}H_{14}Cl_2N_2O_3.0.75H_2O$: Calcd.: C, 55.33; H, 4.00; N, 7.17 Found: C, 54.92; H, 3.60; N, 7.21

Example 12

(3R)-1-Isobutyl-7-chloro-5-(2-chlorophenyl)-2,3-dihydro-2-oxo-1H-1,4-benzodiazepine-3-acetic acid methyl ester

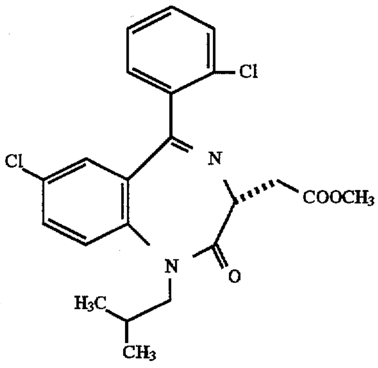

(3R)-7-Chloro-5-(2-chlorophenyl)-2,3-dihydro-2-oxo-1H,1,4-benzodiazepine-3-acetic acid methyl ester (0.5 g) obtained in Example 11 and isobutyl bromide (0.23 g) were allowed to proceed in substantially the same manner as in Example 4 to give 0.3 g of a colorless oily compound.

IR $\nu_{max}$ (neat) $cm^{-1}$: 1740, 1680, 1600

$^1H$-NMR($CDCl_3$) δ: 0.795(3H,d,J=6.4 Hz), 0.882(3H,d, J=6.6 Hz), 1.759(1H,m), 3.220(1H,dd,J=7.0, 16.8 Hz), 3.438(1H,dd,J=7.4, 16.8 Hz), 3.528(1H,qd,J=4.8, 14.2 Hz), 3.723(3H,s), 4.167(1H,t,J=7.1 Hz), 4.332(1H,dd,J=10.0, 14.2 Hz), 7.078(1H,d,J=2.4 Hz), 7.371–7.532(6H,m)

Example 13

(3R)-1-Isobutyl-7-chloro-5-(2-chlorophenyl)-2,3-dihydro-2-oxo-1H-1,4-benzodiazepine-3-acetic acid

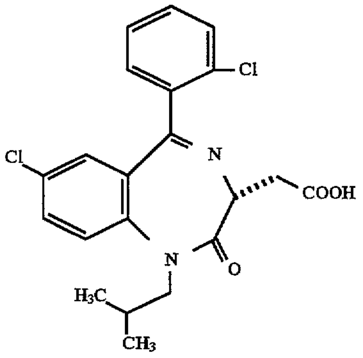

(3R)-1-Isobutyl-7-chloro-5-(2-chlorophenyl)-2,3-dihydro-2-oxo-1H-1,4-benzodiazepine-3-acetic acid methyl ester (0.23 g) obtained in Example 12 was allowed to proceed in substantially the same manner as in Example 9 to give 0.11 g of colorless crystals, m.p. 175°–178° C.

Elemental Analysis for $C_{21}H_{20}Cl_2N_2O_3.0.2H_2$: Calcd.: C, 59.65; H, 4.86; N, 6.62 Found: C, 59.65; H, 4.96; N, 6.62

Example 14

(3R,5S)-1-Isobutyl-7-chloro-5-(2-chlorophenyl)-2,3,4,5-tetrahydro-2-oxo-1H-1,4-benzodiazepine-3-acetic acid

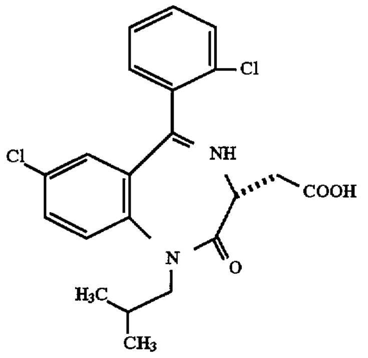

In a mixture solvent (methanol:water=6:1) (0.7 ml) was dissolved (3R)-1-isobutyl-7-chloro-5-(2-chlorophenyl)-2,3-dihydro-2-oxo-1H-1,4-benzodiazepine-3-acetic acid (30 mg) obtained in Example 13. To the solution was added sodium borohydride (10 mg). The reaction mixture was stirred for two hours at room temperature, to which were added dichloromethane (50 ml) and water (50 ml). The aqueous layer was made acid, then the organic layer was washed with a saturated aqueous saline solution, followed by drying over anhydrous sodium sulfate. The solvent was removed, and the residue was recrystallized from dichloromethane/petroleum ether to give 17 mg of colorless crystals, m.p. 184°–188° C.

Elemental Analysis for $C_{21}H_{22}Cl_2N_2O_3.H_2O$: Calcd.: C, 57.41; H, 5.50; N, 6.38 Found: C, 57.56; H, 5.16; N, 6.40

Example 15

(3S)-7-Chloro-5-(2-chlorophenyl)-2,3-dihydro-2-oxo-1H-1,4-benzodiazepine-3-acetic acid methyl ester

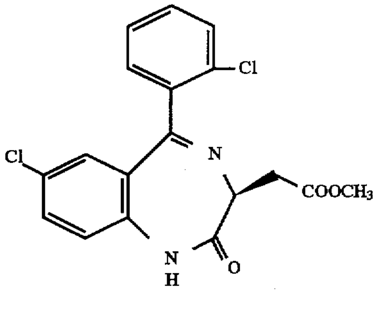

N-Benzyloxycarbonyl-L-aspartic acid beta-methyl ester was allowed to proceed in substantially the same manner as in Example 11 to give a non-crystalline solid product.

IR $\nu_{max}$ (KBr)$cm^{-1}$: 1740, 1690, 1610.

$^1$H-NMR ($CDCl_3$) δ3.218(1H,dd,J=6.8, 17.0 Hz), 3.447 (1H,dd,J=7.4, 17.0 Hz), 3.756(3H,s), 4.234(1H,t,J=7.1 Hz), 7.069–7.130, 7.353–7.486(7H,m)

Example 16

(3S)-1-Isobutyl-7-chloro-5-(2-chlorophenyl)-2,3-dihydro-2-oxo-1H,1,4-benzodiazepine-3-acetic acid methyl ester

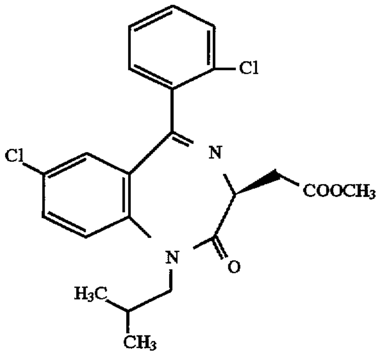

(3S)-7-Chloro-5-(2-chlorophenyl)-2,3-dihydro-2-oxo-1H-1,4-benzodiazepine-3-acetic acid methyl ester obtained in Example 15 was allowed to proceed in substantially the same manner as in Example 4 to give a pale yellow oily compound.

IR $\nu_{max}$(neat) $cm^{-1}$: 1740, 1680, 1610.

$^1$H-NMR ($CDCl_3$) δ: 0.794(3H,d,J=6.6 Hz), 0.881(3H,d, J=6.8 Hz), 1.728(1H,m), 3.219(1H,dd,J=7.0, 16.8 Hz), 3.437(1H,dd,J=7.4, 16.8 Hz), 3.528(1H,qd,J=4.4, 14.2 Hz), 3.723(3H,s), 4.166(1H,t,J=7.1 Hz), 4.332(1H,dd,J=10.0, 14.2 Hz), 7.077(1H,d,J=2.4 Hz), 7.370–7.530(6H,m)

Example 17

(3S)-7-Chloro-5-(2-chlorophenyl)-2,3-dihydro-1-isobutyl-2-oxo-1H-1,4-benzodiazepine-3-acetic acid

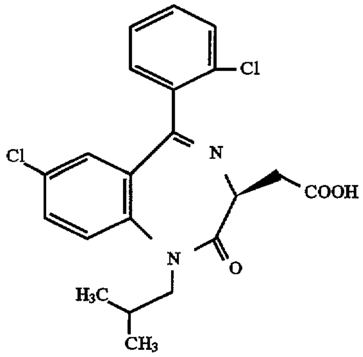

(3S)-1-Isobutyl-7-chloro-5-(2-chlorophenyl)-2,3-dihydro-2-oxo-1H-1,4-benzodiazepine-3-acetic acid methyl ester was allowed to proceed substantially in the same manner as in Example 9 to give a colorless solid compound, m.p. 171°–179° C.

Elemental Analysis for $C_{21}H_{20}Cl_2N_2O_3$: Calcd.: C, 60.15; H, 4.81; N, 6.68 Found: C, 60.41; H, 4.89; N, 6.85

Example 18

3,5-trans-7-Chloro-5-(2-chlorophenyl)-1-neopentyl-2-oxo-1,2,3,5-tetrahydro-4,1-benzothiazepine-3-acetic acid methyl ester S-oxide

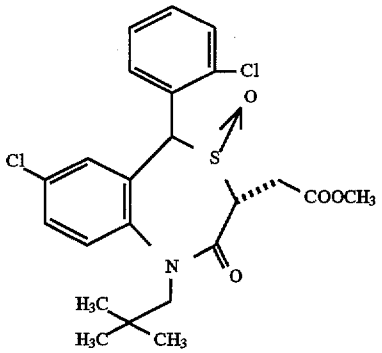

To a solution of 3,5-trans-7-chloro-5-(2-chlorophenyl)-1-neopentyl-2-oxo-1,2,3,5-tetrahydro-4,1-benzothiazepine-3-acetic acid methyl ester (1 g) obtained in Example 3 in dichloromethane (10 ml) was added metachloroperbenzoic acid (0.37 g), which was stirred for 10 minutes at room temperature. To the reaction mixture was added dichloromethane (50 ml), which was washed with a saturated aqueous solution of sodium hydrogencarbonate, then the aqueous layer was further extracted with dichloromethane. The organic layer was washed with a saturated aqueous saline solution and dried over anhydrous sodium sulfate, then the solvent was distilled off. The residue was recrystallized from dichloromethane-hexane to give 0.59 g of colorless crystals, m.p. 166°–169° C.

Elemental Analysis for $C_{23}H_{25}Cl_2NO_4S.1.7H_2O$: Calcd.: C, 53.85; H, 5.58; N, 2.73 Found: C, 53.70; H, 5.27; N, 2.36

Example 19

3,5-trans-7-Chloro-5-(2-chlorophenyl)-1-neopentyl-2-oxo-1,2,3,5-tetrahydro-4,1-benzothiazepine-3-acetic acid S-oxide

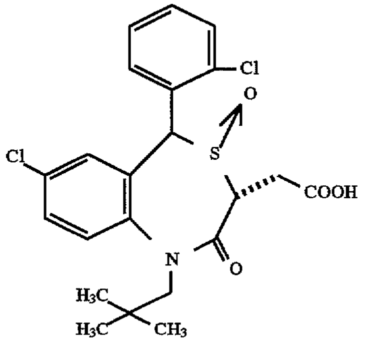

3,5-trans-7-Chloro-5-(2-chlorophenyl)-1-neopentyl-2-oxo-1,2,3,5-tetrahydro-4,1-benzothiazepine-3-acetic acid methyl ester S-oxide (0.5 g) obtained in Example 18 was allowed to proceed in substantially the same manner as in Example 9 to give 0.38 g of colorless crystals, m.p. 230°–235° C.

Elemental Analysis for $C_{22}H_{23}Cl_2NO_4S$: Calcd.: C, 56.41; H, 4.95; N, 2.99 Found: C, 56.36; H, 5.04; N, 3.04

Example 20

3,5-trans-7-Chloro-5-(2-chlorophenyl)-1-neopentyl-2-oxo-1,2,3,5-tetrahydro-4,1-benzothiazepine-3-acetic acid methyl ester S-dioxide

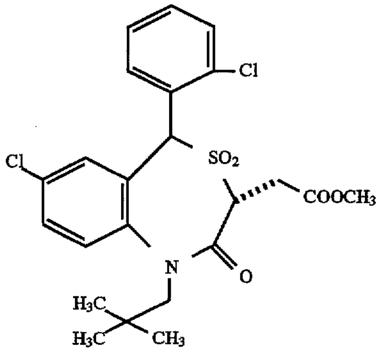

To a solution of 3,5-trans-7-chloro-5-(2-chlorophenyl)-1-neopentyl-2-oxo-1,2,3,5-tetrahydro-4,1-benzothiazepine-3-acetic acid methyl ester (0.3 g) obtained in Example 3 in dichloromethane (10 ml) was added metachloroperbenzoic acid (0.25 g), and the mixture was stirred for 2 hours at room temperature, followed by allowing the reaction to proceed in substantially the same manner as in Example 18 to give 1.01 g of colorless crystals, m.p. 218°–224° C.

Elemental Analysis for $C_{23}H_{25}Cl_2NO_5S$: Calcd.: C, 46.14; H, 5.06; N, 2.81 Found: C, 46.22; H, 5.16; N, 2.69

Example 21

3,5-trans-7-Chloro-5-(2-chlorophenyl)-1-neopentyl-2-oxo-1,2,3,5-tetrahydro-4,1-benzothiazepine-3-acetic acid S-dioxide

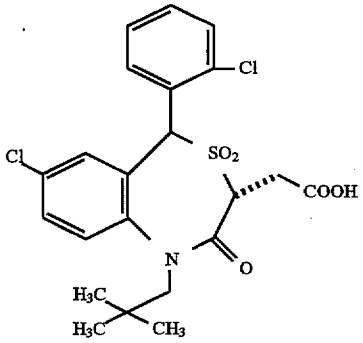

3,5-trans-7-Chloro-5-(2-chlorophenyl)-1-neopentyl-2-oxo-1,2,3,5-tetrahydro-4,1-benzothiazepine-3-acetic acid (0.3 g) obtained in Example 9 was subjected to reaction in substantially the same manners as in Example 18 and Example 20 to give 0.14 g of colorless crystals, m.p. 245°–249° C.

Elemental Analysis for $C_{22}H_{23}Cl_2NO_5S.0.2H_2O$: Calcd.: C, 54.15; H, 4.83; N, 2.87 Found: C, 54.08; H, 4.83; N, 2.65

Example 22

N-[3,5-trans-1-Neopentyl-7-chloro-5-(2-chlorophenyl)-2-oxo-1,2,3,5-tetrahydro-4,1-benzothiazepine-3-acetyl]glycine methyl ester

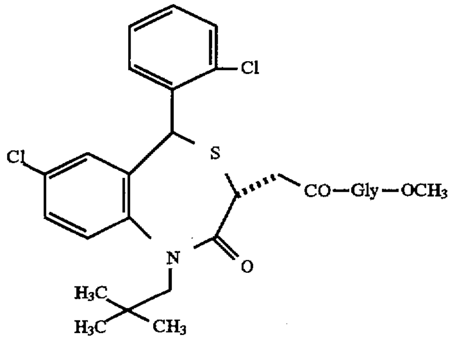

In dichloromethane (2 ml) were dissolved 3,5-trans-7-chloro-5-(2-chlorophenyl)-1-neopentyl-2-oxo-1,2,3,5-tetrahydro-4,1-benzothiazepine-3-acetic acid (0.1 g) obtained in Example 9 and glycine methyl ester hydrochloride (31 mg). To the solution were added, at 0° C., diethyl cyanophosphonate (54 mg) and triethylamine (49 mg). The mixture was stirred for 30 minutes at room temperature. To the reaction mixture was added dichloromethane (50 ml), which was washed with a saturated aqueous solution of sodium hydrogencarbonate and a saturated aqueous saline solution, followed by drying over anhydrous sodium sulfate. The solvent was distilled off, and the residue was recrystallized from dichloromethane/petroleum ether to give 99 mg of colorless crystals, m.p. 188°–189° C.

Elemental Analysis for $C_{25}H_{28}Cl_2N_2O_4S$: Calcd.: C, 57.36; H, 5.39; N, 5.35 Found: C, 57.36; H, 5.39; N, 5.19

Example 23

N-[3,5-trans-7-Chloro-5-(2-chlorophenyl)-1-neopentyl-2-oxo-1,2,3,5-tetrahydro-4,1-benzothiazepine-3-acetyl]glycine

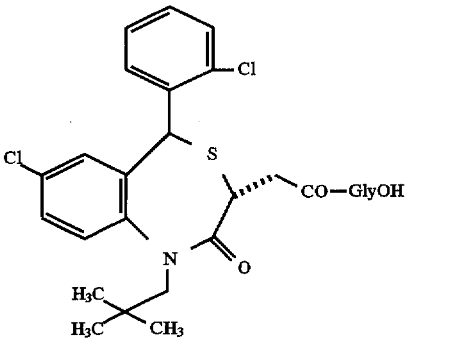

The compound obtained in Example 22 (50 mg) was subjected to hydrolysis in substantially the same manner as in Example 9 to give 35 mg of colorless crystals, m.p. 229°–230° C.

Elemental Analysis for $C_{24}H_{26}Cl_2N_2O_4S.0.3H_2O$: Calcd.: C, 55.99; H, 5.21; N, 5.44 Found: C, 55.98; H, 5.09; N, 5.29

Example 24

3,5-trans-7-Chloro-5-(2-chlorophenyl)-3-dimethylaminocarbonylmethyl-1-neopentyl-2-oxo-1,2,3,5-tetrahydro-4,1-benzothiazepine

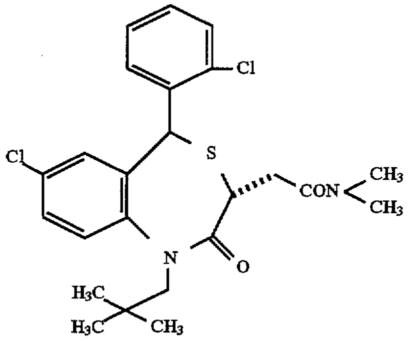

To a solution of 3,5-trans-7-chloro-5-(2-chlorophenyl)-1-neopentyl-2-oxo-1,2,3,5-tetrahydro-4,1-benzothiazepine-3-acetic acid (1 g) obtained in Example 9 and dimethylamine hydrochloride (0.2 g) in dichloromethane (20 ml) were added diethyl cyanophosphomate (375 mg) and triethylamine (558 mg). The mixture was stirred for 30 minutes at room temperature. To the reaction mixture was added dichloromethane (100 ml), which was washed with 5% HCl, a saturated aqueous solution of sodium hydrogencarbonate and an aqueous saline solution, then the solvent was distilled off. The residue was recrystallized from dichloromethane/petroleum ether to give 0.98 g of colorless crystals, m.p. 190°–193° C.

Elemental Analysis for $C_{24}H_{28}Cl_2N_2O_2S$: Calcd.: C, 60.12; H, 5.89; N, 5.84 Found: C, 59.99; H, 5.88; N, 5.92

Example 25

7-Chloro-5-(2-chlorophenyl)-1-isobutyl-2-oxo-2,3,4,5-tetrahydro-1H-[1]-benzazepine-3-acetic acid ethyl ester

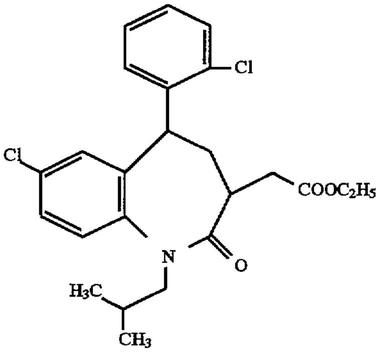

In accordance with the method disclosed in J. Med. Chem., 27, 1508 (1984), J. Med. Chem., 14, 851 (1971), the following intermediate compounds were synthesized.

(1) 3-(ethoxycarbonyl)-4-(2-chlorophenyl)-4-phenyl-3-butenic acid, an oily compound IR $\nu_{max}$(neat) $cm^{-1}$: 1730, 1715, 1705.

(2) 4-(2-Chlorophenyl)-4-phenylbutyric acid ethyl ester an oily compound

IR $\nu_{max}$(neat) $cm^{-1}$: 1730.

$^1$H-NMR($CDCl_3$) δ: 1.23(3H,t,J=7.1 Hz), 2.2–2.5(4H,m), 4.10(2H,q,J=7.1 Hz), 4.45–4.6(1H,m), 7.0–7.4(9H,m)

(3) 4-(2-Chlorophenyl)-4-phenylbutyric acid m.p. 133–135° C.

Elemental Analysis for $C_{16}H_{15}ClO_2$: Calcd.: C, 69.95; H, 5.50 Found: C, 70.10; H, 5.42

(4) 4-(2-Chlorophenyl)-1-tetralone an oily compound

IR $\nu_{max}$(neat) $cm^{-1}$: 1685.

$^1$H-NMR ($CDCl_3$) δ: 2.2–2.5(2H,m), 2.6–2.8(2H,m), 4.85 (1H,t,J=5.9 Hz), 6.7–7.5(7H,m), 8.05–8.2(1H,m)

(5) 4-(2-Chlorophenyl)-1-tetralone oxime m.p. 114°–115° C.

(6) 5-(2-Chlorophenyl)-2,3,4,5-tetrahydro-1H-[1]-benzazepin-2-one m.p. 226°–227° C.

Elemental Analysis for $C_{16}H_{14}ClNO$: Calcd.: C, 70.72; H, 5.19; N, 5.15 Found: C, 70.94; H, 5.20; N, 5.20

(7) 5-(2-Chlorophenyl)-1-isobutyl-2,3,4,5-tetrahydro-1H-[1]-benzazepin-2-one

To a solution of 5-(2-chlorophenyl)-2,3,4,5-tetrahydro-1H-[1]-benzazepin-2-one (2.8 g) and isobutyl bromide (2.24 ml) in dimethylformamide (20 ml) was added sodium hydride (0.82 g, 60% oil) at 0° C. The mixture was stirred for 4 hours at room temperature, then the solvent was distilled off, and the residue was purified by means of a silica-gel column chromatography to give 2.98 g of colorless crystals, m.p. 139°–140° C.

Elemental Analysis for $C_{20}H_{22}ClNO$: Calcd.: C, 73.27; H, 6.76; N, 4.27 Found: C, 73.08; H, 6.69; N, 4.36

(8) 7-Chloro-5-(2-chlorophenyl)-1-isobutyl-2,3,4,5-tetrahydro-1H-[1]-benzazepin-2-one A solution of 5-(2-chlorophenyl)-1-isobutyl-2,3,4,5-tetrahydro-1H-[1]-benzazepin-2-one (2.7 g) and N-chlorosuccinimide (1.65 g) in dimethylformamide (10 ml) was stirred for 7 hours at 70° C. To the reaction mixture was added acetic acid ethyl ester (100 ml), which was washed with dilute hydrochloric acid and a saturated aqueous solution of sodium hydrogencarbonate, followed by drying over anhydrous sodium sulfate. The solvent was removed, and the residue was recrystallized from hexane/acetic acid ethyl ester to give 2.39 g of colorless crystals, m.p. 152°–154° C.

(9) 7-Chloro-5-(2-chlorophenyl)-1-isobutyl-2-oxo-2,3,4,5-tetrahydro-1H-[1]-benzazepine-3-acetic acid ethyl ester To dry tetrahydrofuran (5 ml) was added isopropylamine (0.25 ml), and the mixture was cooled to −15° C. to which was added a 1.58M hexane solution of n-butyl lithium (1.14 ml), and the mixture was stirred for 45 minutes at −15° C. To the reaction mixture was added 7-chloro-5-(2-chlorophenyl)-2,3,4,5-tetrahydro-1H-[1]-benzazepin-2-one (0.5 g) dissolved in tetrahydrofuran (5 ml), which was stirred for 15 minutes at 0° C. The reaction mixture was cooled to −78° C., to which was added iodoacetic acid ethyl ester (0.25 ml). The mixture was stirred for 15 minutes at −78° C., then for one hour at 0° C. To the reaction mixture was added 1N hydrochloric acid (50 ml), which was extracted with acetic acid ethyl ester. The acetic acid ethyl ester layer was washed with a saturated aqueous solution of hydrogencarbonate, followed by drying over anhydrous magnesium sulfate. The solvent was distilled off, and the residue was purified by means of a silica-gel column chromatography to give 0.1 g of an oily compound.

IR $\nu_{max}$(neat)$cm^{-1}$: 1730, 1660.

$^1$H-NMR ($CDCl_3$) δ: 0.5–1.15(6H,m), 1.15–1.4(3H,m), 1.7–3.1(5H,m), 3.1–3.9(2H,m), 4.0–4.1(2H,m), 4.4–4.8(1H, m), 6.4–7.6(7H,m)

SIMS (m/z): 449 ($MH^+$)

Example 26

7-Chloro-5-(2-chlorophenyl)-1-isobutyl-2-oxo-2,3,4,5-tetrahydro-1H-[1]-benzazepine-3-acetic acid

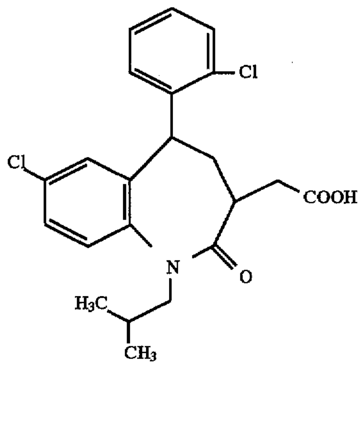

The compound (90 mg) obtained in Example 25 was allowed to proceed in substantially the same manner as in Example 9 to give 50 mg of colorless crystals, m.p. 165°–171° C.

Elemental Analysis for $C_{22}H_{23}Cl_2NO_3$: Calcd.: C, 62.86; H, 5.51; N, 3.33 Found: C, 62.77; H, 5.61; N, 3.29

Example 27

3,5-trans-7-Chloro-5-(2-chlorophenyl)-1-neopentyl-1,2,3,4-tetrahydro-2-thioxo-4,1-benzoxazepine-3-acetic acid ethyl ester

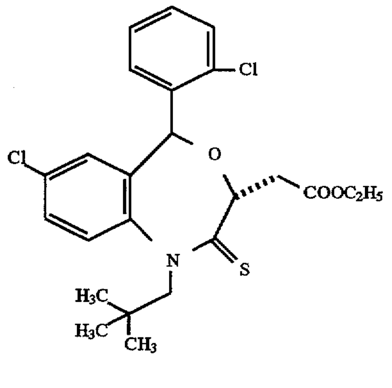

A solution of 3,5-trans-7-chloro-5-(2-chlorophenyl)-1-neopentyl-2-oxo-1,2,3,4-tetrahydro-4,1-benzoxazepine-3-acetic acid ethyl ester (1.0 g) and Lawesson's reagent (1.3 g) in toluene (15 ml) was heated for 8 hours under reflux. Insolubles were filtered off, and the filtrate was concentrated under reduced pressure. The concentrate was purified by means of a silica gel column chromatography to give 0.68 g of yellow crystals, m.p. 200°–201° C.

Elemental Analysis for $C_{24}H_{27}Cl_2NO_3S$: Calcd.: C, 60.00; H, 5.66; N, 2.92 Found: C, 60.10; H, 5.78; N, 2.65

Example 28

3,5-trans-7-Chloro-5-(2-chlorophenyl)-1-neopentyl-1,2,3,4-tetrahydro-2-thioxo-4,1-benzoxazepine-3-acetic acid

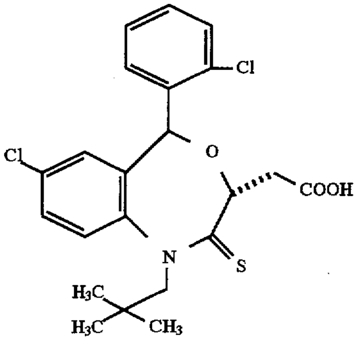

The compound (0.4 g) obtained in Example 27 was allowed to proceed in substantially the same manner as in Example 9 to give 0.1 g of yellow crystals, m.p. 248°–249° C.

Elemental Analysis for $C_{22}H_{23}Cl_2NO_3S$: Calcd.: C, 58.41; H, 5.12; N, 3.10 Found: C, 58.48; H, 5.33; N, 3.01

Example 29

3,5-trans-7-Chloro-5-(2-chlorophenyl)-1,2,3,5-tetrahydro-2-thioxo-4,1-benzothiazepine-3-acetic acid methyl ester

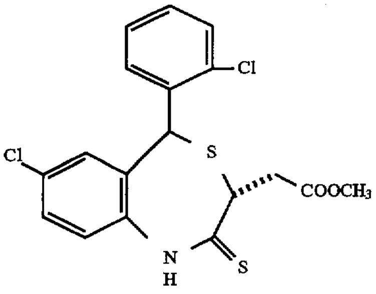

3,5-trans-7-Chloro-5-(2-chlorophenyl)-2-oxo-1,2,3,5-tetrahydro-4,1-benzothiazepine-3-acetic acid ethyl ester (1.0 g) obtained in Example 1 was allowed to proceed in substantially the same manner as in Example 27 to give 0.95 g of yellow crystals, m.p. 194°–197° C.

Elemental Analysis for $C_{18}H_{15}Cl_2NO_2S_2$: Calcd.: C, 52.43; H, 3.67; N, 3.40 Found: C, 52.41; H, 3.53; N, 3.10

Example 30

5 7-Chloro-5-(2-chlorophenyl)-1-neopentyl-2-oxo-1,2,3,5-tetraydro-4,1-thieno[2,3-e]oxazepine-3-acetic acid ethyl ester

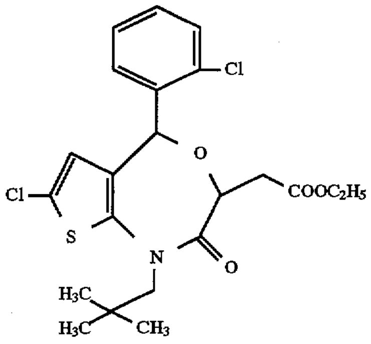

(1) 5-Chloro-3-(2-chlorobenzoyl)-2-neopentylaminothiophene

In a mixture solvent of methanol (200 ml) and acetic acid (100 ml) was dissolved 2-amino-5-chloro-3-(2-chlorobenzoyl)thiophene (10.89 g). To the solution were added pivalaldehyde (8.69 ml) and molecular sieves 3A (0.5 g). The mixture was stirred for 2 hours at 60° C., to which was added dropwise a solution of sodium cyanoborohydride (2.51 g) in methanol (10 ml), and the mixture was stirred for 2.5 hours at room temperature. The solvent was distilled off. The residue was dissolved in acetic acid ethyl ester. The organic layer was washed with a saturated aqueous solution of sodium hydrogencarbonate and water, then dried over anhydrous magnesium sulfate. The solvent was distilled off, and the residue was purified by means of a silica-gel column chromatography to give 4.85 g of pale yellow crystals, m.p. 74°–76° C.

Elemental Analysis for $C_{16}H_{17}Cl_2NOS$: Calcd.: C, 56.14; H, 5.01; N, 4.09 Found : C, 56.18; H, 5.17; N, 3.89

(2) 3-[N-[5-Chloro-3-(2-chlorobenzoyl)-2-thienyl]-N-neopentylcarbamoyl]acrylic acid ethyl ester To a solution of 5-chloro-3-(2-chlorobenzoyl)-2-neopentylaminothiophene (4.85 g), triethylamine (5.92 ml) and a small amount of dimethylaminopyridine in 5 dimethylformamide (60 ml) was added dropwise a solution of fumaric chloride monoethyl ester (4.60 g) in dimethylformamide (20 ml). The reaction mixture was stirred overnight at room temperature, which was poured into water, followed by extraction with acetic acid ethyl ester. The extract solution was washed with 1M aqueous solution of potassium hydrogen sulfate and a saturated aqueous saline solution, followed by drying over. anhydrous magnesium sulfate. The solvent was distilled off. The residue was purified by a silica-gel column chromatography, followed by recrystallization from hexane/acetic acid ethyl ester to give 4.3 g of colorless crystals, m.p. 79°–81° C.

Elemental Analysis for $C_{22}H_{23}Cl_2NO_4S.0.5H_2O$: Calcd.: C, 55.35; H, 5.07; N, 2.93 Found: C, 55.25; H, 4.83; N, 3.00

(3) 3-[N-[5-Chloro-3-(α-hydroxy-2-chlorobenzyl)-2-thienyl]-N-neopentylcarbamoyl]acrylic acid ethyl ester To a solution of 3-[N-[5-chloro-3-(2-chlorobenzoyl)-2-thienyl]-N-neopentylcarbamoyl]acrylic acid ethyl ester (2.37 g) and cesium trichloride.heptahydrate (2.98 g) in methanol (100 ml) was gradually added, sodium borohydride (303 mg) at room temperature. The mixture stirred for 20 minutes at room temperature, to which was added acetone, then the solvent was distilled off. To the residue were added 1M potassium hydrogensulfate and acetic acid ethyl ester. The organic layer was washed with a saturated aqueous saline solution, followed by drying over anhydrous magnesium sulfate. The solvent was distilled off, and the residue was purified by means of a silica-gel column chromatography to give a non-crystalline solid (2.47 g).

$^1$H-NMR ($CDCl_3$) δ0.91, 1.00(9H), 1.20–1.35(3H,m), 2.50–2.59(1H,m), 2.90–4.28(4H,m), 5.95, 6.05(total 1H), 6.52–7.60(7H,m)

(4) 7-Chloro-5-(2-chlorophenyl)-1-neopentyl-2-oxo-1,2,3,5-tetrahydro-4,1-thieno[2,3-e]oxazepine-3-acetic acid ethyl ester To a solution of 3-[N-[5-chloro-3-(α-hydroxy-2-chlorobenzyl)-2-thienyl]-N-neopentylcarbamoyl]acrylic acid ethyl ester (2.37 g) in ethanol (50 ml) was added potassium carbonate (700 mg). The mixture was stirred for 8 hours at room temperature. The reaction mixture was poured into water, which was extracted with acetic acid ethyl ester. The extract solution was washed with a saturated aqueous saline solution, followed by drying over anhydrous magnesium sulfate. The solvent was distilled off. The residue was purified by means of a silica-gel column chromatography to give a pale yellow oily compound (1.73 g).

$^1$H-NMR ($CDCl_3$) δ: 0.99, 1.02(9H,each s), 1.26, 1.28 (3H,each t), 2.60–3.09(3H,m), 4.08–4.25(2H,m), 4.38, 4.57 (1H,each d), 4.67, 4.92(1H,each dd), 5.87, 6.42(1H,each s), 6.06, 6.51(1H,each s), 7.20–7.66(4H,m)

Example 31

3,5-trans-7-Chloro-5-(2-chlorophenyl)-1-neopentyl-2-oxo-1,2,3,5-tetrahydro-4,1-thieno[2,3-e]benzoxazepine-3-acetic acid

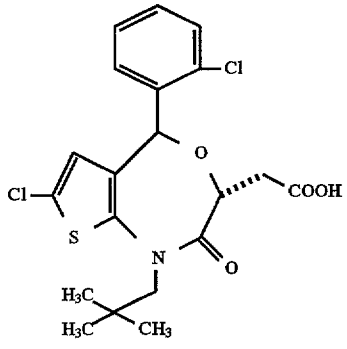

The compound obtained in Example 30 (1.64 g) was dissolved in a mixture solvent of methanol (30 ml) and tetrahydrofuran (30 ml). To the solution was added potassium carbonate, which was then stirred for 2 hours at 60° C. The reaction mixture was made acid with 1N hydrochloric acid, which was then poured into water, followed by extraction with acetic acid ethyl ester. The organic layer was dried over anhydrous magnesium sulfate. The solvent was distilled off, and the residue was purified by means of a silica-gel column chromatography to give a solid matter, which was recrystallized from hexane/acetic acid ethyl ester to give 68 mg of colorless crystals, m.p. 202°–204° C.

Elemental Analysis for $C_{20}H_{21}Cl_2NO_4S$: Calcd.: C, 54.30; H, 4.78; N, 3.17 Found: C, 54.20; H, 4.62; N, 3.16

Example 32

3,5-trans-7-Chloro-5-(2-methoxyphenyl)-1-neopentyl-2-oxo-1,2,3,5-tetrahydro-4,1-thieno[2,3-e]oxazepine-3-acetic acid ethyl ester and 3,5-cis-7-chloro-5-(2-methoxyphenyl)-1-neopentyl-2-oxo-1,2,3,5-tetrahydro-4,1-thieno[2,3-e]oxazepine-3-acetic acid ethyl ester

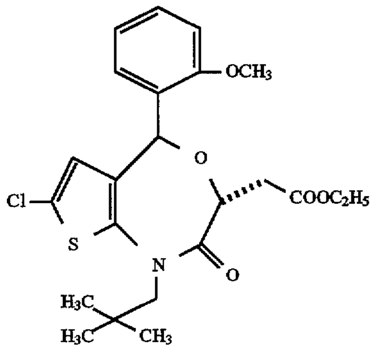

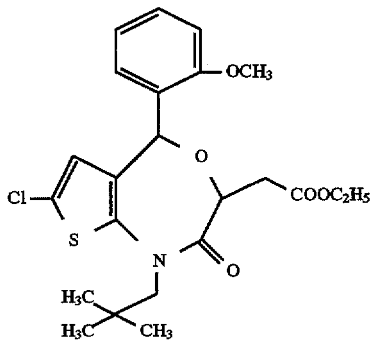

In substantially the same manner as in Example 30, these compounds were produced.

(1) 5-Chloro-3-(2-methoxybenzoyl)-2-neopentylamino thiophene m.p. 117°–118° C.

Elemental Analysis for $C_{17}H_{20}ClNO_2S$: Calcd.: C, 60.43; H, 5.97; N, 4.15 Found: C, 60.15; H, 5.92; N, 4.10

(2) 3-[N-[5-Chloro-3-(2-methoxybenzoyl)-2-thienyl]-N-neopentylcarbamoyl]acrylic acid ethyl ester an oily compound $^1$H-NMR($CDCl_3$) δ: 0.96(9H,s), 1.26(3H,t,J=7.2 Hz), 3.57(1H,d,J=13.7 Hz), 3.73(3H,s), 3.74(1H,d,J=13.7 Hz), 4.18(2H,q,J=7.2 Hz), 6.75(1H,s), 6.81(1H,d,J=15.3 Hz), 6.90–7.04(2H,m), 7.12(1H,d,J=15.3 Hz), 7.31–7.51(2H,m)

(3) 3-[N-[5-Chloro-3-(α-hydroxy-2-methoxybenzyl)-2-thienyl]-N-neopentylcarbamoyl]acrylic acid ethyl ester an oily compound $^1$H-NMR($CDCl_3$) δ: 0.91, 1.00(9H,each s), 1.24, 1.28(3H, each t), 2.80–2.91, 3.32(1H), 3.74, 3.82(3H,each s), 4.06–4.27(3H,m), 5.81, 5.93(1H,each d), 6.40–7.34(7H,m)

(4) 3,5-trans-7-Chloro-5-(2-methoxyphenyl)-1-neopentyl-2-oxo-1,2,3,5-tetrahydro-4,1-thieno[2,3-e]oxazepine-3-acetic acid ethyl ester m.p. 148°–150° C.

Elemental Analysis for $C_{23}H_{28}ClNO_5S$: Calcd.: C, 59.28; H, 6.06; N, 3.01 Found : C, 59.17; H, 5.95; N, 2.90

3,5-cis-7-Chloro-5-(2-methoxyphenyl)-1-neopentyl-2-oxo-1,2,3,5-tetrahydro-4,1-thieno[2,3-e]oxazepine-3-acetic acid ethyl ester $^1$H-NMR($CDCl_3$) δ: 0.97(9H,s), 1.26(3H,t,J=7.1 Hz), 2.81(1H,dd,J=8.1,17.0 Hz), 2.96(1H,d,J=14.2 Hz), 3.01(1H, dd,J=5.8,17.0 Hz), 3.89(3H,s), 4.10–4.23(2H,m), 4.54(1H, d,J=14.2 Hz), 4.90(1H,dd,J=5.8,8.1 Hz), 6.42(1H,s), 6.56 (1H,s), 6.88–6.97(2H,m), 7.22–7.32(1H,m), 7.35–7.41(1H, m)

Example 33

3,5-trans-7-Chloro-5-(2-methoxyphenyl)-1-neopentyl-2-oxo-1,2,3,5-tetrahydro-4,1-thieno[2,3-e] oxazepine-3-acetic acid

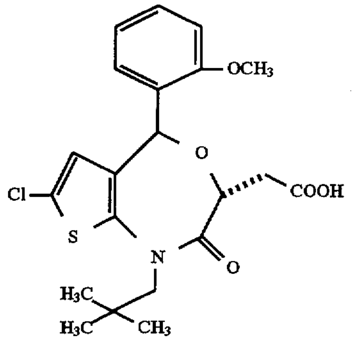

The trans-form ethyl ester (0.51 g) obtained in Example 32 was allowed to proceed in substantially the same manner as in Example 31 to give 0.18 g of colorless crystals, m.p. 220°–222° C.

Elemental Analysis for $C_{21}H_{24}ClNO_5S$: Calcd.: C, 57.59; H, 5.52; N, 3.20 Found: C, 57.54; H, 5.58; N, 3.18

Example 34

3,5-cis-7-Chloro-5-(2-methoxyphenyl)-1-neopentyl-2-oxo-1,2,3,5-tetrahydro-4,1-thieno[2,3-e] oxazepine-3-acetic acid

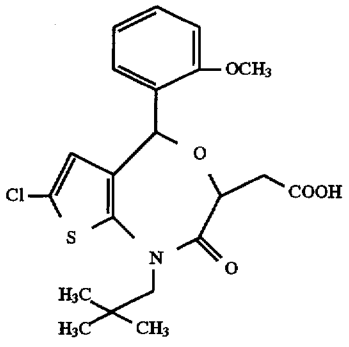

The cis-form ethyl ester obtained in Example 32 (0.28 g) was allowed to proceed substantially the same manner as in Example 31 to give 0.16 g of colorless crystals, m.p. 189°–191° C.

Elemental Analysis for $C_{21}H_{24}ClNO_5S$: Calcd.: C, 57.59; H, 5.52; N, 3.20 Found: C, 57.36; H, 5.42; N, 3.11

Example 35

3,5-trans-7-Chloro-1-isobutyl-5-(2-methoxyphenyl)-2-oxo-1,2,3,5-tetrahydro-4,1-thieno[2,3-e] oxazepine-3-acetic acid ethyl ester and 3,5-cis-7-chloro-1-isobutyl-5-(2-methoxyphenyl)-2-oxo-1,2,3,5-tetrahydro-4,1-thieno[2,3-e]oxazepine-3-acetic acid ethyl ester

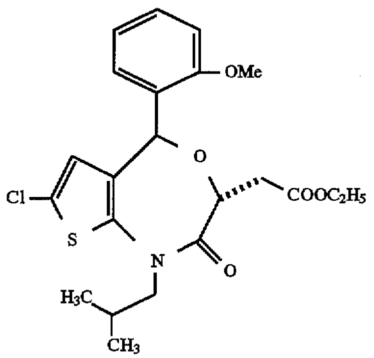

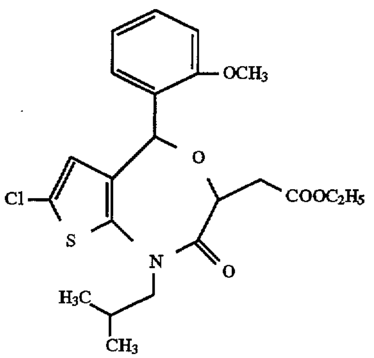

These compounds were produced in substantially the same manner as in Example 30.

(1) 5-Chloro-2-isobutylamino-3-(2-methoxybenzoyl) thiophene m.p. 83°–84° C.

Elemental Analysis for $C_{16}H_{18}ClNO_2S$: Calcd.: C, 59.34; H, 5.60; N, 4.33 Found: C, 59.41; H, 5.63; N, 4.30

(2) 3-[N-[5-Chloro-3-(2-methoxybenzoyl)-2-thienyl]-N-isobutylcarbamoyl]acrylic acid ethyl ester an oily compound $^1$H-NMR($CDCl_3$) δ: 0.92(6H,br), 1.28 (3H,t,j=7.1 Hz), 1.89–2.12(1H,m), 3.12–3.27(1H,m), 3.75 (3H,s), 3.80–4.00(1H,m), 4.20(2H,q,J=7.1 Hz), 6.76–7.54 (7H,m)

(3) 3-[N-[5-Chloro-3-(α-hydroxy-2-methoxYbenzyl)-2-thienyl]-N-isobutylcarbamoyl]acrylic acid ethyl ester an oily compound $^1$H-NMR($CDCl_3$) δ: 0.80–1.00(6H,m), 1.19–1.32(3H,m), 1.88–2.16(1H,m), 2.69–3.24(2H,m), 3.74,3.79(3H,each s), 3.87–4.26(3H,m), 5.80–5.99(1H,m), 6.49–7.64(7H,m)

(4) 3,5-trans-7-Chloro-1-isobutyl-5-(2-methoxyphenyl)-2-oxo-1,2,3,5-tetrahydro-4,1-thieno[2,3-e]oxazepine-3-acetic ethyl ester m.p. 126°–128° C.

Elemental Analysis for $C_{22}H_{26}ClNO_5S$: Calcd.: C, 58.46; H, 5.80; N, 3.10 Found: C, 58.23; H, 5.72; N, 3.03

3,5-cis-7-Chloro-1-isobutyl-5-(2-methoxyphenyl)-2-oxo-1,2,3,5-tetrahydro-4,1-thieno[2,3-e]oxazepine-3-acetic acid ethyl ester an oily compound $^1$H-NMR($CDCl_3$) δ: 0.96(6H,d,J=6.6 Hz), 1.27(3H,t,J=7.1 Hz), 2.05–2.24(1H,m), 2.81(1H,dd,J=8.1,17.0 Hz), 3.00 (1H,dd,J=5.6,17.0 Hz), 3.09(1H,dd,J=5.3,14.1 Hz), 3.88

(3H,s), 4.17(2H,q,J=7.1 Hz), 4.31(1H,dd,J=9.3,14.1 Hz), 4.89(1H,dd,J=5.6,8.1 Hz), 6.41(1H,s), 6.48(1H,s), 6.86–6.96(2H,m), 7.20–7.34(2H,m)

Example 36

3,5-trans-7-Chloro-1-isobutyl-5-(2-methoxyphenyl)-2-oxo-1,2,3,5-tetrahydro-4,1-thieno[2,3-e] oxazepine-3-acetic acid

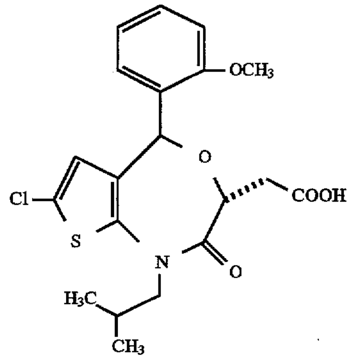

The trans-form ester (0.68 g) obtained in Example 35 was allowed to proceed in substantially the same manner as in Example 31 to give 0.22 g of colorless crystals, m.p. 183°–185° C.

Elemental Analysis for $C_{20}H_{22}ClNO_5S$: Calcd.: C, 56.67; H, 5.23; N, 3.30 Found: C, 56.40; H, 5.18; N, 3.29

Example 37

3,5-cis-7-Chloro-1-isobutyl-5-(2-methoxyphenyl)-2-oxo-1,2,3,5-tetrahydro-4,1-thieno[2,3-e]oxazepine-3-acetic acid

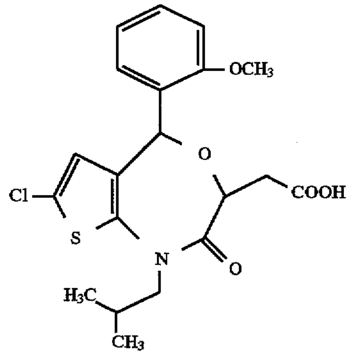

The cis-form ester (0.59 g) obtained in Example 35 was allowed to proceed in substantially the same manner as in Example 31 to give 0.27 g of a colorless solid matter, m.p. 144°–146° C.

Elemental Analysis for $C_{20}H_{22}ClNO_5S$: Calcd.: C, 56.67; H, 5.23; N, 3.30 Found: C, 56.94; H, 5.24; N, 3.58

Example 38

3,5-trans-7-Chloro-5-(2,3-dimethoxyphenyl)-1-neopentyl-2-oxo-1,2,3,5-tetrahydro-4,1-benzothiazepine-3-acetic acid methyl ester

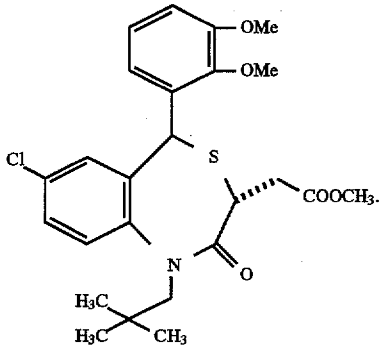

5-Chloro-α-(2,3-dimethoxyphenyl)-2-(neopentylamino) benzyl alcohol (1.0 g) and thiomalic acid (0.41 g) were subjected to substantially the same procedure as in Example 1 to give 0.38 g of colorless crystals, m.p. 193°–196° C.

Elemental Analysis for $C_{25}H_{30}ClNO_5S.0.3H_2O$: Calcd.: C, 60.36; H, 6.20; N, 2.86 Found: C, 60.43; H, 6.21; N, 2.75

Example 39

3,5-trans-7-Chloro-5-(2,3-dimethoxyphenyl)-1-neopentyl-2-oxo-1,2,3,5-tetrahydro-4,1-benzothiazepine-3-acetic acid

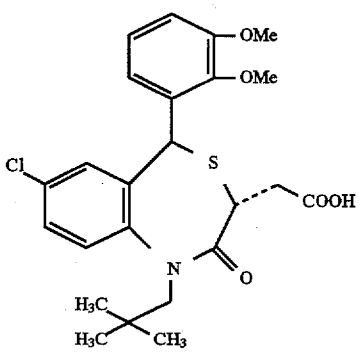

3,5-trans-7-Chloro-5-(2,3-dimethoxyphenyl)-1-neopentyl-2-oxo-1,2,3,5-tetrahydro-4,1-benzothiazepine-3-acetic acid methyl ester obtained in Example 38) (10 g) was subjected to substantially the same procedure as in Example 9 to give 7.7 g of colorless crystals, m.p. 263°–277° C.

Elemental Analysis for $C_{24}H_{28}ClNO_5S$: Calcd.: C, 60.31; H, 5.91; N, 2.93 Found: C, 60.03; H, 5.86; N, 2.84

Example 40

N-[(3R,5S)-7-Chloro-5-(2,3-dimethoxyphenyl)-1-neopentyl-2-oxo-1,2,3,5-tetrahydro-4,1-benzothiazepine-3-acetyl]-L-leucine methyl ester and N-[(3S,5R)-7-chloro-5-(2,3-dimethoxyphenyl)-1-neopentyl)-2-oxo-1,2,3,5-tetrahydro-4,1-benzothiazepine-3-acetyl]-L-leucine methyl ester

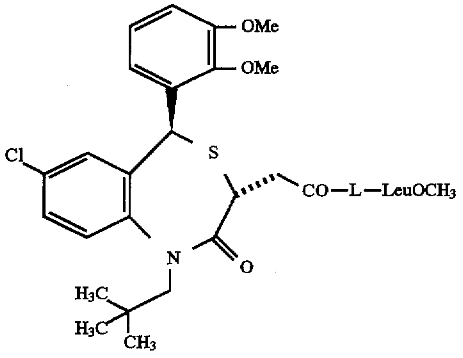

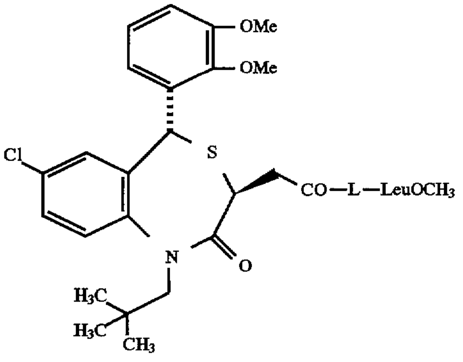

In dichloromethane (150 ml) were dissolved 3,5-trans-7-chloro-5-(2,3-dimethoxyphenyl)-1-neopentyl-2-oxo-1,2,3,5-tetrahydro-4,1-benzothiazepine-3-acetic acid (7.1 g) and L-leucine methyl ester (2.7 g). To the solution were added diethyl cyanophosphonate (3.6 g) and triethylamine (3.3 g). The mixture was stirred for 30 minutes at room temperature, which was then washed with 5% HCl, a saturated aqueous solution of sodium hydrogencarbonate and a saturated aqueous saline solution. The solvent was then distilled off, and the residue was purified by means of a silica-gel column chromatography (hexane:acetic acid ethyl ester=4:1–3:1 v/v as an eluent) to give 4.13 g of N-[(3R,5S)-7-chloro-5-(2,3-dimethoxyphenyl)-1-neopentyl-2-oxo-1,2,3,5-tetrahydro-4,1-benzothiazepine-3-acetyl]-L-leucine methyl ester from the first fraction as colorless crystals, m.p. 121°–123° C.

$[\alpha]_D^{22}$–235.2° (c=0.39, MeOH)

$^1$H-NMR($CDCl_3$) δ: 0.932(6H, t, J=6.2 Hz), 0.989 (9H,s), 1.49–1,67(3H,m), 2.322(1H,dd,J=3.2, 14.2 Hz), 2.97(1H, dd,J=10.6,14.2 Hz) 3.187(1H,d,J=14.0 Hz), 3.696(3H,s), 3.715(3H,s), 3.779(1H,dd,J=3.2,10,6 Hz), 3.889(3H,s), 4.420(1H,d,J=14,0 Hz), 4.47–4.59(1H,m), 6.05–6.10(1H, br), 6.270(1H,s), 6.814–7.400(6H,m).

From the second fraction was obtained 4.15 g of N-[(3S,5R)-7-chloro-5-(2,3-dimethoxyphenyl)-1-neopentyl-2-oxo-1,2,3,5-tetrahydro-4,1-benzothiazepine-3-acetyl]-L-leucine methyl ester as a non-crystalline solid product.

$[\alpha]_D^{22}$+178.6 deg. (c=0.47, MeOH)

$^1$H=NMR($CDCl_3$) δ: 0.89–0.92(6H,m), 0.996(9H,s), 1.51–1.66(3H,m), 2.323(1H,dd,J=4.2,14.4 Hz), 2.990(1H, dd,J=10.2,14.4 Hz), 3.226(1H,d,J=13.8 Hz), 3.69–3.78(7H, m), 3.890(3H,s), 4.44–4.54(2H,m), 6.281(1H,s), 6.37–6.41 (1H,br), 6.801–7.396(6H,m)

Example 41

(3R,5S)-7-Chloro-5-(2,3-dimethoxyphenyl)-1-neopentyl-2-oxo-1,2,3,5-tetrahydro-4,1-benzothiazepine-3-acetic acid methyl ester

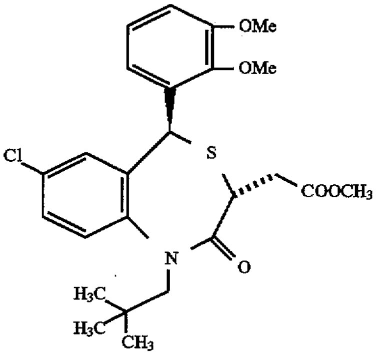

To a solution of N-[(3R,5S)-7-chloro-5-(2,3-dimethoxyphenyl)-1-neopentyl-2-oxo-1,2,3,5-tetrahydro-4,1-benzothiazepine-3-acetyl]-L-leucine methyl ester (4.13 g) obtained in Example 40 in methanol (100 ml). To the solution was added conc. HCl (50 ml), and the mixture was heated for 24 hours under reflux. The reaction mixture was subjected to extraction with dichloromethane, and the extract was dried over anhydrous sodium sulfate, then the solvent was distilled off. The residue was purified by means of a silica-gel column chromatography (acetic acid ethyl ester=3:1 v/v as an eluent). The solid product thus obtained was recrystallized from a mixture solvent of dichloromethane-petroleum ether to give 2.87 g of colorless crystals, m.p. 170°–171° C.

Example 42

(3S,5R)-7-Chloro-5-(2,3-dimethoxyphenyl)-1-neopentyl-2-oxo-1,2,3,5-tetrahydro-4,1-benzothiazepine-3-acetic acid methyl ester

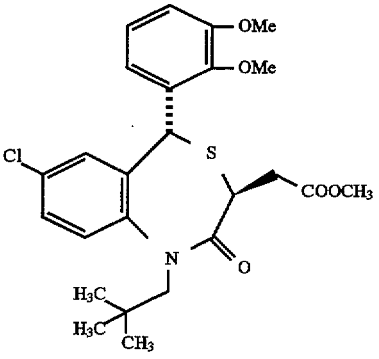

N-[(3S,5R)-7-Chloro-5-(2,3-dimethoxyphenyl)-1-neopentyl-2-oxo-1,2,3,5-tetrahydro-4,1-benzothiazepine-3-acetyl]-L-leucine methyl ester (4.15 g) obtained in Example 40 was subjected to substantially the same procedure as in Example 41 to give 2.70 g of colorless crystals, m.p. 168°–170° C.

Example 43

(3R,5S)-7-Chloro-5-(2,3-dimethoxyphenyl)-1-neopentyl-2-oxo-1,2,3,5-tetrahydro-4,1-benzothiazepine-3-acetic acid

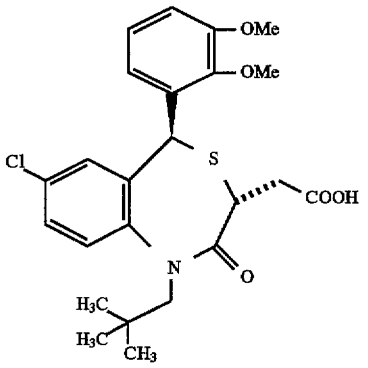

(3R,5S)-7-Chloro-5-(2,3-dimethoxyphenyl)-1-neopentyl-2-oxo-1,2,3,5-tetrahydro-4,1-benzothiazepine-3-acetic acid methyl ester (2.6 g) obtained in Example 41 was subjected to substantially the same procedure as in Example 9 to give 1.98 g of colorless crystals, m.p. 263°–271° C.

$[\alpha]_D^{22}$−303.5° (c=0.92, MeOH)

Elemental Analysis for $C_{24}H_{28}ClNO_5S$: Calcd.: C, 60.31; H, 5.90; N, 2.93 Found: C, 60.09; H, 6.08; N, 2.99

Example 44

(3S,5R)-7-Chloro-5-(2,3-dimethoxyphenyl)-1-neopentyl-2-oxo-1,2,3,5-tetrahydro-4,1-benzothiazepine-3-acetic acid

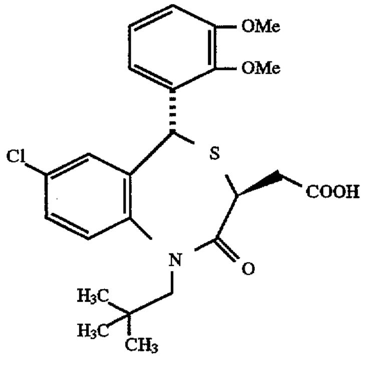

(3S,5R)-7-Chloro-5-(2,3-dimethoxyphenyl)-1-neopentyl-2-oxo-1,2,3,5-tetrahydro-4,1-benzothiazepine-3-acetic acid methyl ester (2.5 g) obtained in Example 42 was subjected to substantially the same procedure as in Example 9 to give 1.88 g of colorless crystals, m.p. 261°–270° C.

$[\alpha]_D^{22}$+290.2° (c=0.61, MeOH)

Elemental Analysis for $C_{24}H_{28}ClNO_5S$: Calcd.: C, 60.31; H, 5.90; N, 2.93 Found: C, 60.13; H, 5.89; N, 2.97

Example 45

3.5-trans-7-Chloro-5-(2,4-dimethoxyphenyl)-1-neopentyl-2-oxo-1,2,3,5-tetrahydro-4,1-benzothiazepine-3-acetic acid methyl ester

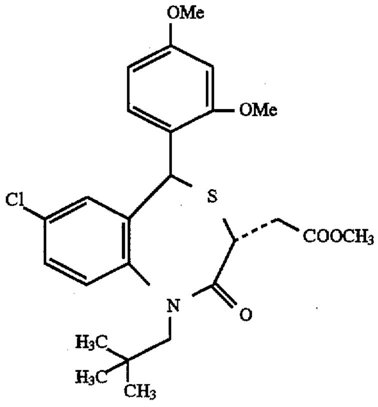

5-Chloro-α-(2,4-dimethoxyphenyl)-2-(neopentyl amino) benzyl alcohol (38.9 g) and thiomalic acid (16.1 g) were subjected to substantially the same procedure as in Example 1 to give 32.5 g of colorless crystals, m.p. 190°–191° C.

Elemental Analysis for $C_{25}H_{30}ClNO_5S$: Calcd.: C, 61.03; H, 6.15; N, 2.85 Found: C, 60.95; H, 6.12; N, 2.75

Example 46

3,5-trans-7-Chloro-5-(2,4-dimethoxyphenyl)-1-neopentyl-2-oxo-1,2,3,5-tetrahydro-4,1-benzothiazepine-3-acetic acid

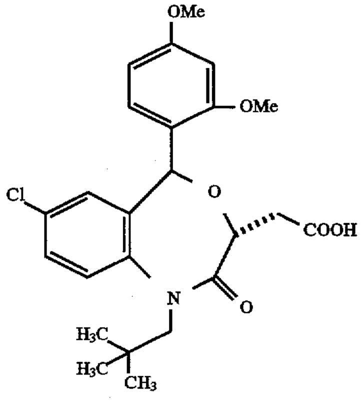

3,5-trans-7-Chloro-5-(2,4-dimethoxyphenyl)-1-neopentyl-2-oxo-1,2,3,5-tetrahydro-4,1-benzothiazepine-3-acetic acid methyl ester (27 g) obtained in Example 45 was subjected to substantially the same procedure as in Example 9 to give 26.6 g of colorless crystals, m.p. 157°–160° C.

Elemental Analysis for $C_{24}H_{28}ClNO_5S$: Calcd.: C, 60.31; H, 5.91; N, 2.93 Found: C, 60.57; H, 5.83; N, 2.66

Example 47

N-[(3S,5R)-7-Chloro-5-(2,4-dimethoxyphenyl)-1-neopentyl-2-oxo-1,2,3,5-tetrahydro-4,1-benzothiazepine-3-acetyl]-L-alanine tert-butyl ester and N-[(3R,5S)-7-chloro-5-(2,4-dimethoxyphenyl)-4-neopentyl-2-oxo-1,2,3,5-tetrahydro-4,1-benzothiazepine-3-acetyl]-L-alanine tert-butyl ester

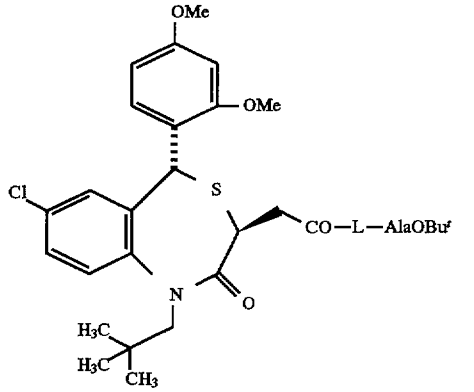

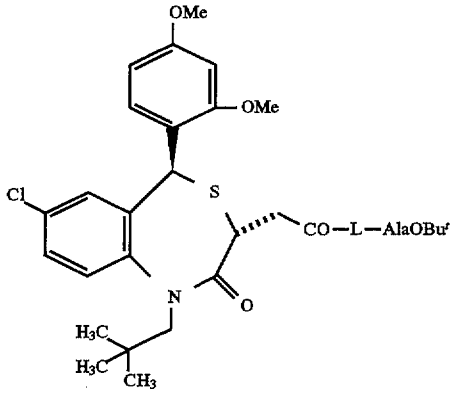

3,5-trans-7-Chloro-5-(2,4-dimethoxyphenyl)-1-neopentyl-2-oxo-1,2,3,5-tetrahydro-4,1-benzothiazepine-3-acetic acid (15 g) and L-alanine tert-butyl ester hydrochloride (6.0 g) were subjected to substantially the same procedure as in Example 40 to give 6.31 g of N-[3S,5R)-7-chloro-5-(2,4-dimethoxyphenyl)-1-neopentyl-2-oxo-1,2,3,5-tetrahydro-4,1-benzothiazepine3-acetyl]-L-alanine tert-butyl ester as a non-crystalline solid product from the first fraction.

$^1$H-NMR($CDCl_3$) δ: 0.975(9H,s), 1.322(3H,d,J=7.0 Hz), 1.463(9H,s), 2.300(1H,dd,J=3.8,14.6 Hz), 2.993(1H,dd,J=10.0, 14.6 Hz), 3.205(1H,d,J=13.8 Hz), 3.663(3H,s), 3.713 (1H,dd,J=3.8,10.0 Hz), 3.858(3H,s), 4.358(1H,q,J=7.0 Hz), 4.472(1H,d,J=13.8 Hz), 6.243(1H,s), 6.471(1H,d,J=2.4 Hz), 6.606(1H,dd,J=2.4, 8.4 Hz), 6.836(1H,d,J=1.8 Hz), 7.264 (2H,m), 7.624(1H,d,J=8.6 Hz)

From the second fraction was obtained 7.91 g of N-[(3R, 5S)-7-chloro-5-(2,4-dimethoxyphenyl)-1-neopentyl-2-oxo-1,2,3,5-tetrahydro-4,1-benzothiazepine-3-acetyl]-L-aalanine tert-butyl ester as a non-crystalline solid product.

$^1$H-NMR($CDCl_3$) δ: 0.968(9H,s), 1.338(3H,d,J=7.0 Hz), 1.440(9H,s), 2.332(1H,dd,J=3.6,15.2 Hz), 2.937(1H,dd,J=10.4,15.2 Hz), 3.186(1H,d,J=13.8 Hz), 3.660(3H,s), 3.781 (1H,dd,J=3.6,10.4 Hz), 4.369(1H,q,J=7.0 Hz), 4.447(1H,d, J=13.8 Hz), 6.240(1H,s), 6.470(1H,d,J=2.4 Hz), 6.603(1H, dd,J=2.4, 8.6 Hz), 6.841(1H,s), 7.264(2H,m), 7.629(1H,d, J=8.6 Hz)

Example 48

(3S,5R)-7-Chloro-5-(2,4-dimethoxyphenyl)-1-neopentyl-2-oxo-1,2,3,5-tetrahydro-4,1-benzothiazepine-3-acetic acid methyl ester

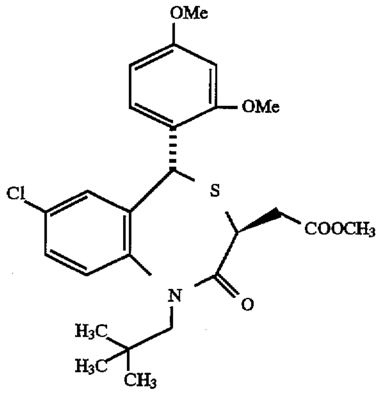

N-[(3S,5R)-7-chloro-5-(2,4-dimethoxyphenyl)-1-neopentyl-2-oxo-1,2,3,5-tetrahydro-4,1-benzothiazepine-3-acetyl]-L-alanine tert-butyl ester (6.31 g) obtained in Example 47 was subjected to substantially the same procedure as in Example 41 to give 4.0 g of colorless crystals, m.p. 187°–188° C.

Example 49

(3R,5S)-7-Chloro-5-(2,4-dimethoxyphenyl)-1-neopentyl-2-oxo-1,2,3,5-tetrahydro-4,1-benzothiazepine-3-acetic acid methyl ester

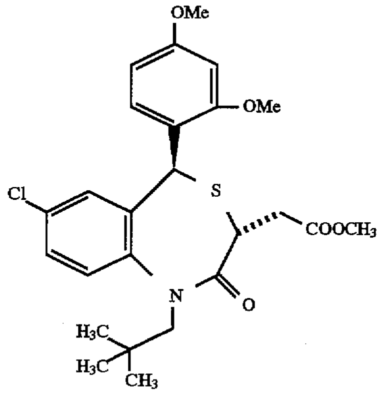

N-[(3R,5S)-7-Chloro-5-(2,4-dimethoxyphenyl)-1-neopentyl-2-oxo-1,2,3,5-tetrahydro-4,1-benzothiazepine-3-acetyl]-L-alanine tert-butyl ester (7.91 g) obtained in Example 47 was subjected to substantially the same procedure as in Example 41 to give 3,89 g of colorless crystals, m.p. 188°–190° C.

Example 50

(3S,5R)-7-Chloro-5-(2,4-dimethoxyphenyl)-1-neopentyl-2-oxo-1,2,3,5-tetrahydro-4,1-benzothiazepine-3-acetic acid

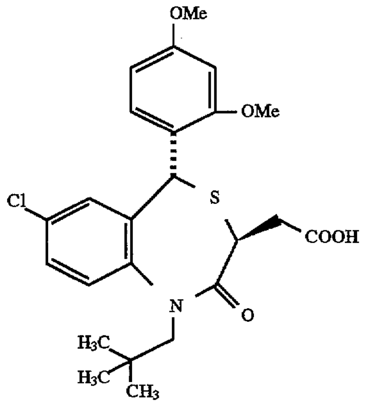

(3S,5R)-7-Chloro-5-(2,4-dimethoxyphenyl)-1-neopentyl-2-oxo-1,2,3,5-tetrahydro-4,1-benzothiazepine-3-acetic acid methyl ester (3.5 g) obtained in Example 48 was subjected to substantially the same procedure as in Example 9 to give 3.22 g of colorless crystals, m.p. 147°–151° C.

$[\alpha]_D^{22}$+255.9° (c=0.35, MeOH)

Elemental Analysis for $C_{24}H_{28}ClNO_5S$: Calcd.: C, 60.31; H, 5.91; N, 2.93 Found: C, 60.58; H, 5.82; N, 2.79

Example 51

(3R,5S)-7-Chloro-5-(2,4-dimethoxyphenyl)-1-neopentyl-2-oxo-1,2,3,5-tetrahydro-4,1-benzothiazepine-3-acetic acid

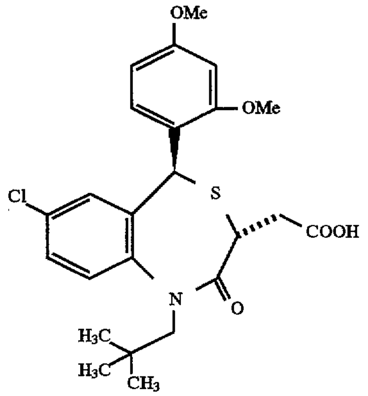

(3R,5S)-7-Chloro-5-(2,4-dimethoxyphenyl)-1-neopentyl-2-oxo-1,2,3,5-tetrahydro-4,1-benzothiazepine-3-acetic acid methyl ester (3.37 g) obtained in Example 49 was processed in substantially the same manner as in Example 9 to give 3.28 g of colorless crystals, m.p. 148°–152° C.

$[\alpha]_D^{22}$–252.3° (c=0.47, MeOH)

Elemental Analysis for $C_{24}H_{28}ClNO_5S$: Calcd.: C, 60.31; H, 5.91; N, 2.93 Found: C, 60.32; H, 5.83; N, 2.87

Example 52

7-Chloro-5-(2-chlorophenyl)-1-neopentyl-2-oxo-1,2,4,5-tetrahydro-3H-1,3-benzodiazepine-3-acetic acid methyl ester

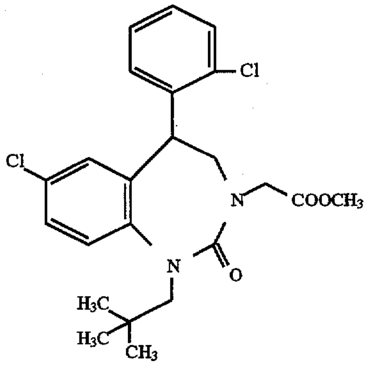

(1) α-(5-Chloro-2-nitrophenyl)-2-chlorophenylacetic acid methyl ester

A solution of sodium hydride (3.4 g), 2-chlorophenyl acetic acid methyl ester (28.3 g) and 4-chloro-1,2-dinitrobenzene (27 g) in dimethylformamide (100 ml) was stirred for one hour at 0° C. The reaction mixture was added to dilute hydrochloric acid (300 ml), followed by extraction with acetic acid ethyl ester. The extract solution was washed with a saturated aqueous saline solution, dried over anhydrous sodium sulfate, and, then the solvent was distilled off. The residual oily product was purified by means of a silica-gel column chromatography (hexane:acetic acid ethyl ester=10:1 v/v as an eluent), followed by recrystallization from hexane to give 26.3 g of yellow crystals, m.p. 96°–97° C.

Elemental Analysis for $C_{15}H_{11}Cl_2NO_4$: Calcd.: C, 52.96; H, 3.26; N, 4.12 Found: C, 53.04; H, 3.34; N, 4.06

(2) 2-(2-Nitro-5-chlorophenyl)-2-(2-chlorophenyl)ethanol

A mixture solution of α-(5-chloro-2-nitrophenyl)-2-chlorophenyl acetic acid methyl ester (26.3 g) and lithium borohydride (2 g) in tetrahydrofuran (200 ml) was stirred for 4 hours at room temperature. This mixture solution was added to a 20% aqueous solution of acetic acid (50 ml), which was extracted with acetic acid ethyl ester. The extract solution was washed with water, dried over anhydrous sodium sulfate and, then, the solvent was distilled off. The residual oily compound was purified by means of a silica-gel column chromatography to give 11.0 g of an oily compound.

$^1$H-NMR($CDCl_3$) δ: 1.90(1H,br), 4.15–4.33(2H,m), 5.270 (1H,t,J=6.2 Hz), 7.20–7.40(6H,m), 7.867(1H,d,J=8.4 Hz)

(3) α-(5-Chloro-2-nitrophenyl)-2-chlorophenyl acetaldehyde

A solution of dimethyl sulfoxide (6.7 ml) in dichloromethane (30 ml) was added to a solution of oxatyl chloride (6.2 ml) in dichloromethane (300 ml) at –78° C. The mixture was stirred for further 10 minutes at –78° C. To the solution was added a solution of 2-(2-nitro-5-chlorophenyl)-2-(2-chlorophenyl)ethanol (11.04 g) in dichloromethane (100 ml) at –78° C., and the mixture was stirred for further 15 minutes at –78° C.

To the reaction mixture was added triethylamine (37 ml), which was warmed up to 0° C., to which was added a saturated aqueous solution of ammonium chloride (124 ml). The organic layer was washed with water, dried over anhydrous sodium sulfate and, then, the solvent was distilled off. The residual oily compound was purified by means of a silica-gel column chromatography (hexane: acetic acid ethyl ester=3:1 v/v as an eluent) to give 9.15 g of an oily compound.

$^1$H-NMR($CDCl_3$) δ: 6.299(1H,s), 6.836(1H,d,J=2.2 Hz), 7.14–7.65(5H,m), 8.096(1H,d,J=88 Hz), 9.887(1H,s)

(4) N-[2-(2-Chlorophenyl)-2-(2-nitro-5-chlorophenyl)ethyl] glycine methyl ester

To a solution of α-(5-chloro-2-nitrophenyl)-2-chlorophenylacetaldehyde (1.68 g) in methanol(15 ml) were added glycine methyl ester hydrochloride (0.69 g) and sodium acetate (0.45 g). The mixture was stirred for 30 minutes at room temperature, to which was added sodium cyanoborohydride (0.35 g). To this mixture was added hydrogen chloride for 5 minutes. This mixture solution was stirred for 3 hours at 50° C., to which was added a 1N aqueous solution of sodium hydroxide (50 ml), followed by extraction with dichloromethane. The extract solution was washed with water, then the solvent was distilled off. The residual oily product was purified by means of a silica-gel column chromatography (hexane:acetic acid ethyl ester=3:1 v/v as an eluent) to give 1.1 g of an oily compound.

$^1$H-NMR($CDCl_3$) δ: 3.200(1H,dd,J=6.8,12.2 Hz), 3.366 (1H,dd,J=7.6,12.2 Hz), 3.482(2H,s), 3.731(3H,s), 5.255(1H, t,J=7.2 Hz), 7.22–7.44(6H,m), 7.846(1H,d,J=8.6 Hz)

(5) N-[2-(2-chlorophenyl)-2-(2-nitro-5-chlorophenyl)ethyl] -N-(trifluoroacetyl)glycine methyl ester To a solution of N-[2-(2-chlorophenyl)-2-(2-nitro-5-chlorophenyl)ethyl]glycine methyl ester (4.9 g) and pyridine (3.0 g) in dichloromethane (50 ml) was added trifluoroacetic anhydride (2.97 g), and the mixture was stirred for 10 minutes at room temperature. The solution was washed with a 1N aqueous solution of sodium hydroxide and a saturated aqueous saline solution, which was then dried over anhydrous sodium sulfate. The solvent was then distilled off, and the residue was purified by means of a silica-gel column chromatography (hexane:acetic acid ethyl ester=5:1 v/v as an eluent) to give 5.95 g of an oily compound.

$^1$H-NMR($CDCl_3$) δ: 3.786(3H,s), 4.138(1H,dd,J=7.0, 14.0 Hz), 4.215(2H,s), 4.434(1H,dd,J=8.8, 14.0 Hz), 5.473 (1H,dd,J=7.0, 8.8 Hz), 7.27–7.52(6H,m), 7.874(1H,d,J=8.4 Hz)

(6) N-[2-(2-Amino-5-chlorophenyl)-2-(2-chlorophenyl) ethyl]-N-(trifluoroacetyl)glycine methyl ester To a solution of N-[2-(2-chlorophenyl)-2-(2-nitro-5-chlorophenyl)ethyl]-N-(trifluoroacetyl)glycine methyl ester (1 g) in acetic acid ethyl ester (20 ml) was added 10% Pd/C catalyst (100 mg). The mixture was subjected to catalytic reduction at ambient temperature under atmospheric pressure. After the reaction, the catalyst was removed and the solvent was distilled off. The residue was purified by means of a silica-gel column chromatography (hexane:acetic acid ethyl ester=4:1 v/v as an eluent) to give 0.39 g of an oily compound.

$^1$H-NMR($CDCl_3$) δ: 3.705 (¼×3H,s), 3.742 (¾×3H,s), 3.473–4.247(4H,m), 4.72–4.80(¼×1H,m), 4.874(¾×1H, dd, J=5.8, 9.4 Hz), 6.57–6.63(7H,m), 7.05–7.44(6H,m)

(7) N-[2-(5-Chloro-2-neopentylaminophenyl)-2-(2-chlorophenyl)ethyl]-N-trifluoroacetylglycine methyl ester To a solution of N-[2-(2-amino-5-chlorophenyl)-2-(2-chlorophenyl)ethyl]-N-(trifluoroacetyl)glycine methyl ester (0.39 g) in methanol (5 ml) were added acetic acid (0.05 ml) and pivalaldehyde (78 mg). The mixture was stirred for 30 minutes at room temperature, to which was added sodium cyanoborohydride (57 mg). The mixture was stirred for one hour at room temperature, followed by addition of dichloromethane (50 ml) thereto. This solution was washed with a 1N aqueous solution of sodium hydroxide, then with water, followed by distilling off the solvent. The residue was purified by means of a silica-gel column chromatography (hexane:acetic acid ethyl ester=5:1 v/v as an eluent) to give 0.27 g of an oily compound.

$^1$H-NMR($CDCl_3$) δ: 0.851(9H,s), 2.65–2.83(2H,m), 3.316(¼×1H,d,J=17.4 Hz), 3.51–3.60(1H,m), 3.702(¼×3H, s), 3.748(¾×3H,s), 3.873(1H,dd,J=9.8, 13,4 Hz), 4.055(¾×1H,d,J=17.9 Hz), 4.274(1H,dd,J=5.8, 13.4 Hz), 4.72–4.86 (1H,m), 6.53–6.60(1H,m), 7.11–7.40(6H,m)

(8) N-[2-(5-Chloro-2-neopentylaminophenyl)-2-(2-chlorophenyl)ethyl]glycine methyl ester To a solution of N-[2-(5-chloro-2-neopentylamino phenyl)-2-(2-chlorophenyl)ethyl]-N-trifluoroacetylglycine methyl ester (0.2 g) in methanol (3 ml) was added conc. hydrochloric acid (0.6 ml), which was heated under reflux for one day. To the reaction mixture was added a 1N aqueous solution of sodium hydroxide (8ml), followed by extraction with dichloromethane. The extract solution was washed with water, then the solvent was distilled off to leave 72 mg of an oily compound.

$^1$H-NMR($CDCl_3$) δ: 0.823(9H,s), 2.659(1H,d), J=11.2 Hz), 2.769(1H,d,J=11.2 Hz), 3.029(1H,dd,J=5.2,11.8 Hz), 3.279(1H,dd,J=8.4,11.8 Hz), 3.427(1H,d,17.6 Hz), 3.528 (1H,d,J=17.6 Hz), 3.741(3H,s), 4.563(1H,dd,J=5.2, 8.4 Hz), 6.538(1H,d,J=8.8 Hz), 6.99–7.42(6H,m)

(9) 7-Chloro-5-(2-chlorophenyl)-1-neopentyl-2-oxo-1,2,3, 5-tetrahydro-3H-1,3-benzodiazepine-3-acetic acid methyl ester To a solution of N-[2-(5-chloro-2-neopentylaminophenyl) -2-(2-chlorophenyl)ethyl]glycine methyl ester (0.47 g) and triethylamine (0.21 g) in toluene (5 ml) was added triphosgene (0.14 g). The mixture was heated for 5 hours at 70° C. To the reaction mixture was added dichloromethane (50 ml), which was washed with 1N hydrochloric acid and water, then the solvent was distilled off. The residue was recrystallized from hexane to give 0.30 g of colorless crystals, m.p. 142°–148° C.

$^1$H-NMR($CDCl_3$) δ: 0.940(9H,s), 3.492(1H,d,J=14.4 Hz), 3.639(1H,d,J=17.2 Hz), 3.715(3H,s), 3.876(2H,d,J=8.6 Hz), 4.038(1H,d,J=17.2 Hz), 4.308(1H,d,J=14.4 Hz), 5.317(1H, d,J=8.6 Hz), 6.645(1H,d,J=1.8 Hz), 7.14–7.50(6H,m)

Example 53

7-Chloro-5-(2-chlorophenyl)-1-neopentyl-2-oxo-1,2,4,5-tetrahydro-3H-1,3-benzodiazepine-3-acetic acid

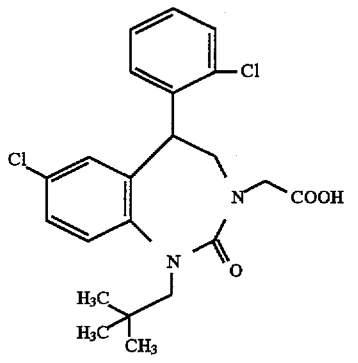

7-Chloro-5-(2-chlorophenyl)-1-neopentyl-2-oxo-1,2,4,5-tetrahydro-3H-1,3-benzodiazepine-3-acetic acid methyl ester (0.30 g) was processed in substantially the same manner as in Example 9 to give 0.21 g of colorless crystals, m.p. 228°–231° C.

Elemental Analysis for $C_{22}H_{24}Cl_2N_2O_3$: Calcd.: C, 60.70; H, 5.56; N, 6.43 Found: C, 60.37; H, 5.49; N, 6.15

Example 54

3,6-trans-8-Chloro-6-(2-chlorophenyl)-1-neopentyl-2-oxo-2,3,5,6-tetrahydro-1H-4,1-benzoxazocine-3-acetic acid ethyl ester

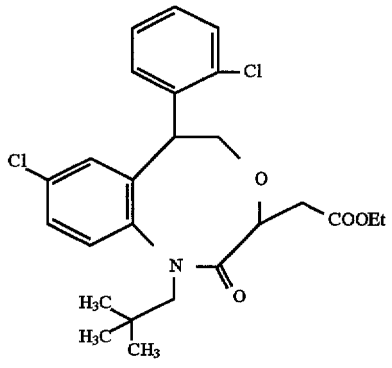

(1) 2-(2-Amino-5-chlorophenyl)-2-(2-chlorophenyl)ethanol

To a solution of 2-(2-nitro-5-chlorophenyl)-2-(2-chlorophenyl)ethanol (7.0 g) obtained in Example 52-(2) in ethanol (70 ml) were added hydrazine hydrate (3.4 g) and Raney's nickel (0.1 g). The mixture was stirred for 30 minutes at room temperature. The catalyst was removed, and the solvent was distilled off. The residue was purified by means of a silica-gel column chromatography (hexane:acetic acid ethyl ester=2:1 v/v as an eluent) to give 4.44 g of an oily compound.

$^1$H-NMR($CDCl_3$) δ: 4.107(2H,d,J=6.6 Hz), 4.587(1H,t, J=6.6 Hz), 6.597(1H,d,J=8.4 Hz), 7.01–7.43(6H,m)

(2) 2-(5-Chloro-2-neopentylaminophenyl)-2-(2-chlorophenyl)ethanol

To a solution of 2-(2-amino-5-chlorophenyl)-2-(2-chlorophenyl)ethanol (4.44 g) in methanol (50 ml) were added acetic acid (1.4 ml) and pivalaldehyde (2.0 g). The mixture was stirred for 30 minutes at room temperature. To the solution was added sodium cyano borohydride (1.5 g), and the mixture was stirred for one hour at room temperature. The reaction mixture was then processed in substantially the same manner as in Example 52-(7) to give 5.5 g of an oily compound.

$^1$H-NMR($CDCl_3$) δ: 0.813(9H,s), 2.654(1H,d,J=11.4 Hz), 2.766(1H,d,J=11.4 Hz), 4.11–4.15(2H,m), 4.590(1H,t,J=6.3 Hz), 6.549(1H,d,J=8.6 Hz), 7.01–7.44(6H,m)

(3) 3-[N-[2-[1-(2-Chlorophenyl)-2-hydroxyethyl]-4-chlorophenyl]-N-neopentylcarbamoyl]acrylic acid ethyl ester To dichloromethane (300 ml) were added 2-(5-chloro-2-neopentylaminophenyl)-2-(2-chlorophenyl)ethanol (5.5 g) and sodium hydrogencarbonate (1.7 g). To the mixture was added fumaric chloride monoethyl ester (2.6 g), which was stirred for one hour at room temperature. To the reaction mixture was added dichloromethane (100 ml), which was washed with water and dried over anhydrous sodium sulfate. The solvent was then distilled off. The residue was purified by means of a silica-gel column chromatography (hexane:acetic acid ethyl ester=5:1 v/v as an eluent) to give 6.9 g of an oily compound.

$^1$H-NMR($CDCl_3$) δ: 0.679(½×9H,s), 0.941(½×9H,s), 1.210(½×3H,t,J=7.2 Hz), 1.249(½×3H,t,J=7.2 Hz), 2.300 (½×1H,d,J=13.8 Hz), 2.879(½×1H,d,J=13.4 Hz), 3.96–4.29 (4H,½1H,m), 4.60–4.67(1H,m), 4 821(½×1H,t,J=7.0 Hz), 5.863(½×1H,d,J=15.2 Hz), 6.167(½×1H,d,J=15.2 Hz), 6.69–7.81(8H,m)

(4) 8-Chloro-6-(2-chlorophenyl)-1-neopentyl-2-oxo-2,3,5,6-tetrahydro-1H-4,1-benzoxazocine-3-acetic acid ethyl ester To dichloromethane (70 ml) were added 3-[N-[2-[1-(2-chlorophenyl)-2-hydroxyethyl]-4-chlorophenyl]-N-neopentylcarbamoyl]acrylic acid ethyl ester (6.8 g), 18-crown-6 (3.78 g) and potassium carbonate. The mixture was stirred for 3 days at room temperature. Insolubles were filtered off, then the solvent was distilled off. The residue was purified by means of a silica-gel column chromatography (hexane:acetic acid ethyl ester=5:1 v/v as an eluent) to give 1.64 g of a non-crystalline solid product.

$^1$H-NMR($CDCl_3$) δ: 1.028(9H,s), 1.227(3H,t,J=7.2 Hz), 2.740(1H,dd,J=6.6,17.2 Hz), 2.974(1H,dd,J=7.8,17.2 Hz), 3.716(1H,d,J=13.4 Hz), 3.94–4.14(5H,m), 4.417(1H,dd,J=1.4,11,4 Hz), 4.671(1H,dd,J=1.4, 8.8 Hz), 7.014(1H,d,J=2.2 Hz), 7.23–7.43(6H,m)

Example 55

3,6-trans-8-Chloro-6-(2-chlorophenyl)-1-neopentyl-2-oxo-2,3,5,6-tetrahydro-1H-4,1-benzoxazocine-3-acetic acid

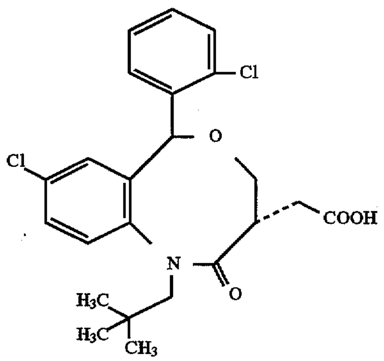

3,6-trans-8-Chloro-6-(2-chlorophenyl)-1-neopentyl-2-oxo-2,3,5,6-tetrahydro-1H-4,1-benzoxazocine-3-acetic acid ethyl ester (1.2 g) obtained in Example 54 was subjected to substantially the same procedure as in Example 9 to give 0.23 g of colorless crystals, m.p. 127°–133° C.

Elemental Analysis for $C_{23}H_{25}Cl_2NO_4.H_2O$: Calcd.: C, 58.98; H, 5.81; N, 2.99 Found: C, 58.82; H, 5.43; N, 2.97

Example 56

7-Chloro-5-(2-chlorophenyl)-1-neopentyl-1,2 -dihydro-2-oxo-3H-1,3,4-benzotriazepine-3-acetic acid ethyl ester

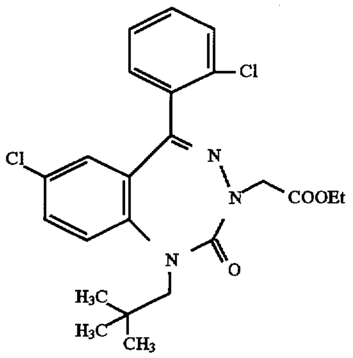

(1) 5-Chloro-2-neopentylaminophenyl 2-chlorophenyl thioketone

To a solution of 2-amino-2',5-dichlorobenzophenone (10 g) in methanol (50 ml) were added pivalaldehyde (3.4 g) and acetic acid (5 ml). The mixture was stirred for 30 minutes at 0° C. To this solution was added sodium cyanoborohydride (3.1 g), and the mixture was stirred for one day at 60° C. The solution was concentrated, to which was added dichloromethane (100 ml). The mixture was washed with water and dried over anhydrous sodium sulfate. Then, the solvent was distilled off, and the residue was purified by means of a silica-gel column chromatography (hexane:acetic acid ethyl ester=20:1 v/v as an eluent) to give 6.3 g of a yellow solid compound. To a solution of this compound (0.5 g) in toluene (5 ml) was added a Lawesson's reagent (0.3 g), and the mixture was heated for two hours under reflux. To the reaction mixture was added acetic acid ethyl ester (50 ml), which was washed with water and then dried over anhydrous sodium sulfate. The solvent was distilled off to leave 0.54 g of a reddish oily compound.

(2) 2-Neopentylamino-2',5-dichlorobenzophenone ethoxycarbonylmethyl hydrazone

To a solution of 5-chloro-2-neopentylaminophenyl 2-chlorophenyl thioketone (0.54 g) in ethanol (7 ml) was added ethyl hydrazinoacetate hydrochloride (0.11 g). The mixture was stirred for one day at 70° C. To the reaction mixture was added dichloromethane (50 ml), which was washed with water and, then, dried over anhydrous sodium sulfate. The solvent was distilled off. The residue was purified by means of a silica-gel column chromatography (hexane:acetic acid ethyl ester=15:1 v/v as an eluent) to give 0.16 g of an oily product.

$^1$H-NMR($CDCl_3$) δ: 0.95(9H,s), 1.273(3H,t,J=7.2 Hz), 2.964(2H,d,J=5.8 Hz), 4.04–4.27(4H,m), 5.969(1H,t,J=5.8 Hz), 6.681(1H,d,J=9.0 Hz), 6.879(1H,d,J=2.6 Hz), 7.15–7.50(5H,m)

(3) 7-Chloro-5-(2-chlorophenyl)-1-neopentyl-1,2-dihydro-2-oxo-3H-1,3,4-benzotriazepine-3-acetic acid ethyl ester To a solution of 2-neopentylamino-2',5-dichlorobenzophenone ethoxycarbonyl methyl hydrazone (0.16 g) and triethylamine (90 mg) in toluene (2 ml) was added triphosgene (54 mg). The mixture was stirred for one hour at 70° C., to which was added acetic acid ethyl ester (50 ml). The mixture was washed with water and, then dried over anhydrous sodium sulfate. The solvent was then distilled off. The residue was purified by means of a silica-gel column chromatography (hexane:acetic acid ethyl ester=3:1 v/v as an eluent) to give 0.16 g of an oily compound.

$^1$H-NMR($CDCl_3$) δ: 0.883(9H,s), 1.238(3H,t,J=7.0 Hz), 3,376(1H,d,J–14.0 Hz), 4.184(2H,q,J=7.0 Hz), 4.319(1H,d, J=16.8 Hz), 4.363(1H,d,J=14.0 Hz), 4.484(1H,d,j=16.8 Hz), 6.857(1H,d,J=2.6 Hz), 7.20–7.50(6H,m)

Example 57

7-Chloro-5-(2-chlorophenyl)-1-neopentyl-1,2-dihydro-2-oxo-3H-1,3,4-benzotriazepine-3-acetic acid

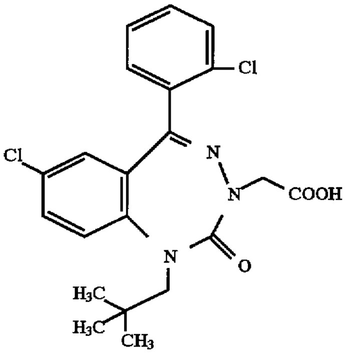

To a solution of 7-chloro-5-(2-chlorophenyl)-1-neopentyl-1,2-dihydro-2-oxo-3H-1,3,4-benzotriazepine-3-acetic acid ethyl ester obtained in Example 56 (0.16 g) in ethanol (3 ml) was added a 1N aqueous solution of sodium hydroxide (0.3 ml). The mixture was stirred for 4 hours at room temperature. To the reaction mixture was added water (50 ml), which was made acid with 1N HCl, then the solution was concentrated. To the concentrate was added dichloromethane (50 ml), which was washed with water, then the solvent was distilled off. The residue was recrystallized from dichloromethane—petroleum ether to give 91 mg of colorless crystals, m.p. 181°–183° C.

Elemental Analysis for $C_{21}H_{21}Cl_2N_3O_3$: Calcd.: C, 58.07; H, 4.87; N, 9.67 Found: C, 57.90; H, 5.13; N, 9.46

Example 58

3,5-trans-7-Chloro-5-(2,4-dimethoxyphenyl)-1-neopentyl-3-(tetrazol-5-yl)methyl-1,2,3,5-tetrahydro-4,1-benzothiazepin-2-one

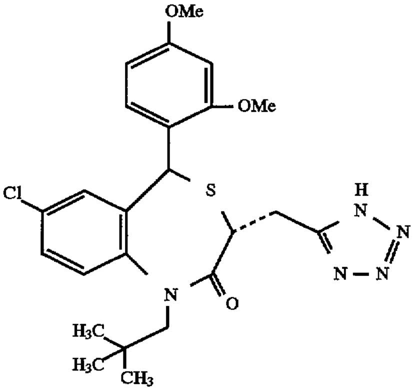

(1) 3-[3,5-trans-7-Chloro-5-(2,4-dimethoxyphenyl)-1-neopentyl-2-oxo-1,2,3,5-tetrahydro-4,1-benzothiazepine-3-acetylamino]propionitrile To a solution of 3,5-trans-7-chloro-5-(2,4-dimethoxyphenyl)-1-neopentyl-2-oxo-1,2,3,5-tetrahydro-4, 1-benzothiazepine-3-acetic acid obtained in Example 46 (1 g) and 3-aminopropionitrile (150 mg) in dichloromethane (10 ml) were added diethyl cyanophosphonate (340 mg) and triethylamine (320 mg). The mixture was stirred for 10 minutes at room temperature. To the reaction mixture was added dichloromethane (100 ml), which was washed with a 1N aqueous solution of NaOH and water, then dried over anhydrous sodium sulfate. The solvent was distilled off, and the residue was recrystallized from hexane to give 1.07 g of colorless crystals, m.p. 83°–103° C.

Elemental Analysis for $C_{27}H_{32}ClN_3O_4S$: Calcd.: C, 61.18; H, 6.08; N, 7.93 Found: C, 61.41; H, 6.11; N, 7.84

(2) 3,5-trans-7-Chloro-3-[1-(2-cyanoethyl)tetrazol-5-yl]methyl-5-(2,4-dimethoxyphenyl)-1-neopentyl-1,2,3,5-tetrahydro-4,1-benzothiazepin-2-one 3-[3,5-trans-7-Chloro-5-(2,4-dimethoxyphenyl)-1-neopentyl-2-oxo-1,2,3,5-tetrahydro-4,1-benzothiazepine-3-acetylamino]propionitrile (0.1 g), triphenylphosphine (99 mg), diethyl azodicarboxylate (66 mg) and trimethyl silyl azide (44 mg) in tetrahydrofuran (2 ml) was stirred for one day at room temperature. The reaction mixture was concentrated under reduced pressure. The concentrate was purified by means of a silica-gel column chromatography (hexane:acetic acid ethyl ester=1:1 v/v as an eluent) to give 59 mg of a non-crystalline solid compound.

$^1$H-NMR($CDCl_3$) δ: 0.938(9H,s), 2.96–3.16(4H,m), 3.17–3.52(1H,m), 3.667(3H,s), 3.867(3H,s), 3.92–3.99(1H, m), 4.16–4.28(1H,m), 4.73–4.81(2H,m), 6.290(1H,s), 6.49–7.65(6H,m)

(3) 3,5-trans-7-Chloro-5-(2,4-dimethoxyphenyl)-1-neopentyl-3-(tetrazol-5-yl)methyl-1,2,3,5-tetrahydro-4,1-benzothiazepin-2-one In a mixture solvent of methanol (1 ml) and tetrahydrofuran (1 ml) was dissolved 3,5-trans-7-chloro-3-[1-(2-cyanoethyl)tetrazol-5-yl]methyl-5-(2,4-dimethoxyphenyl)-1-neopentyl-1,2,3,5-tetrahydro-4,1-benzothiazepin-2-one (59 mg). To the solution was added a 1N aqueous solution of sodium hydroxide (0.11 ml), which was stirred for 6 hours at room temperature. To the reaction mixture was added water (50 ml). The solution was made acid, followed by extraction with dichloromethane. The extract solution was washed with a saturated aqueous solution of ammonium chloride, which was then dried on anhydrous sodium sulfate. The solvent was distilled off, and the residue was recrystallized from dichloromethane to give 26 mg of colorless crystals, m.p. 168°–173° C.

Elemental Analysis for $C_{24}H_{28}ClN_5O_3S$: Calcd.: C, 57.42; H, 5.62; N, 13.95 Found: C, 57.28; H, 5.22; N, 13.84

Example 59

(3R,5S)-7-Chloro-5-(2,3-dimethoxyphenyl)-1-neopentyl-3-(tetrazol-5-yl)methyl-1,2,3,5-tetrahydro-4,1-benzothaizepin-2-one

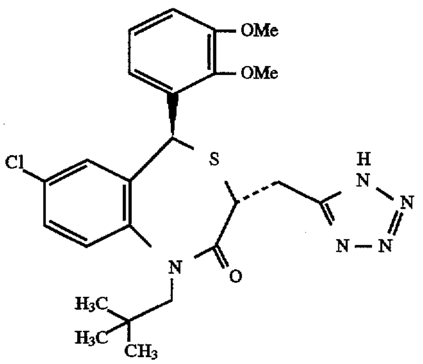

By employing (3R,5S)-7-chloro-5-(2,3-dimethoxyphenyl)-1-neopentyl-2-oxo-1,2,3,5-tetrahydro-4,1-benzothiazepine-3-acetic acid, substantially the same procedure was taken as in the case of Example 58 to give the captioned compound.

(1) 3-[(3R,5S)-7-Chloro-5-(2,3-dimethoxyphenyl)-1-neopentyl-2-oxo-1,2,3,5-tetrahydro-4,1-benzothiazepine-3-acetylamino]propionitrile $^1$H-NMR($CDCl_3$) δ: 0.991(9H, s), 2.336(1H,dd,J=3.8, 14.8 Hz), 2.54–2.63(2H,m), 2.938(1H, dd,J=10.6,14.8 Hz), 3.217(1H,d,J=13.6 Hz), 3.39–3.50(2H,m), 3.720(3H,s), 3.778(1H,dd,(J=3.8,10.6 Hz), 3.892(3H, s), 4.455(1H,d,J=13.6 Hz), 6.279(1H, s), 6.60–6.66(1H,br), 6.821(1H, d,J=1.8 Hz), 6.981(1H,dd,J=1.4, 8.0 Hz), 7.16–7.39(4H,m)

(2) (3R,5S)-7-Chloro-3-[1-(2-cyanoethyl)tetrazol-5-yl]methyl-5-(2,3-dimethoxyphenyl)-1-neopentyl-1,2,3,5-tetrahydro-4,1-benzothiazepin-2-one $^1$H-NMR($CDCl_3$) δ: 0.962(9H,s), 2.97–3.17(4H,m), 3.473(1H,dd,J=10.6,14.6 Hz), 3.729(3H,s), 3.902(3H,s), 4.020(1H,dd,J=3.6, 10.6 Hz), 4.306(1H,d,J=14.0 Hz), 4.74–4.81(2H,m), 6.333(1H,s), 6.84–7.77(6H,m)

(3) (3R,5S)-7-Chloro-5-(2,3-dimethoxyphenyl)-1-neopentyl-3-(tetrazol-5-yl)methyl-1,2,3,5-tetrahydro-4,1-benzothiazepin-2-one m.p. 139°–144° C.

Elemental Analysis for $C_{24}H_{28}ClN_5O_3S$: Calcd.: C, 57.42; H, 5.62; N. 13.95 Found: C, 57.55; H, 5.76; N, 13.78

Example 60

(3R,5S)-7-Chloro-5-(2-chlorophenyl)-3-(2-hydroxyethyl)-1-neopentyl-1,2,3,5-tetrahydro-4,1-benzoxazepine

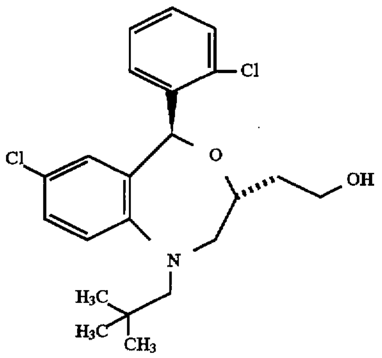

To tetrahydrofuran (20 ml) were added (3R,5S)-7-Chloro-5-(2-chlorophenyl)-1-neopentyl-2-oxo-1,2,3,5-tetrahydro-4,1-benzoxazepine-3-acetic acid (2 g) and aluminum lithium hydride (0.4 g). The mixture was heated for 6 hours under reflux, to which was added water. Insolubles were then filtered off. The filtrate was concentrated, which was purified by means of a silica gel column chromatography (hexane:acetic acid ethyl ester=2:1 v/v as an eluent) to give 1.65 g of non-crystalline solid matter.

$^1$H-NMR(CDCl$_3$) δ: 0.963(9H,s), 1.69–1.83(2H,m), 2.45 (1H,br), 2.563(1H,d,J=14.6 Hz), 3.090(1H,d,J=10.6 Hz), 3.72–3.84(4H,m), 3.96–4.14(1H,m), 6.344(1H,d,J=2.4 Hz), 6.596(1H,s), 7.05–7.71(6H,m)

Example 61

3,5-trans-7-Chloro-5-(2-chlorophenyl)-1-neopentyl-3-(tetrazol-5-yl)methylaminocarbonylmethyl-2-oxo-1,2,3,5-tetrahydro-4,1-benzothiazepine

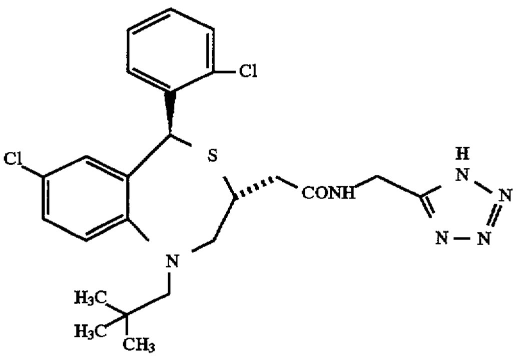

To a dimethylformamide solution of 3,5-trans-7-chloro-5-(2-chlorophenyl)-1-neopentyl-2-oxo-1,2,3,5-tetrahydro-4,1-benzothiazepine-3-acetic acid (0.2 g) obtained in Example 9 and aminoacetonitrile bisulfate (0.12 g) were added diethyl cyanophosphonate (0.12 g) and triethylamine (0.14 ml). The mixture was stirred for 40 minutes at 0° C. To the reaction mixture was added ice-water, which was extracted with acetic acid ethyl ester. The extract solution was washed with water, which was then dried over anhydrous sodium sulfate. The solvent was distilled off, and the residue was recrystallized from hexane to give 0.19 g of 3,5-trans-7-chloro-5-(2-chlorophenyl)-1-neopentyl-3-(cyanomethylaminocarbonylmethyl)-2-oxo-1,2,3,5-tetrahydro-4,1-benzothiazepine, m.p. 233°–234° C. To a solution of this compound (0.2 g) in toluene (2 ml) were added trimethylsilyl azide (50 mg) and dibutyl tin(IV) oxide (33 mg). The mixture was stirred for 24 hours at temperatures ranging from 110° to 120° C. The reaction mixture was concentrated, to which was added ethyl ether (20 ml), followed by washing with a dilute aqueous solution of sodium hydroxide. The aqueous layer was made acid with 1N HCl, which was extracted with acetic acid ethyl ester. The organic layer was washed with water and, then, dried over anhydrous sodium sulfate. The solvent was distilled off, and the residue was recrystallized from dichloromethane-hexane to give 0.21 g of colorless crystals, m.p. 264°–265° C.

Elemental Analysis for $C_{24}H_{26}Cl_2N_6O_2$.0.8$H_2$: Calcd.: C, 53.31; H, 5.00; N, 15.54 Found: C, 53.58; H, 5.14; N, 15.33

Example 62

7-Chloro-5-(2-chlorophenyl)-2,4-dioxo-1-neopentyl-2,3,4,5-tetrahydro-1H-1,5-benzodiazepine-3-acetic acid ethyl ester

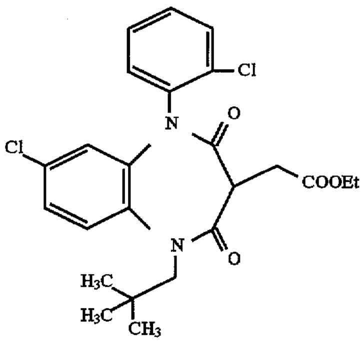

(1) 2',5-Dichloro-2-neopentylaminodiphenylamine

To an ethanol (50 ml) solution of 2-amino-2',5-dichlorodiphenylamine (2.35 g) were added pival aldehyde (1.21 ml) and acetic acid (0.67 g). The mixture was stirred for one hour at room temperature. To the reaction mixture was added sodium cyanoborohydride (0.97 g), which was stirred overnight. The reaction mixture was concentrated, to which was added acetic acid ethyl ester (100 ml). The mixture was washed with water and, then dried over anhydrous sodium sulfate, followed by distilling off the solvent. The residue was purified by means of a silica-gel column chromatography (hexane:toluene=5:1 v/v as an eluent) to give 1.7 g of an oily compound.

$^1$H-NMR(CDCl$_3$) δ: 0.89(9H,s), 2.86(2H,d,J=5.2 Hz), 4.08(1H,br), 5.66(1H,br), 6.5–6.85(3H,m), 7.0–7.2(3H,m), 7.34(1H,dd,J=8.0,1.6 Hz)

(2) 7-Chloro-5-(2-chlorophenyl)-2,4-dioxo-1-neopentyl-2,3,4,5-tetrahydro-1H-1,5-benzodiazepine To a tetrahydrofuran (25 ml) solution of 2',5-dichloro-2-neopentylaminodiphenylamine (3.7 g) was added dropwise a tetrahydrofuran (5 ml) solution of malonyl dichloride (1.33 ml) at 0° C. The mixture was stirred for one hour at room temperature, then for two hours at 60° C. The reaction mixture was concentrated, to which was added acetic acid ethyl ester (100 ml). The mixture was washed with water, then dried over anhydrous sodium sulfate, followed by distilling off the solvent. The residue was purified by means of a silica gel column chromatography (hexane:acetic acid ethyl ester=2:1 v/v as an eluent) to give 1.20 g of colorless crystals, m.p. 245°–246° C.

Elemental Analysis for $C_{20}H_{20}Cl_2N_2O_2$: Calcd.: C, 61.39; H, 5.15; N, 7.16 Found: C, 61.10; H, 5.04; N, 6.99

(3) 7-Chloro-5-(2-chlorophenyl)-2,4-dioxo-1-neopentyl-2,3,4,5-tetrahydro-1H-1,5-benzodiazepine-3-acetic acid ethyl ester To a solution of 7-chloro-5-(2-chlorophenyl)-2,4-dioxo-1-neopentyl-2,3,4,5-tetrahydro-1H-1,5-benzodiazepine (0.3 g) and chloroacetic acid ethyl ester (0.11 ml) in dimethylformamide (2 ml) was added sodium hydride (60% oil, 40 mg), and the mixture was stirred for 30 minutes at room temperature. To the reaction mixture were further added sodium hydride (40 mg×3) and chloroacetic acid ethyl ester (0.11 ml), which was stirred for 3 hours. To the mixture was then added acetic acid ethyl ester (50 ml), which was washed with water. The solvent was distilled off, and the residue was purified by means of a silica-gel column chromatography (hexane:acetic acid ethyl ester=4:1 v/v as an eluent) to give 0.25 g of colorless crystals, m.p. 152°–153° C.

Elemental Analysis for $C_{24}H_{26}Cl_2N_2O_4$: Calcd.: C, 60.38; H, 5.49; N, 5.87 Found: C, 60.22; H, 5.61; N, 6.05

Example 63

7-Chloro-5-(2-chlorophenyl)-2,4-dioxo-1-neopentyl-2,3,4,5-tetrahydro-1H-1,5-benzodiazepine-3-acetic acid

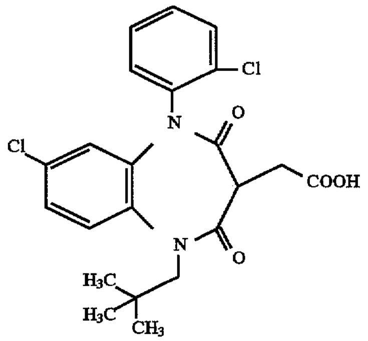

7-Chloro-5-(2-chlorophenyl)-2,4-dioxo-1-neopentyl-2,3,4,5-tetrahydro-1H-1,5-benzodiazepine-3-acetic acid ethyl ester (0.2 g) obtained in Example 62 was subjected to substantially the same procedure as in Example 57 to give 0.18 g of colorless crystals, m.p. 282°–285° C.

Elemental Analysis for $C_{22}H_{22}Cl_2N_2O_4$: Calcd.: C, 58.81; H, 4.94; N, 6.23 Found: C, 58.71; H, 5.15; N, 6.21

Example 64

(3R,5S)-7-Chloro-5-(2,4-dimethoxyphenyl)-1-neopentyl-2-oxo-1,2,3,5-tetrahydro-4,1-benzothiazepine-3-acetic acid sodium salt

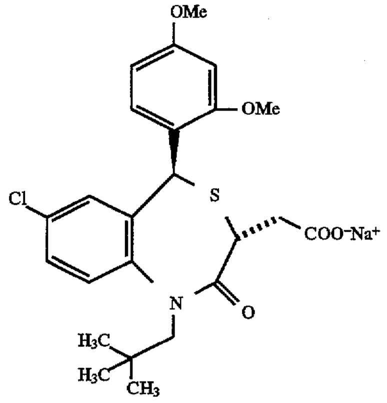

In methanol (50 ml) was dissolved (3R,5S)-7-chloro-5-(2,4-dimethoxyphenyl)-1-neopentyl-2-oxo-1,2,3,5-tetrahydro-4,1-benzothiazepine-3-acetic acid (1.275 g) obtained in Example 51. To the solution was added 1N aqueous solution of sodium hydroxide (2.57 ml), which was concentrated. The concentrate was washed with acetic acid ethyl ester to give 1.23 g of colorless crystals melting at not lower than 300° C.

$[\alpha]_D^{24}$–267.7° (c=0.64, MeOH)

Elemental Analysis for $C_{24}H_{27}ClNO_5SNa.0.7H_2O$: Calcd.: C, 56.24; H, 5.58; N, 2.73 Found: C, 56.16; H, 5.80; N, 2.81

Example 65

3,5-trans-7-Chloro-5-(2-chlorophenyl)-1,2,3,5-tetrahydro-4,1-benzothiazepine-3-acetic acid methyl ester

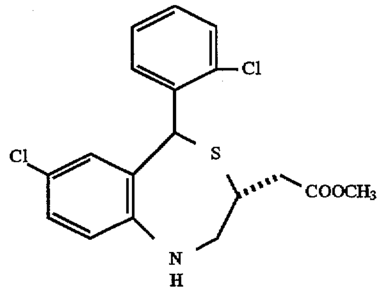

To a solution of 3,5-trans-7-chloro-5-(2-chlorophenyl)-2-oxo-1,2,3,5-tetrahydro-4,1-benzothiazepine-3-acetic acid methyl ester (0.5 g) in dichlodichloromethane (5 ml) was added tetrabutylammonium borohydride (0.96 g). The mixture was refluxed for 7 hours. The solvent was distilled off. To the residue was added 1N HCl (8 ml) and the mixture was refluxed for 10 minutes. The solution was neutralized with a 1N aqueous solution of sodium hydroxide, which was extracted with dichloromethane. The extract solution was dried over anhydrous sodium sulfate. The solvent was distilled off, and the residue was purified by means of a silica-gel column chromatography (hexane:acetic acid ethyl ester=3:1 v/v as an eluent) to give 0.13 g of a colorless oily product.

$^1$H-NMR($CDCl_3$) δ: 2.97(1H,dd,J=5.8,16.0 Hz), 3.20(1H, dd,J=8.0,16.0 Hz), 3.26(1H,dd,J=2.4,13.4 Hz), 3.35–3.42 (1H,m), 3.61(1H,dd,J=4.8,13.4 Hz), 3.68(3H,s), 5.96(1H,s), 6.55(1H,d,J=2.2 Hz), 6.83(1H,d,J=8.2 Hz), 7.03(1H,dd,J= 2.4,8.2 Hz), 7.28–7.56(4H,m)

Example 66

3,5-trans-7-Chloro-5-(2-chlorophenyl)-1,2,3,5-tetrahydro-4,1-benzoxazepine-3-acetic acid ethyl ester

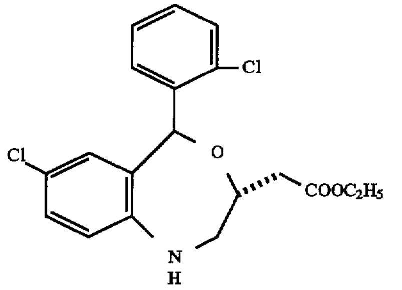

(1) 5-Chloro-2-(2,4-dimethoxybenzylamino)-α-(2-chlorophenyl)benzyl alcohol

2-Amino-5-chloro-α-(2-chlorophenyl)benzylalcohol (20 g) and 2,4-dimethoxybenzaldehyde (12.5 g) were subjected to substantially the same procedure as in Example 30 to give 33 g of an oily compound.

$^1$H-NMR($CDCl_3$) δ: 3.75(3H,s), 3.76(3H,s), 4.23(2H,s), 6.10(1H,s), 6.35–6.44(2H,m), 6.63(1H,d,J=8.8 Hz), 6.88 (1H,d,J=2.6 Hz), 7.03–7.12(2H,m), 7.24–7.45(4H,m)

(2) 3-[N-[4-Chloro-2-(2-chloro-α-hydroxybenzyl)phenyl]-N-(2,4-dimethoxybenzyl)carbamoylacrylic acid ethyl ester 5-Chloro-2-(2,4-dimethoxybenzylamino)-α-(2-chlorophenyl)benzyl alcohol (33 g) and fumaric chloride monoethyl ester (12.8 g) were subjected to substantially the same procedure as in Example 30 to give 48.9 g of an oily compound.

$^1$H-NMR($CDCl_3$) δ: 1.18–1.35(3H,m), 3.46(3H,s), 3.78 (3H,s), 3.82,3.83(2H, each s), 3.94–4.34(2H,m), 4.64(½× 1H,d,J=14.2 Hz), 5.48(½×1H,d,J=14.2 Hz), 6.02–8.00(12H, m)

(3) 3,5-trans-7-Chloro-5-(2-chlorophenyl)-1-(2,4-dimethoxybenzyl)-2-oxo-1,2,3,5-tetrahydro-4,1-benzoxazepine-3-acetic acid ethyl ester To a solution of the compound (48.9 g) obtained in (2) in ethanol (500 ml) was added potassium carbonate (12.4 g). The mixture was stirred overnight at room temperature. The solvent was distilled off. To the residue was added dichloromethane (200 ml), which was washed with water and dried over anhydrous sodium sulfate. The solvent was distilled off, and the residue was recrystallized from a mixture solvent of dichloromethane-hexane to give 41.4 g of colorless crystals, m.p. 135°–136° C.

(4) 3,5-trans-7-Chloro-5-(2-chlorophenyl)-2-oxo-1,2,3,5-tetrahydro-4,1-benzoxazepine-3-acetic acid ethyl ester The compound (5 g) obtained in (3), potassium persulfate (10 g) and dipotassium hydrogenphosphate (3.3 g) were added to a mixture solvent of acetonitrile (80 ml) and water (40 ml), which was refluxed for 2 hours. To the reaction mixture was added water, which was extracted with ethyl acetate. The extract solution was dried over anhydrous sodium sulfate. The solvent was distilled off. The residue was purified by means of a silica-gel column chromatography (hexane:acetic acid ethyl ester=3:1 v/v as an eluent) to give 1.83 g of colorless crystals, m.p. 132°–137° C.

(5) 3,5-trans-7-Chloro-5-(2-chlorophenyl)-1,2,3,5-tetrahydro-4,1-benzoxazepine-3-acetic acid ethyl ester The compound (1.8 g) obtained in (4) was subjected to substantially the same procedure as in Example 65 to give 0.69 g of a colorless oily product.

$^1$H-NMR($CDCl_3$) δ: 1.14(3H,t,J=7.2 Hz), 2.54(1H,dd,J= 6.6,15.0 Hz), 2.73(1H,dd,J=7.4,15.0 Hz), 3.29–3.32(2H,m), 4.05(2H,q,J=7.2 Hz), 4.20–4.32(1H,m), 6.33(1H,s), 6.64 (1H,d,J=2.4 Hz), 6.72(1H,d,J=8.4 Hz), 7.04–7.43(5H,m)

Example 67

3,5-trans-7-Chloro-5-(2-chlorophenyl)-1-propyl-1,2,3,5-tetrahydro-4,1-benzothiazepine-3-acetic acid methyl ester

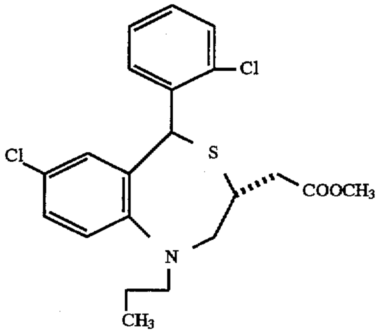

To a solution of 3,5-trans-7-chloro-5-(2-chlorophenyl)-1,2,3,5-tetrahydro-4,1-benzothiazepine-3-acetic acid methyl ester (0.1 g) obtained in Example 65 in methanol (2 ml) were added propionaldehyde (76 mg) and acetic acid (24 mg). The mixture was stirred for 30 minutes at room temperature. To the reaction mixture was added sodium cyano borohydride (25 mg), which was stirred for further one hour at room temperature. To the reaction mixture was added dichloromethane (50 ml), which was washed with water and dried over anhydrous sodium sulfate. The solvent was distilled off to leave 0.13 g of a colorless oily product.

$^1$H-NMR($CDCl_3$) δ: 0.99(3H,t,J=7.4 Hz), 1.46–1.63(2H, m), 2.76–3.05(5H,m), 3.24–3.46(2H,m), 3.68(3H,s), 6.43 (1H,s), 6.53(1H,d,J=2.4 Hz), 7.05–7.42(5H,m), 7.73–7.77 (1H,m)

Example 68

3,5-trans-7-Chloro-5-(2-chlorophenyl)-1-propyl-1,2,3,5-tetrahydro-4,1-benzoxazepine-3-acetic acid ethyl ester

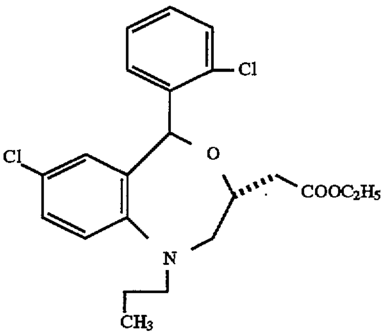

3,5-trans-7-Chloro-5-(2-chlorophenyl)-1,2,3,5-tetrahydro-4,1-benzoxazepine-3-acetic acid ethyl ester (0.1 g) obtained in Example 66 was subjected to substantially the same procedure as in Example 67 to give a colorless oily product (0.06 g).

$^1$H-NMR($CDCl_3$) δ: 0.98(3H,t,J=7.2 Hz), 1.19(3H,t,J=7.2 Hz), 1.57–1.74(2H,m), 2.53(1H,dd,J=5.8, 15.0 Hz), 2.74 (1H,dd,J=7.6,15.0 Hz), 2.92–3.06(2H,m), 3.27–3.47(2H,m), 4.10(2H,dq,J=1.4,7.2 Hz), 4.17–4.25(1H,m), 6.39(1H,d,J=2.4 Hz), 6.43(1H,s), 6.90(1H,d,J=8.6 Hz), 7.14(1H,dd,J=2.6,8.6 Hz), 7.28–7.63(4H,m)

Example 69

3,5-trans-7-Chloro-5-(2-chlorophenyl)-1-propyl-1,2,3,5-tetrahydro-4,1-benzothiazepine-3-acetic acid hydrochloride

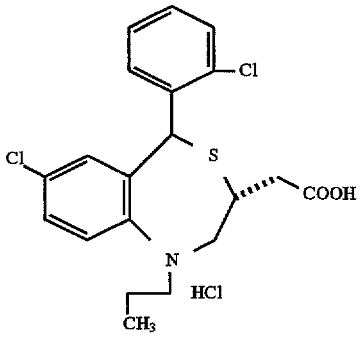

To a solution of 3,5-trans-7-chloro-5-(2-chlorophenyl)-1-propyl-1,2,3,5-tetrahydro-4,1-benzothiazepine-3-acetic acid methyl ester (0.13 g) obtained in Example 67 in dioxane (1 ml) was added 6N HCl (1 ml), and the mixture was refluxed for 30 minutes. The solvent was distilled off, and the residue was recrystallized from ethanol-hexane to give 57 mg of colorless crystals, m.p. 165°–168° C.

Elemental Analysis for $C_{20}H_{21}Cl_2NO_2S.HCl.0.3H_2O$: Calcd.: C, 53.12; H, 5.04; N, 3.10 Found: C, 53.21; H, 5.03; N, 3.34

Example 70

3,5-trans-7-Chloro-5-(2-chlorophenyl)-1-propyl-1,2,3,5-tetrahydro-4,1-benzoxazepine-3-acetic acid

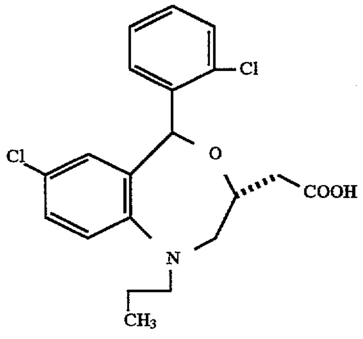

3,5-trans-7-Chloro-5-(2-chlorophenyl)-1-propyl-1,2,3,5-tetrahydro-4,1-benzoxazepine-3-acetic acid ethyl ester (0.15 g) obtained in Example 68 was subjected to reaction in substantially the same manner as in Example 69 to give 50 mg of colorless crystals, m.p. 105°–112° C.

Elemental Analysis for $C_{20}H_{21}Cl_2NO_3.HCl.0.6H_2O$: Calcd.: C, 54.40; H, 5.30; N, 3.17 Found: C, 54.33; H, 5.37; N, 3.31

Example 71

3,5-trans-7-Chloro-5-(2-chlorophenyl)-1-propionyl-1,2,3,5-tetrahydro-4,1-benzothiazepine-3-acetic acid methyl ester

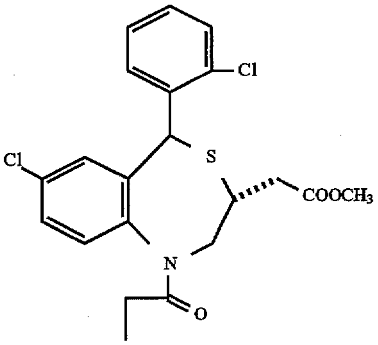

To a solution of 3,5-trans-7-chloro-5-(2-chlorophenyl)-1,2,3,5-tetrahydro-4,1-benzothiazepine-3-acetic acid methyl ester (100 mg) obtained in Example 65 in dichloromethane (2 ml) was added sodium hydrogencarbonate (59 mg). To the mixture was further added propionyl chloride (60 mg). The mixture was stirred for 2 hours at room temperature, to which was added dichloromethane (50 ml). The mixture was washed with water, then the solvent was distilled off. The residue was recrystallized from ethyl ether—petroleum ether to give 90 mg of colorless crystals, m.p. 191°–194° C.

$^1$H-NMR($CDCl_3$) δ: 1.14(3H,t,J=7.2 Hz), 2.07–2.33(2H, m), 2.83(1H,dd,J=7.6,16.8 Hz), 3.02(1H,dd,J=7.2,16.8 Hz), 3.24(1H,dd,J=3.0,13.6 Hz), 3.32–3.44(1H,m), 3.68(3H,s), 4.85(1H,dd,J=5.0,13.6 Hz), 6.00(1H,s), 6.60(1H,d,J=2.2 Hz), 7.11–7.63(6H,m)

Example 72

3,5-trans-7-Chloro-5-(2-chlorophenyl)-1-propionyl-1,2,3,5-tetrahydro-4,1-benzoxazepine-3-acetic acid ethyl ester

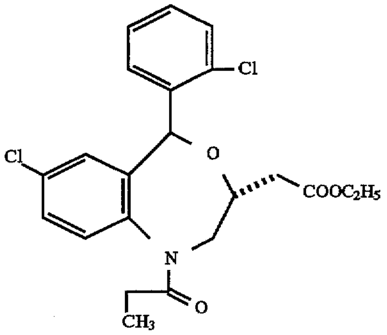

3,5-trans-7-Chloro-5-(2-chlorophenyl)-1,2,3,5-tetrahydro-4,1-benzoxazepine-3-acetic acid ethyl ester (100 mg) obtained in Example 67 was subjected to substantially the same procedure as in Example 72 to give 70 mg of an oily product.

$^1$H-NMR($CDCl_3$) δ: 1.07(3H,t,J=7.0 Hz), 1.16(3H,t,J=7.4 Hz), 2.14–2.52(2H,m), 2.61(1H,dd,J=5.4,15.4 Hz), 2.88 (1H,dd,J=9.2,15.4 Hz), 3.25(1H,dd,J=3.2,13.6 Hz), 3.85–4.16(2H,m), 4.24–4.40(1H,m), 4.56(1H,dd,J=6.0; 13.6 Hz), 6.29(1H,s), 6.50(1H,d,J=2.2 Hz), 7.16–7.68(6H,m)

Example 74

3,5-trans-7-Chloro-5-(2-chlorophenyl)-1-propionyl-1,2,3,5-tetrahydro-4,1-benzothiazepine-3-acetic acid

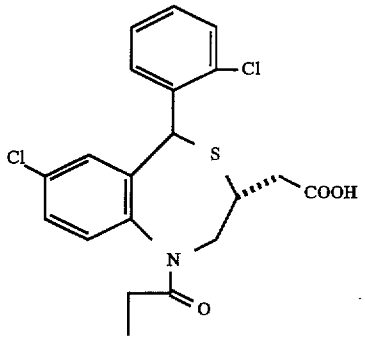

To a solution of 3,5-trans-7-chloro-5-(2-chlorophenyl)-1-propionyl-1,2,3,5-tetrahydro-4,1-benzothiazepine-3-acetic acid methyl ester (90 mg) obtained in Example 72 in dioxane (2 ml) was added 2N HCl (1 ml). The mixture was refluxed for 2 hours, to which was added dichloromethane (50 ml). The mixture was washed with water, then the solvent was distilled off. The residue was recrystallized from ethyl ether—hexane to give 52 mg of colorless crystals, m.p. 230°–232° C.

Elemental Analysis for $C_{20}H_{19}Cl_2NO_3S$: Calcd.: C, 56.61; H, 4.51; N, 3.30 Found: C, 56.26; H, 4.65; N, 3.51

Example 75

3,5-trans-7-Chloro-5-(2-chlorophenyl)-1-propionyl-1,2,3,5-tetrahydro-4,1-benzoxazepine-3-acetic acid

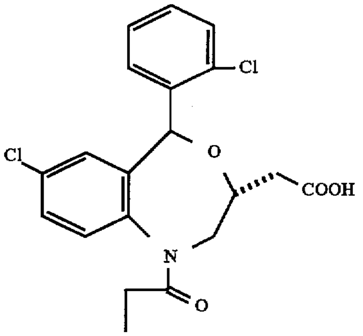

3,5-trans-7-Chloro-5-(2-chlorophenyl)-1-propionyl-1,2,3,5-tetrahydro-4,1-benzoxazepine-3-acetic acid ethyl ester (70 mg) obtained in Example 72 was subjected to substantially the same procedure as in Example 73 to give 43 mg of colorless crystals, m.p. 187°–190° C.

Elemental Analysis for $C_{20}H_{19}Cl_2NO_4$: Calcd.: C, 58.84; H, 4.69; N, 3.43 Found: C, 58.75; H, 4.67; N, 3.59

Example 75

3,5-trans-7-Chloro-5-(2-chlorophenyl)-1-neopentyl-1,2,3,5-tetrahydro-4,1-benzoxazepine-3-acetic acid tert-butyl ester

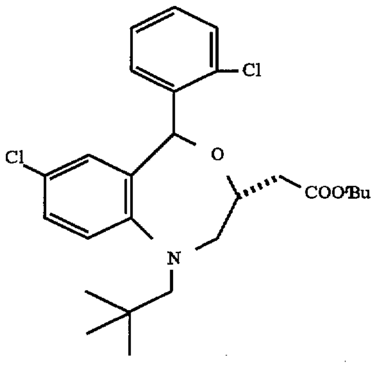

(1) 3,5-trans-7-Chloro-5-(2-chlorophenyl)-1-neopentyl-2-oxo-1,2,3,5-tetrahydro-4,1-benzoxazepine-3-acetic acid tert-butyl ester To a solution of 3,5-trans-7-chloro-5-(2-chlorophenyl)-1-neopentyl-2-oxo-1,2,3,5-tetrahydro-4,1-benzoxazepine-3-acetic acid (2 g) in dichloromethane (20 ml) were added isobutene (1 ml) and conc. sulfuric acid (0.05 mg). The mixture was left standing for 24 hours in a sealed vessel. The solution was washed with water and dried over anhydrous sodium sulfate. The solvent was distilled off, and the residue was purified by means of a silica-gel column chromatography (hexane:acetic acid ethyl ester=5:1 v/v as an eluent) to give 1.67 g of colorless crystals, m.p. 145°–147° C.

(2) 3,5-trans-7-Chloro-5-(2-chlorophenyl)-1-neopentyl-1,2,3,5-tetrahydro-4,1-benzoxazepine-3-acetic acid tert-butyl ester To a dichloromethane solution of the compound (1 g) obtained in (1) was added tetrabutylammonium borohydride (1.57 g). The mixture was then subjected to substantially the same procedure as in Example 65 to give 0.52 g of a colorless oily product.

$^1$H-NMR($CDCl_3$) δ: 0.95(9H,s), 1.44(9H,s), 2.33(1H,dd, J=5.0, 15.4 Hz), 2.55(1H,dd,J=7.8,15.4 Hz), 2.56(1H,d,J=13.2 Hz), 3.09(1H,dd,J=1.8,11.2 Hz), 3.63–3.78(2H,m), 4.12–4.26(1H,m), 6.32(1H,s), 6.59(1H,s), 7.11–7.76(6H,m)

Example 77

3,5-trans-7-Chloro-5-(2-chlorophenyl)-1-neopentyl-1,2,3,5-tetrahydro-4,1-benzoxazepine-3-acetic acid

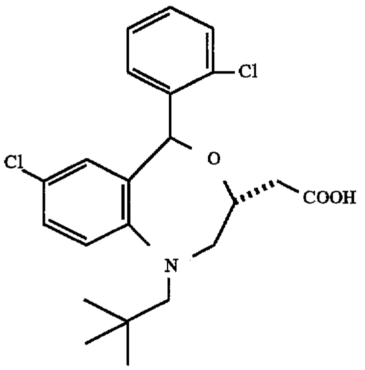

To a solution of 3,5-trans-7-chloro-5-(2-chlorophenyl)-1-neopentyl-1,2,3,5-tetrahydro-4,1-benzoxazepine-3-acetic acid tert-butyl ester (0.5 g) obtained in Example 75 in dioxane (5 ml) was added 2N aqueous hydrogen chloride solution (1 ml). The mixture was refluxed for 3 hours under reflux. The reaction mixture was neutralized with 1N NaOH, to which was added dichloromethane (100 ml), followed by washing with water. The solvent was distilled off. The residue was purified by means of a silica-gel column chromatography (dichloromethane:methanol:water=0:1:0.1 v/v as an eluent) to give 85 mg of colorless crystals, m.p. 195°–208° C.

Elemental Analysis for $C_{22}H_{25}Cl_2NO_3 \cdot 0.2H_2O$: Calcd.: C, 62.04; H, 6.01; N, 3.29 Found: C, 62.14; H, 6.01; N, 3.42

Assay Method of Squalene Synthetase Inhibitory Activity

The squalene synthetase inhibitory activity was assayed as follows with the enzyme solutions described in the subsequent Experimental Examples 1 and 2.

More specifically, an enzyme solution (protein content 0.8 ug) prepared in Experimental Example 1 or 2 was added to a solution (total volume 50 µl)) containing 5 uM [1-$^3$H] farnesyl pyrophosphate (specific activity 25 uCi/mole), 1 mM NADPH, 5 mM $MgCl_2$, 6 mM glutathione, a 100 mM buffer solution of potassium phosphate (pH 7.4) and a test drug (used as an aqueous solution or a DMSO solution), then the reaction was allowed to proceed at 37° C. for 45 minutes. To the reaction mixture was added 150 µl of a mixture of chloroform and methanol (1:2) to suspend the reaction, followed by adding 50 µl of chloroform and 50 µl of a 3N aqueous solution of sodium hydroxide. 50 µl of the chloroform layer (lower layer) containing the reaction mixture having squalene as the principal component and 3 ml of toluene-based liquid scintillator were mixed, and its radioactivity was determined by means of a liquid scintillation counter.

The squalene synthetase inhibitory activity was expressed in terms of the concentration inhibiting by 50% the radioactivity taken into the chloroform layer ($IC_{50}$, molar concentration (M)).

Experimental Example 1

Preparation of rat-derived enzyme

An SD male rat (6 week old) was killed by bleeding, and its liver was excised. About 10 g of the liver was washed with a saline solution cooled with ice, which was then homogenized in 15 ml of an ice-cooled buffer solution [100 mM potassium phosphate (pH 7.4), 15 mM nicotinamide, 2 mM $MgCl_2$], followed by centrifugation for 20 minutes (4° C.) with 10000×g. The supernatant layer was separated and subjected to further centrifugation for 90 minutes (4° C.) at 105000×g. The sediment was then suspended in an ice-cooled 100 mM phosphate buffer solution (pH 7.4), which was again subjected to centrifugation for 90 minutes (4° C.) at 105000×g. The sediment thus obtained (microsome fraction) was suspended in an ice-cooled 100 mM potassium phosphate buffer (pH 7.4) (about 40 mg/ml protein concentration, determined with BCA protein assay kit of Pias Co., Ltd.). This suspension was used as the enzyme solution.

Experimental Example 2

Preparation of human-derived enzyme

Human hepatic carcinoma cells HepG2 (about $1 \times 10^9$ cells) obtained by incubation in a Dulbecco-modified Eagle's medium (37° C. in the presence of 5% $CO_2$) were suspended in 10 ml of an ice-cooled buffer solution [100 mM potassium phosphate buffer (pH 7.4), 30 mM nicotinamide and 2.5 mM $MgCl_2$]. The cells were crashed by means of ultrasonication (for 30 seconds, twice). From the sonicate thus obtained, the microsome fraction was obtained by the same procedure as in Experiment Example 1, which was suspended in an ice-cooled 100 mM potassium phosphate buffer (pH 7.4) (about 4 mg/ml protein concentration). This suspension was used as the enzyme solution. The results are shown in [Table 4].

TABLE 4

| Compound No. | Rat-derived enzyme ($10^{-7}$M) | Human-derived enzyme ($10^{-7}$M) |
|---|---|---|
| Examples 8-1 |  | 20 |
| 9 | 1.8 | 0.39 |
| 10-2 | 0.62 | 0.42 |
| 10-3 | 9.2 |  |
| 10-4 | 1.0 |  |
| 10-5 | 0.51 | 0.25 |
| 10-6 | 0.39 | 0.31 |
| 10-7 | 0.26 | 0.13 |
| 10-8 | 0.23 | 0.13 |
| 13 | 39 |  |
| 14 | 4.3 | 1.6 |
| 19 | 7.0 |  |
| 21 | 33 |  |
| 23 | 0.22 | 0.13 |
| 26 | 3.9 | 1.2 |
| 28 | 4.6 |  |
| 31 | 1.7 |  |
| 33 | 0.88 | 0.73 |
| 34 | >10 |  |
| 36 | 4.9 |  |
| 43 | 0.093 | 0.059 |
| 44 | 9.6 |  |
| 50 | >10 |  |
| 51 | 0.21 | 0.18 |
| 53 | 2.9 | 1.3 |
| 59 | 0.16 | 0.10 |

Formulation Examples

A squalene synthetase inhibiting agent containing, as its effective component, a compound represented by the formula (I), (I'), (I") or (I''') of this invention or a salt thereof, in the case where it is used as a therapeutic agent of hypercholesteremia, can be formulated in accordance with, dfor example, the following prescriptions.

| 1. Capsules | |
|---|---|
| (1) Compound obtained in Example 10-8 | 10 mg |
| (2) Lactose | 90 mg |
| (3) Microcrystalline cellulose | 70 mg |
| (4) Magnesium stearate | 10 mg |
| One capsule | 180 mg |

(1), (2) and (3) and one half of (4) were blended and the mixture was granulated, to which was added the balance of (4). The mixture was filled in a gelatin capsule.

| 2. Tablets | |
|---|---|
| (1) Compound obtained in Example 10-8 | 10 mg |
| (2) Lactose | 35 mg |
| (3) Corn starch | 150 mg |
| (4) Microcrystalline cellulose | 30 mg |
| (5) Magnesium stearate | 5 mg |
| One tablet | 230 mg |

(1), (2) and (3) and two thirds of (4) and one half of (5) were blended and the mixture was granulated, to which were added the balance of (4) and (5). The mixture was subjected to compression-molding to provide tablets.

| 3. Injections | |
|---|---|
| (1) Sodium salt of the compound obtained in Example 10-8 | 10 mg |
| (2) Inositol | 100 mg |
| (3) Benzyl alcohol | 20 mg |
| One ampoule | 130 mg |

(1), (2) and (3) were dissolved in distilled water for injection to make the whole volume 2 ml, which was put in an ampoule, and the ampoule was sealed. All the processes were conducted under sterilized conditions.

| 4. Capsules | |
|---|---|
| (1) Compound obtained in Example 9 | 10 mg |
| (2) Lactose | 90 mg |
| (3) Microcrystalline cellulose | 70 mg |
| (4) Magnesium stearate | 10 mg |
| One capsule | 180 mg |

(1), (2) and (3) and one half of (4) were blended and the mixture was granulated, to which was added the balance of (4). The mixture was filled in a gelatin capsule.

| 5. Tablets | |
|---|---|
| (1) Compound obtained in Example 9 | 10 mg |
| (2) Lactose | 35 mg |
| (3) Corn starch | 150 mg |
| (4) Microcrystalline cellulose | 30 mg |
| (5) Magnesium stearate | 5 mg |
| One tablet | 230 mg |

(1), (2) and (3) and two thirds of (4) and one half of (5) were blended and the mixture was granulated, to which were added the balance of (4) and (5). The mixture was subjected to compression-molding to provide tablets.

| 6. Injections | |
|---|---|
| (1) Sodium salt of the compound obtained in Example 9 | 10 mg |
| (2) Inositol | 100 mg |
| (3) Benzyl alcohol | 20 mg |
| One ampoule | 130 mg |

(1), (2) and (3) were dissolved in distilled water for injection to make the whole volume 2 ml, which was put in an ampoule, and the ampoule was sealed. All the processes were conducted under sterilized conditions.

What is claimed is:

1. A compound of the formula (I):

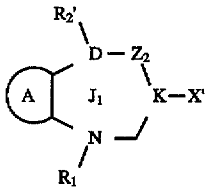

(I)

in which $R_1$ is hydrogen or a hydrocarbon group selected from the group consisting of (1) $C_{1-7}$ alkyl,
(2) $C_{2-6}$ alkenyl,
(3) $C_{2-6}$ alkynyl,
(4) $C_{3-9}$ cycloalkyl,
(5) 2-cyclopenten-1-yl, 3-cyclopenten-1-yl, 2-cyclohexen-1-yl, 3-cyclohexen-1-yl, 1-cyclobuten-1-yl or 1-cyclopenten-1-yl,
(6) 2,4-cyclopentadien-1-yl, 2-4-cyclohexadien-1-yl or 2,5-cyclohexadien-1-yl,
(7) phenyl, naphthyl, anthryl, phenanthryl or acenaphthylenyl, and
(8) $C_{1-5}$ acyl group which may be substituted by one to five halogens;

$R_2'$ is phenyl which may be substituted by one to three substituents selected from the group consisting of (1) halogen,
(2) $C_{1-4}$ alkyl which may be substituted by 1 to 5 halogens,
(3) $C_{1-4}$ alkoxy which may be substituted by 1 to 5 halogens,
(4) hydroxyl which may be substituted by (i) $C_{1-4}$ alkyl, (ii) $C_{3-6}$ cycloalkyl, (iii) phenyl, 1-naphthyl or 2-naphthyl, or (iv) benzyl or phenethyl,
(5) nitro and
(6) cyano;

X' is $-X_1-Y$ wherein $X_1$ is $C_{1-7}$ alkylene, Y is (A) carboxyl, methoxycarbonyl, ethoxycarbonyl, propoxycarbonyl, isopropoxycarbonyl, butoxycarbonyl, tert-butoxycarbonyl, sec-butoxycarbonyl, pentyloxycarbonyl, isopentyloxycarbonyl, neopentyloxycarbonyl, phenoxycarbonyl, 1-naphthoxycarbonyl or benzyloxycarbonyl,
(B) carbamoyl which may be substituted by one or two substituents selected from the group consisting of
(1) $C_{1-6}$ alkyl which may be substituted by one to three substituents selected from the group consisting of (i)

carboxyl which may be esterified by $C_{1-5}$ alkyl, (ii) furyl, thienyl, indolyl, isoindolyl, pyrazinyl, pyridyl, pyrimidyl or imidazolyl, (iii) amino, (iv) hydroxyl and (v) phenyl, (2) $C_{3-6}$ cycloalkyl which may be substituted by one to three substituents selected from the group consisting of (i) carboxyl group which may be esterified by $C_{1-5}$ alkyl, (ii) furyl, thienyl, indolyl, isoindolyl, pyrazinyl, pyridyl, pyrimidyl or imidazolyl, (iii) amino, (iv) hydroxyl and (v) phenyl (3) phenyl, 1-naphthyl or 2-naphthyl, each of said groups being unsubstituted or substituted by (i) halogen atoms and (ii) carboxyl which may be esterified by a $C_{1-4}$ alkyl, and (4) benzyl or phenethyl, each of said groups being unsubstituted or substituted by (i) halogen or (ii) carboxyl which may be esterified by a $C_{1-4}$ alkyl, in which two substituents on the nitrogen atom of the carbamoyl group may form, taken together with the nitrogen, a cyclic amino group selected from the group consisting of 1-azetidinyl, 1-pyrrolidinyl, piperidino, morpholino and 1-piperzinyl;

(C) hydroxyl which may be substituted by (1) $C_{1-4}$ alkyl, (2) $C_{3-6}$ cycloalkyl, (3) phenyl, 1-naphthyl or 2-naphthyl, each of said groups being unsubstituted or substituted by (i) halogen or (ii) carboxyl which may be esterified by a $C_{1-4}$ alkyl, or (4) benzyl or phenethyl, each of said groups being unsubstituted or substituted by substituents selected from the group consisting of (i) halogen or (ii) carboxyl which may be esterified by a $C_{1-4}$ alkyl, (D) amino which may be substituted by (1) $C_{1-4}$ alkyl, (2) $C_{3-6}$ cycloalkyl, (3) phenyl, 1-naphthyl or 2-naphthyl, each of said groups being unsubstituted or substituted by (i) halogen or (ii) carboxyl group which may be esterified by a $C_{1-4}$ alkyl, or (4) benzyl or phenethyl, each of said groups being Unsubstituted or substituted by (i) halogen or (ii) carboxyl group which may be esterified by a $C_{1-4}$ alkyl, in which two substituents on the nitrogen atom of the amino group may form, taken together with the nitrogen, a cyclic amino group selected from the group consisting of 1-azetidinyl, 1-pyrrolidinyl, piperidino, morpholino and 1-piperzinyl, or (E) tetrazol-5-yl or a group represented by the formula

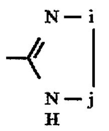

wherein i stands for —O— or —S—, j stands for —CO—, —CS— or —$SO_2$—, which may be substituted by $C_{1-4}$ alkyl, $C_{3-5}$ alkanoyl or benzoyl;

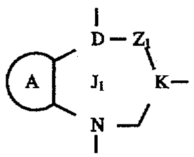

is a group selected from

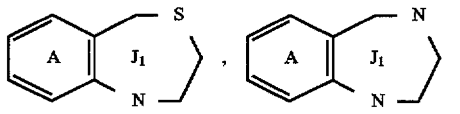
, ,

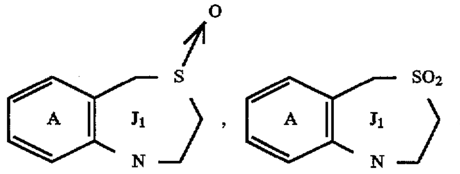
, ,

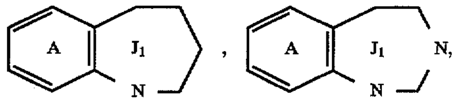
, ,

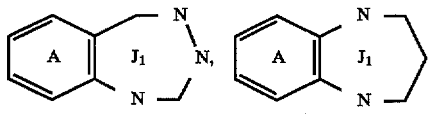
, and

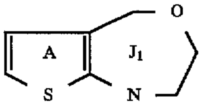
.

ring A may be substituted by one to three substituents selected from the group consisting of (1) halogen, (2) $C_{1-4}$ alkyl which may be substituted by one to three halogens, (3) $C_{1-4}$ alkoxy which may be substituted by one to three halogens, (4) nitro, and (5) cyano; and ring $J_1$ may have (1) oxo, or (2) thioxo, on the carbon atom of the ring $J_1$, provided that the condensed ring composed of Ring A and ring $J_1$ is not a 2-oxo-(2,3-dihydro or 2,3,5,-tetrahydro)-1H-1, 4-benzodiazepene ring.

2. The compound or the salt thereof as claimed in claim 1, in which $R_1$ is (i) $C_{1-7}$ alkyl, (ii) $C_{2-8}$ alkenyl or (iii) $C_{2-6}$ alkynyl.

3. The compound or the salt thereof as claimed in claim 2, in which $R_1$ is $C_{1-7}$ alkyl.

4. The compound or the salt thereof as claimed in claim 1, in which $R_1'$ is a phenyl substituted by one to three substituents selected from the group consisting of (1) halogen, (2) $C_{1-4}$ alkyl which may be substituted by one to three halogens, (3) $C_{1-4}$ alkoxy which may be substituted one to three halogens, (4) hydroxyl which may be substituted by (i) $C_{1-4}$ alkyl, (ii) $C_{3-6}$ cycloalkyl or (iii) phenyl, 1-naphthyl or 2-naphthyl, (5) nitro and (6) cyano.

5. The compound or the salt thereof as claimed in claim 1, in which X' is an alkyl substituted with an carboxyl, which may be esterified by methyl, ethyl, propyl, isopropyl, butyl, tert-butyl, sec-butyl, pentyl, isopentyl, neopentyl, phenyl, 1-naphthy or benzyl.

6. The compound or the salt thereof as claimed in claim 5, in which the alkyl is $C_{1-4}$ alkyl.

7. The compound or the salt thereof as claimed in claim 1, in which

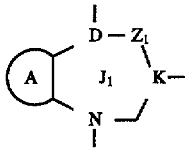

is a group selected from

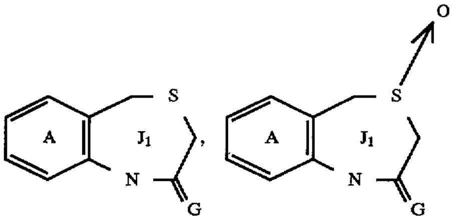

and

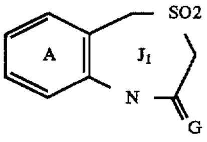

G is O or S.

8. The compound or the salt thereof as claimed in claim 1, in which

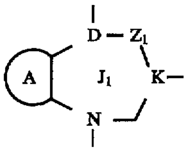

is a group selected from

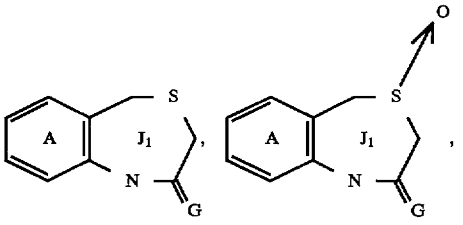

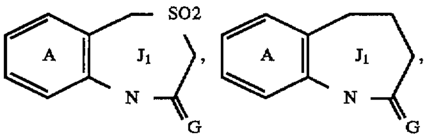

-continued

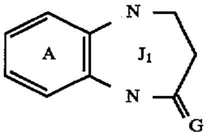

and

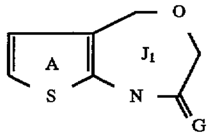

G is O or S.

9. The compound or the salt thereof as claimed in claim 1, which is 3,5-trans-7-chloro-5-(2-chlorophenyl)-1-neopenty]-2-oxo-1,2,3,5-tetrahydro-4,1-benzothiazepine-3-acetic acid,
3,5-trans-7-chloro-5-(2-chlorophenyl)-2-oxo-1,2,3,5-tetrahydro-4,1-benzothiazepine-3-acetic acid,
3,5-trans-7-chloro-5-(2-chlorophenyl)-1-isopropyl-2-oxo-1,2,3,5-tetrahydro-4,1-benzothiazepine-3-acetic acid,
3,5-trans-7-chloro-5-(2-chlorophenyl)-1-methyl-2-oxo-1,2,3,5-tetrahydro-4,1-benzothiazepine-3-acetic acid,
3,5-trans-7-chloro-5-(2-chlorophenyl)-1-ethyl-2-oxo-1,2,3,5-tetrahydro-4,1-benzothiazepine-3-acetic acid,
3,5-trans-7-chloro-5-(2-chlorophenyl)-1-isobutyl-2-oxo-1,2,3,5-tetrahydro-4,1-benzothiazepine-3-acetic acid,
3,5-trans-7-chloro-5-(2-methoxyphenyl)-1-isopropyl-2-oxo-1,2,3,5-tetrahydro-4,1-benzothiazepine-3-acetic acid,
3,5-trans-7-chloro-5-(2-methoxyphenyl)-1-isobutyl-2-oxo-1,2,3,5-tetrahydro-4,1-benzothiazepine-3-acetic acid,
3,5-trans-7-chloro-5-(2-methoxyphenyl)-1-neopentyl-2-oxo-1,2,3,5-tetrahydro-4,1-benzothiazepine-3-acetic acid,
(3R,5S)-1-Isobutyl-7-chloro-5-(2-chlorophenyl)-2,3,4,5-tetrahydro-2-oxo-1H-1,4-benzothiazepine-3-acetic acid,
3,5-trans-7-chloro-5-(2-chlorophenyl)-1-neopentyl-2-oxo-1,2,3,5-tetrahydro-4,1-benzothiazepine-3-acetic acid,
3,5-trans-7-chloro-5-(2-chlorophenyl)-1-neopentyl-2-oxo-1,2,3,5-tetrahydro-4,1-benzothiazepine-3-acetic acid S-dioxide,
7-chloro-5-(2-chlorophenyl)-1-isobutyl-2-oxo-2,3,4,5-tetrahydro-1H-[1]-benzazepine-3-acetic acid,
3,5-trans-7-chloro-5-(2-chlorophenyl)-1-neopentyl-1,2,3,5-tetrahydro-2-thioxo-4,1-benzothiazepine-3-acetic acid,
3,5-trans-7-chloro-5-(2-chlorophenyl)-1-neopentyl-2-oxo-1,2,3,5-tetrahydro-4,1-thieno[2,3-e]oxazepine-3-acetic acid,
3,5-trans-7-chloro-5-(2-methoxyphenyl)-1-neopentyl-2-oxo-1,2,3,5-tetrahydro-4,1-thieno[2,3-e]oxazepine-3-acetic acid,
3,5-cis-7-chloro-5-(2-methoxyphenyl)-1-neopentyl-2-oxo-1,2,3,5-tetrahydro-4,1-thieno[2,3-e]oxazepine-3-acetic acid,
3,5-trans-7-chloro-1-isobutyl-5-(2-methoxyphenyl)-2-oxo-1,2,3,5-tetrahydro-4,1-thieno[2,3-e]oxazepine-3-acetic acid,
3,5-cis-7-chloro-1-isobutyl-5-(2-methoxyphenyl)-2-oxo-1,2,3,5-tetrahydro-4,1-thieno[2,3-e]oxazepine-3-acetic acid,
3,5-trans-7-chloro-5-(2,3-dimethoxyphenyl)-1-neopentyl-2-oxo-1,2,3,5-tetrahydro-4,1-benzothiazepine-3-acetic acid,
(3R,5S)-7-chloro-5-(2,3-dimethoxyphenyl)-1-neopentyl-2-oxo-1,2,3,5-tetrahydro-4,1-benzothiazepine-3-acetic acid,
(3S,5R)-7-chloro-5-(2,3-dimethoxyphenyl)-1-neopentyl-2-oxo-1,2,3,5-tetrahydro-4,1-benzothiazepine-3-acetic acid,
3,5-trans-7-chloro-5-(2,4-dimethoxyphenyl)-1-neopentyl-2-oxo-1 ,2,3,5-tetrahydro-4,1-benzothiazepine-3-acetic acid, (3S,5R)-7-chloro-5-(2,4-dimethoxyphenyl)-1-neopentyl-2-oxo-1,2,3,5-tetrahydro-4,1-benzothiazepine-3-acetic acid, (3R,5S)-7-chloro-5-(2,4-dimethoxyphenyl)-1-neopentyl-2-oxo-1,2,3,5-tetrahydro-4,1-benzothiazepine-3-acetic acid, 7-chloro-5-(2-chlorophenyl)-1-neopentyl-2-oxo-1,2,4,5-tetrahydro-3H-1,3-benzodiazepine-3-acetic acid, 7-chloro-5-(2-chlorophenyl)-1-neopentyl-1,2-dihydro-2-oxo-3H-1,3,4-benzotriazepine-3-acetic acid, 7-chloro-5-(2-chlorophenyl)-2,4-dioxo-1-neopentyl-2,3,4,5-tetrahydro-1H-1,5-benzodiazepine-3-acetic acid, 3,5-trans-7-chloro-5-(2-chlorophenyl)-1,2,3,5-tetrahydro-4,1-benzothiazepine-3-acetic acid methyl ester, 3,5-trans-7-chloro-5-(2-chlorophenyl)-1,2,3,5-tetrahydro-4,1-benzoxazepine-3-acetic acid ethyl ester, 3,5-trans-7-chloro-5-(2-chlorophenyl)-1-propyl-1,2,3,5-tetrahydro-4,1-benzothiazepine-3-acetic acid hydrochloride, 3,5-trans-7-chloro-5-(2-chlorophenyl)-1-propyl-1,2,3,5-tetrahydro-4,1-benzoxazepine-3-acetic acid hydrochloride, 3,5-trans-7-chloro-5-(2-chlorophenyl)-1-propionyl-1,2,3,5-tetrahydro-4,1-benzoxazepine-3-acetic acid, 3,5-trans-7-chloro-5-(2-chlorophenyl)-1-propionyl-1,2,3,5-tetrahydro-4,1-benzoxazepine-3-acetic acid.

10. A compound, which is 3,6-trans-8-chloro-6-(2-chlorophenyl)-1-neopentyl-2-oxo-2,3,5,6-tetrahydro-1H-4,1-benzoxazocine-3-acetic acid or a pharmaceutically acceptable salt thereof.

11. A pharmaceutical composition which comprises the compound as claimed in claim 1 or a salt thereof, and a pharmaceutically acceptable carrier or excipient.

12. A method for inhibiting squalene synthetase in a mammal comprising administering a pharmaceutically effective amount of the compound as claimed in claim 1 or a salt thereof, to said mammal.

13. A method for prophylaxis or treatment of hypercholesterolemia or coronary sclerosis in a mammal comprising administering a pharmaceutically effective amount of the compound as claimed in claim 1 or a salt thereof, to said mammal.

14. A method for prophylaxis or therapy of fungal infection in a mammal comprising administering a pharmaceutically effective amount of the compound as claimed in claim 1 or a salt thereof, to said mammal.

15. A method for therapy of hyperlipidaemia is a mammal comprising administering a pharmaceutically effective amount of the compound as claimed in claim 1 or a salt thereof, to said mammal.

* * * * *

UNITED STATES PATENT AND TRADEMARK OFFICE
CERTIFICATE OF CORRECTION

PATENT NO. : 5,698,691

DATED : December 16, 1997

INVENTOR(S) : Hidefumi YUKIMASA et al.

It is certified that error appears in the above-identified patent and that said Letters Patent is hereby corrected as shown below:

Column 2, in formula (I), "$Z_2$" should be --$Z_1$--.

Column 4, in formula (I'"), "$Z_2$" should be --$Z_3$--.

Column 4, line 24, "-O- is" should be -- -O-; G is --.

Column 5, line 12, "cycloyalkenyl" should be --cycloalkenyl--.

Column 12, line 15, "$R_2$" should be --$R_1$--.

Column 12, line 25, "or" should be --on--.

Column 14, line 55, "RT" should be --$R_7$--.

Column 14, line 62, "neopentYl" should be --neopentyl--.

Column 15, line 28, "-1H" should be -- -1H- --.

Column 18, line 25, "(1V)" should be --(V)--.

Column 18, line 61, "bromic acid" should be --hydrobromic acid--.

Column 22, lines 6 and 13, "bromic acid" should be --hydrobromic acid--.

Column 24, formula (XIV), "$COOR_3$" should be --$COOR_6$--.

UNITED STATES PATENT AND TRADEMARK OFFICE

CERTIFICATE OF CORRECTION

PATENT NO. : 5,698,691

DATED : December 16, 1997

INVENTOR(S) : Hidefumi YUKIMASA et al.

It is certified that error appears in the above-identified patent and that said Letters Patent is hereby corrected as shown below:

Column 26, formula (XVI), "$COOR_8$" should be --$COOR_6$--.

Column 27, formula at the bottom of column 27, "$COOR_5$" should be --$COOR_6$--.

Column 37, between formulas (lg-1) and (lg-2), insert -- → --.

Column 40, line 37, "method" should be --methanol--.

Column 40, line 64, "-30" should be -- -20 --.

Column 104, formula (I), "$Z_2$" should be --$Z_1$--.

Column 104, line 35, "2-4-" should be -- 2,4- --.

Column 105, line 11, insert --,-- after "phenyl".

Column 105, lines 25 and 55, "piperzinyl" should be --piperazinyl--.

Column 105, line 47, "Unsubstituted" should be --unsubstituted--.

Column 106, line 52, insert ", or a salt thereof" after "ring".

Column 106, line 59, "$R_1$'" should be --$R_2$'--.

Column 106, line 62, insert "by" after "substituted"

Column 107, line 3, "naphthy" should be --naphthyl--.

UNITED STATES PATENT AND TRADEMARK OFFICE

CERTIFICATE OF CORRECTION

PATENT NO. : 5,698,691

DATED : December 16, 1997

INVENTOR(S) : Hidefumi YUKIMASA et al.

It is certified that error appears in the above-identified patent and that said Letters Patent is hereby corrected as shown below:

Column 108, line 12, "penty]" should be --pentyl--.

Column 108, line 32, "benzothiazepine" should be --benzodiazepine--.

Column 108, line 66, "1 ,2" should be --1,2--.

Column 110, line 21, "is" should be --in--.

Signed and Sealed this

Twelfth Day of May, 1998

Attest:

BRUCE LEHMAN

Attesting Officer

*Commissioner of Patents and Trademarks*